US010568496B2

(12) United States Patent
Blanquart et al.

(10) Patent No.: US 10,568,496 B2
(45) Date of Patent: Feb. 25, 2020

(54) CONTINUOUS VIDEO IN A LIGHT DEFICIENT ENVIRONMENT

(71) Applicant: Depuy Synthes Products, Inc., Raynham, MA (US)

(72) Inventors: Laurent Blanquart, Westlake Village, CA (US); Joshua D. Talbert, Cottonwood Heights, UT (US); Donald M. Wichern, South Ogden, UT (US); John Richardson, Calabasa, CA (US); Jeremiah D. Henley, Midvale, UT (US)

(73) Assignee: DePuy Synthes Products, Inc., Raynham, MA (US)

( * ) Notice: Subject to any disclaimer, the term of this patent is extended or adjusted under 35 U.S.C. 154(b) by 501 days.

(21) Appl. No.: 13/952,518

(22) Filed: Jul. 26, 2013

(65) Prior Publication Data
US 2014/0163319 A1 Jun. 12, 2014

Related U.S. Application Data

(60) Provisional application No. 61/790,487, filed on Mar. 15, 2013, provisional application No. 61/676,289, filed on Jul. 26, 2012.

(51) Int. Cl.
*A61B 1/05* (2006.01)
*A61B 1/00* (2006.01)
(Continued)

(52) U.S. Cl.
CPC ............ *A61B 1/05* (2013.01); *A61B 1/00009* (2013.01); *A61B 1/045* (2013.01); *A61B 1/0638* (2013.01)

(58) Field of Classification Search
CPC ...... H04N 5/3595; A61B 1/06; A61B 1/0638; A61B 1/0661
(Continued)

(56) References Cited

U.S. PATENT DOCUMENTS

| 3,666,885 A | * | 5/1972 | Hemsley | ................. | B41F 13/02 |
| | | | | | 250/559.15 |
| 4,011,403 A | | 3/1977 | Epstein et al. | | |

(Continued)

FOREIGN PATENT DOCUMENTS

| CN | 1520696 A | 8/2004 |
| CN | 101079966 A | 11/2007 |

(Continued)

OTHER PUBLICATIONS

Blumenfeld, et al. Three-dimensional image registration of MR proximal femur images for the analysis of trabecular bone parameters. Oct. 2008. [retrieved on Jul. 30, 2014] Retrieved from the internet: <URL: http://www.ncbi.nlm.nih.gov/pmc/articles/PMC2673590/>.

*Primary Examiner* — Timothy J Neal
*Assistant Examiner* — Jae Woo
(74) *Attorney, Agent, or Firm* — Terrence J. Edwards; TechLaw Ventures, PLLC

(57) ABSTRACT

The present disclosure extends to methods, systems, and computer program products for producing an image in light deficient environments and associated structures, methods and features is disclosed and described. The features of the system may include controlling a light source through duration, intensity or both; pulsing a component controlled light source during the blanking time; maximizing the blanking time to allow optimum light; and maintaining color balance.

18 Claims, 38 Drawing Sheets

(51) Int. Cl.
*A61B 1/045* (2006.01)
*A61B 1/06* (2006.01)

(58) Field of Classification Search
USPC .............................. 600/178, 180, 118, 160
See application file for complete search history.

(56) References Cited

U.S. PATENT DOCUMENTS

| | | | |
|---|---|---|---|
| 4,363,963 A | 12/1982 | Ando | |
| 4,433,675 A | 2/1984 | Konoshima | |
| 4,436,095 A | 3/1984 | Kruger | |
| 4,473,839 A * | 9/1984 | Noda | H04N 9/735 |
| | | | 348/245 |
| 4,556,057 A * | 12/1985 | Hiruma | A61B 1/043 |
| | | | 600/431 |
| 4,644,403 A * | 2/1987 | Sakai | H04N 3/1543 |
| | | | 257/229 |
| 4,651,226 A * | 3/1987 | Motoori | H04N 1/4072 |
| | | | 250/229 |
| 4,692,606 A | 9/1987 | Sakai et al. | |
| 4,740,837 A * | 4/1988 | Yanagisawa | A61B 1/05 |
| | | | 348/211.99 |
| 4,741,327 A | 5/1988 | Yabe | |
| 4,742,388 A * | 5/1988 | Cooper | A61B 1/05 |
| | | | 348/223.1 |
| 4,745,471 A | 5/1988 | Takamura et al. | |
| 4,773,396 A | 9/1988 | Okazaki | |
| 4,782,386 A * | 11/1988 | Ams | A61B 1/042 |
| | | | 348/371 |
| 4,786,965 A | 11/1988 | Yabe | |
| 4,832,003 A | 5/1989 | Yabe | |
| 4,845,555 A | 7/1989 | Yabe et al. | |
| 4,853,772 A | 8/1989 | Kikuchi | |
| 4,853,773 A | 8/1989 | Hibino et al. | |
| 4,866,526 A | 9/1989 | Ams et al. | |
| 4,884,133 A | 11/1989 | Kanno et al. | |
| 4,884,134 A * | 11/1989 | Tsuji | A61B 1/05 |
| | | | 348/230.1 |
| 4,918,521 A | 5/1990 | Yabe et al. | |
| 4,924,856 A | 5/1990 | Noguchi | |
| 4,938,205 A | 7/1990 | Nudelman | |
| 4,942,473 A | 7/1990 | Zeevi et al. | |
| 4,947,246 A * | 8/1990 | Kikuchi | A61B 1/0638 |
| | | | 348/269 |
| 4,953,539 A * | 9/1990 | Nakamura | A61B 1/00177 |
| | | | 348/E5.029 |
| 4,959,710 A * | 9/1990 | Uehara | A61B 1/0638 |
| | | | 348/E5.038 |
| 5,001,556 A | 3/1991 | Nakamura et al. | |
| 5,016,975 A | 5/1991 | Sasaki et al. | |
| 5,021,888 A | 6/1991 | Kondou et al. | |
| 5,047,846 A * | 9/1991 | Uchiyama | G01N 21/6458 |
| | | | 348/510 |
| RE33,854 E | 3/1992 | Adair | |
| 5,103,497 A | 4/1992 | Hicks | |
| 5,111,804 A | 5/1992 | Funakoshi | |
| 5,133,035 A | 7/1992 | Hicks | |
| 5,187,572 A | 2/1993 | Nakamura et al. | |
| 5,188,094 A | 2/1993 | Adair | |
| 5,196,938 A | 3/1993 | Blessinger | |
| 5,200,838 A | 4/1993 | Nudelman et al. | |
| 5,220,198 A | 6/1993 | Tsuji | |
| 5,228,430 A | 7/1993 | Sakamoto | |
| 5,233,416 A * | 8/1993 | Inoue | A61B 1/0638 |
| | | | 348/269 |
| 5,241,170 A | 8/1993 | Field, Jr. et al. | |
| 5,264,925 A * | 11/1993 | Shipp | H04N 9/045 |
| | | | 348/269 |
| 5,313,306 A | 5/1994 | Kuban et al. | |
| 5,325,847 A | 7/1994 | Matsuno | |
| 5,402,768 A | 4/1995 | Adair | |
| 5,408,268 A * | 4/1995 | Shipp | H04N 5/2354 |
| | | | 348/269 |
| 5,411,020 A | 5/1995 | Ito | |
| 5,427,087 A | 6/1995 | Ito et al. | |
| 5,454,366 A | 10/1995 | Ito et al. | |
| 5,494,483 A | 2/1996 | Adair | |
| 5,523,786 A | 6/1996 | Parulski | |
| 5,550,595 A | 8/1996 | Hannah | |
| 5,594,497 A | 1/1997 | Ahern et al. | |
| 5,665,959 A | 9/1997 | Fossum et al. | |
| 5,704,836 A * | 1/1998 | Norton | A63F 13/06 |
| | | | 250/221 |
| 5,730,702 A | 3/1998 | Tanaka et al. | |
| 5,734,418 A | 3/1998 | Danna | |
| 5,748,234 A | 5/1998 | Lippincott | |
| 5,749,830 A * | 5/1998 | Kaneko | A61B 1/00082 |
| | | | 348/E5.038 |
| 5,754,313 A | 5/1998 | Pelchy et al. | |
| 5,783,909 A | 7/1998 | Hochstein | |
| 5,784,099 A | 7/1998 | Lippincott | |
| 5,857,963 A | 1/1999 | Pelchy et al. | |
| 5,887,049 A | 3/1999 | Fossum | |
| 5,929,901 A | 7/1999 | Adair et al. | |
| 5,949,483 A | 9/1999 | Fossum et al. | |
| 5,986,693 A | 11/1999 | Adair et al. | |
| 6,023,315 A | 2/2000 | Harrold et al. | |
| 6,038,067 A | 3/2000 | George | |
| 6,043,839 A | 3/2000 | Adair et al. | |
| 6,139,489 A | 10/2000 | Wampler et al. | |
| 6,142,930 A | 11/2000 | Ito et al. | |
| 6,166,768 A | 12/2000 | Fossum et al. | |
| 6,184,922 B1 * | 2/2001 | Saito | A61B 1/00048 |
| | | | 348/65 |
| 6,184,940 B1 | 2/2001 | Sano | |
| 6,215,517 B1 | 4/2001 | Takahashi et al. | |
| 6,222,175 B1 | 4/2001 | Krymski | |
| 6,239,456 B1 | 5/2001 | Berezin et al. | |
| 6,272,269 B1 | 8/2001 | Naum | |
| 6,275,255 B1 | 8/2001 | Adair et al. | |
| 6,292,220 B1 * | 9/2001 | Ogawa | H04N 5/343 |
| | | | 348/296 |
| 6,294,775 B1 | 9/2001 | Seibel et al. | |
| 6,310,642 B1 | 10/2001 | Adair et al. | |
| 6,320,331 B1 | 11/2001 | Iida et al. | |
| 6,331,156 B1 | 12/2001 | Haefele et al. | |
| 6,389,205 B1 | 5/2002 | Muckner et al. | |
| 6,416,463 B1 | 7/2002 | Tsuzuki et al. | |
| 6,429,953 B1 | 8/2002 | Feng | |
| 6,444,970 B1 | 9/2002 | Barbato | |
| 6,445,022 B1 * | 9/2002 | Barna | H01L 27/14609 |
| | | | 250/370.08 |
| 6,445,139 B1 | 9/2002 | Marshall et al. | |
| 6,464,633 B1 | 10/2002 | Hosoda et al. | |
| 6,466,618 B1 | 10/2002 | Messing et al. | |
| 6,485,414 B1 | 11/2002 | Neuberger | |
| 6,512,280 B2 | 1/2003 | Chen et al. | |
| 6,627,474 B2 | 9/2003 | Barna et al. | |
| 6,631,230 B1 | 10/2003 | Campbell | |
| 6,659,940 B2 | 12/2003 | Adler | |
| 6,665,013 B1 | 12/2003 | Fossum et al. | |
| 6,677,992 B1 | 1/2004 | Matsumoto et al. | |
| 6,690,466 B2 | 2/2004 | Miller et al. | |
| 6,692,431 B2 | 2/2004 | Kazakevich | |
| 6,707,499 B1 * | 3/2004 | Kung | H01L 27/14831 |
| | | | 250/208.1 |
| 6,772,181 B1 | 8/2004 | Fu et al. | |
| 6,773,392 B2 | 8/2004 | Kikuchi et al. | |
| 6,791,739 B2 | 9/2004 | Ramanujan et al. | |
| 6,796,939 B1 | 9/2004 | Hirata et al. | |
| 6,799,065 B1 | 9/2004 | Niemeyer | |
| 6,809,358 B2 | 10/2004 | Hsieh et al. | |
| 6,838,653 B2 | 1/2005 | Campbell et al. | |
| 6,841,947 B2 | 1/2005 | Berg-johansen | |
| 6,847,399 B1 | 1/2005 | Ang | |
| 6,856,712 B2 | 2/2005 | Fauver et al. | |
| 6,873,363 B1 | 3/2005 | Barna et al. | |
| 6,879,340 B1 | 4/2005 | Chevallier | |
| 6,899,675 B2 | 5/2005 | Cline et al. | |
| 6,900,829 B1 | 5/2005 | Ozawa et al. | |
| 6,906,745 B1 | 6/2005 | Fossum et al. | |
| 6,921,920 B2 | 7/2005 | Kazakevich | |

(56) References Cited

U.S. PATENT DOCUMENTS

| | | |
|---|---|---|
| 6,933,974 B2 | 8/2005 | Lee |
| 6,947,090 B2 | 9/2005 | Komoro et al. |
| 6,961,461 B2 | 11/2005 | MacKinnon et al. |
| 6,970,195 B1 | 11/2005 | Bidermann et al. |
| 6,977,733 B2 | 12/2005 | Denk et al. |
| 6,982,740 B2 | 1/2006 | Adair et al. |
| 6,999,118 B2 | 2/2006 | Suzuki |
| 7,009,634 B2 | 3/2006 | Iddan et al. |
| 7,009,648 B2 | 3/2006 | Lauxtermann et al. |
| 7,030,904 B2 | 4/2006 | Adair et al. |
| 7,037,259 B2 | 5/2006 | Hakamata et al. |
| 7,068,878 B2 | 6/2006 | Crossman-Bosworth et al. |
| 7,071,979 B1* | 7/2006 | Ohtani ............... H04N 1/484 235/462.42 |
| 7,079,178 B2 | 7/2006 | Hynecek |
| 7,102,682 B2 | 9/2006 | Baer |
| 7,105,371 B2 | 9/2006 | Fossum et al. |
| 7,106,377 B2 | 9/2006 | Bean et al. |
| 7,119,839 B1 | 10/2006 | Mansoorian |
| 7,151,568 B2* | 12/2006 | Kawachi ............. G01B 11/002 348/241 |
| 7,159,782 B2 | 1/2007 | Johnston et al. |
| 7,184,084 B2 | 2/2007 | Glenn |
| 7,189,226 B2 | 3/2007 | Auld et al. |
| 7,189,961 B2 | 3/2007 | Johnston et al. |
| 7,208,983 B2 | 4/2007 | Imaizumi et al. |
| 7,252,236 B2 | 8/2007 | Johnston et al. |
| 7,258,663 B2 | 8/2007 | Doguchi et al. |
| 7,261,687 B2 | 8/2007 | Yang |
| 7,280,139 B2 | 10/2007 | Pahr et al. |
| 7,298,938 B2 | 11/2007 | Johnston |
| 7,312,879 B2 | 12/2007 | Johnston |
| 7,319,478 B2 | 1/2008 | Dolt et al. |
| 7,355,155 B2 | 4/2008 | Wang |
| 7,356,198 B2 | 4/2008 | Chauville et al. |
| 7,365,768 B1 | 4/2008 | Ono et al. |
| 7,369,140 B1 | 5/2008 | King et al. |
| 7,369,176 B2 | 5/2008 | Sonnenschein et al. |
| 7,455,638 B2 | 11/2008 | Ogawa et al. |
| 7,470,229 B2 | 12/2008 | Ogawa et al. |
| 7,476,197 B2 | 1/2009 | Wiklof et al. |
| 7,532,760 B2 | 5/2009 | Kaplinsky et al. |
| 7,540,645 B2 | 6/2009 | Kazakevich |
| 7,544,163 B2 | 6/2009 | MacKinnon et al. |
| 7,545,434 B2 | 6/2009 | Bean et al. |
| 7,564,935 B2 | 7/2009 | Suzuki |
| 7,567,291 B2 | 7/2009 | Bechtel et al. |
| 7,573,516 B2 | 8/2009 | Krymski et al. |
| 7,573,519 B2 | 8/2009 | Phan et al. |
| 7,583,872 B2 | 9/2009 | Seibel et al. |
| 7,616,238 B2* | 11/2009 | Avni ................... A61B 1/041 348/243 |
| 7,630,008 B2 | 12/2009 | Sarwari |
| 7,744,528 B2 | 6/2010 | Wallace et al. |
| 7,783,133 B2 | 8/2010 | Dunki-Jacobs et al. |
| 7,784,697 B2 | 8/2010 | Johnston et al. |
| 7,791,009 B2 | 9/2010 | Johnston et al. |
| 7,792,378 B2 | 9/2010 | Liege et al. |
| 7,794,394 B2 | 9/2010 | Frangioni |
| 7,813,538 B2 | 10/2010 | Carroll et al. |
| 7,914,447 B2 | 3/2011 | Kanai |
| 7,916,193 B2 | 3/2011 | Fossum |
| 7,935,050 B2 | 5/2011 | Luanava et al. |
| 7,944,566 B2 | 5/2011 | Xie |
| 7,969,097 B2 | 6/2011 | Van De Ven |
| 7,995,123 B2 | 8/2011 | Lee et al. |
| 8,040,394 B2 | 10/2011 | Fossum et al. |
| 8,054,339 B2 | 11/2011 | Fossum et al. |
| 8,059,174 B2 | 11/2011 | Mann et al. |
| 8,100,826 B2 | 1/2012 | MacKinnon et al. |
| 8,159,584 B2 | 4/2012 | Iwabuchi et al. |
| 8,193,542 B2 | 6/2012 | Maehara |
| 8,212,884 B2 | 7/2012 | Seibel et al. |
| 8,231,522 B2* | 7/2012 | Endo ................... A61B 1/0005 600/109 |
| 8,300,111 B2 | 10/2012 | Iwane |
| 8,372,003 B2 | 2/2013 | St. George et al. |
| 8,382,662 B2 | 2/2013 | Soper et al. |
| 8,396,535 B2 | 3/2013 | Wang et al. |
| 8,423,110 B2 | 4/2013 | Barbato et al. |
| 8,471,938 B2 | 6/2013 | Altice, Jr. et al. |
| 8,476,575 B2 | 7/2013 | Mokhnatyuk |
| 8,482,823 B2 | 7/2013 | Cheng |
| 8,493,474 B2 | 7/2013 | Richardson |
| 8,493,564 B2 | 7/2013 | Brukilacchio et al. |
| 8,523,367 B2 | 9/2013 | Ogura |
| 8,537,203 B2 | 9/2013 | Seibel et al. |
| 8,559,743 B2 | 10/2013 | Liege et al. |
| 8,582,011 B2 | 11/2013 | Dosluoglu |
| 8,602,971 B2 | 12/2013 | Farr |
| 8,605,177 B2 | 12/2013 | Rossi et al. |
| 8,610,808 B2 | 12/2013 | Prescher et al. |
| 8,614,754 B2 | 12/2013 | Fossum |
| 8,625,016 B2 | 1/2014 | Fossum et al. |
| 8,638,847 B2 | 1/2014 | Wang |
| 8,648,287 B1 | 2/2014 | Fossum |
| 8,649,848 B2 | 2/2014 | Crane et al. |
| 8,668,339 B2 | 3/2014 | Kabuki et al. |
| 8,675,125 B2 | 3/2014 | Cossairt et al. |
| 8,698,887 B2 | 4/2014 | Makino et al. |
| 8,836,834 B2 | 9/2014 | Hashimoto et al. |
| 8,848,063 B2 | 9/2014 | Jo et al. |
| 8,858,425 B2 | 10/2014 | Farr et al. |
| 8,885,034 B2 | 11/2014 | Adair et al. |
| 9,509,917 B2 | 11/2016 | Blanquart et al. |
| 9,516,239 B2 | 12/2016 | Blanquart et al. |
| 2001/0017649 A1* | 8/2001 | Yaron ................. A61B 1/00193 348/45 |
| 2001/0030744 A1 | 10/2001 | Chang |
| 2001/0055462 A1 | 10/2001 | Seibel |
| 2002/0054219 A1 | 5/2002 | Jaspers |
| 2002/0064341 A1 | 5/2002 | Fauver et al. |
| 2002/0080248 A1 | 6/2002 | Adair et al. |
| 2002/0080359 A1 | 6/2002 | Denk et al. |
| 2002/0140844 A1* | 10/2002 | Kurokawa ........... H04N 5/2176 348/362 |
| 2002/0158976 A1 | 10/2002 | Vni et al. |
| 2002/0158986 A1 | 10/2002 | Baer |
| 2003/0007087 A1 | 1/2003 | Hakamata et al. |
| 2003/0007686 A1 | 1/2003 | Roever |
| 2003/0107664 A1 | 6/2003 | Suzuki |
| 2003/0189663 A1 | 10/2003 | Dolt et al. |
| 2004/0082833 A1 | 4/2004 | Adler et al. |
| 2004/0170712 A1 | 9/2004 | Sadek El Mogy |
| 2005/0009982 A1 | 1/2005 | Inagaki et al. |
| 2005/0027164 A1 | 2/2005 | Barbato et al. |
| 2005/0038322 A1 | 2/2005 | Banik |
| 2005/0113641 A1* | 5/2005 | Bala .................... A61B 1/045 600/108 |
| 2005/0122530 A1 | 6/2005 | Denk et al. |
| 2005/0151866 A1 | 7/2005 | Ando et al. |
| 2005/0200291 A1 | 9/2005 | Naugler, Jr. et al. |
| 2005/0234302 A1 | 10/2005 | MacKinnon et al. |
| 2005/0237384 A1 | 10/2005 | Jess et al. |
| 2005/0261552 A1* | 11/2005 | Mori .................. A61B 1/00036 600/118 |
| 2005/0288546 A1 | 12/2005 | Sonnenschein et al. |
| 2006/0069314 A1 | 3/2006 | Farr |
| 2006/0087841 A1 | 4/2006 | Chern et al. |
| 2006/0197664 A1 | 9/2006 | Zhang et al. |
| 2006/0202036 A1 | 9/2006 | Wang et al. |
| 2006/0221250 A1 | 10/2006 | Rossbach et al. |
| 2006/0226231 A1 | 10/2006 | Johnston et al. |
| 2006/0264734 A1* | 11/2006 | Kimoto ............... A61B 1/00016 600/407 |
| 2006/0274335 A1 | 12/2006 | Wittenstein |
| 2007/0010712 A1 | 1/2007 | Negishi |
| 2007/0041448 A1 | 2/2007 | Miller et al. |
| 2007/0083085 A1 | 4/2007 | Birnkrant et al. |
| 2007/0129601 A1 | 6/2007 | Johnston et al. |
| 2007/0147033 A1 | 6/2007 | Ogawa et al. |
| 2007/0244364 A1 | 10/2007 | Luanava et al. |
| 2007/0244365 A1 | 10/2007 | Wiklof |
| 2007/0276187 A1 | 11/2007 | Wiklof et al. |

(56) References Cited

U.S. PATENT DOCUMENTS

| | | | |
|---|---|---|---|
| 2007/0279486 A1* | 12/2007 | Bayer | A61B 1/0005 348/65 |
| 2007/0285526 A1 | 12/2007 | Mann et al. | |
| 2008/0045800 A2 | 2/2008 | Farr | |
| 2008/0049132 A1* | 2/2008 | Suzuki | H04N 5/23293 348/308 |
| 2008/0088719 A1 | 4/2008 | Jacob et al. | |
| 2008/0107333 A1 | 5/2008 | Mazinani et al. | |
| 2008/0136953 A1 | 6/2008 | Barnea et al. | |
| 2008/0158348 A1 | 7/2008 | Karpen et al. | |
| 2008/0165360 A1 | 7/2008 | Johnston | |
| 2008/0192131 A1 | 8/2008 | Kim et al. | |
| 2008/0218598 A1 | 9/2008 | Harada et al. | |
| 2008/0218615 A1* | 9/2008 | Huang | H04N 5/2176 348/294 |
| 2008/0218824 A1 | 9/2008 | Johnston et al. | |
| 2008/0249369 A1 | 10/2008 | Seibel et al. | |
| 2009/0012361 A1 | 1/2009 | MacKinnon et al. | |
| 2009/0012368 A1 | 1/2009 | Banik | |
| 2009/0021588 A1 | 1/2009 | Border et al. | |
| 2009/0024000 A1 | 1/2009 | Chen | |
| 2009/0028465 A1 | 1/2009 | Pan | |
| 2009/0074265 A1 | 3/2009 | Huang et al. | |
| 2009/0091645 A1 | 4/2009 | Trimeche et al. | |
| 2009/0137893 A1 | 5/2009 | Seibel et al. | |
| 2009/0147077 A1 | 6/2009 | Tani et al. | |
| 2009/0154886 A1 | 6/2009 | Lewis et al. | |
| 2009/0160976 A1 | 6/2009 | Chen et al. | |
| 2009/0189530 A1 | 7/2009 | Ashdown et al. | |
| 2009/0208143 A1 | 8/2009 | Yoon et al. | |
| 2009/0227847 A1 | 9/2009 | Tepper et al. | |
| 2009/0232213 A1 | 9/2009 | Jia | |
| 2009/0259102 A1 | 10/2009 | Koninckx et al. | |
| 2009/0268063 A1 | 10/2009 | Ellis-Monaghan et al. | |
| 2009/0292168 A1 | 11/2009 | Farr | |
| 2009/0309500 A1 | 12/2009 | Reisch | |
| 2009/0316116 A1 | 12/2009 | Melville et al. | |
| 2009/0322912 A1* | 12/2009 | Blanquart | H04N 5/353 348/241 |
| 2010/0026722 A1 | 2/2010 | Kondo | |
| 2010/0049180 A1 | 2/2010 | Wells et al. | |
| 2010/0069713 A1* | 3/2010 | Endo | A61B 1/0005 600/109 |
| 2010/0102199 A1 | 4/2010 | Negley et al. | |
| 2010/0121142 A1 | 5/2010 | OuYang et al. | |
| 2010/0121143 A1 | 5/2010 | Sugimoto et al. | |
| 2010/0123775 A1 | 5/2010 | Shibasaki | |
| 2010/0134608 A1 | 6/2010 | Shibasaki | |
| 2010/0134662 A1 | 6/2010 | Bub | |
| 2010/0135398 A1 | 6/2010 | Wittmann et al. | |
| 2010/0137684 A1 | 6/2010 | Shibasaki et al. | |
| 2010/0149421 A1 | 6/2010 | Lin et al. | |
| 2010/0157037 A1 | 6/2010 | Iketani et al. | |
| 2010/0157039 A1 | 6/2010 | Sugai | |
| 2010/0165087 A1 | 7/2010 | Corso et al. | |
| 2010/0171429 A1 | 7/2010 | Garcia et al. | |
| 2010/0182446 A1 | 7/2010 | Matsubayashi | |
| 2010/0198009 A1 | 8/2010 | Farr et al. | |
| 2010/0198134 A1* | 8/2010 | Eckhouse | A45D 26/00 604/20 |
| 2010/0201797 A1 | 8/2010 | Shizukuishi et al. | |
| 2010/0228089 A1 | 9/2010 | Hoffman et al. | |
| 2010/0261961 A1 | 10/2010 | Scott et al. | |
| 2010/0274082 A1 | 10/2010 | Iguchi et al. | |
| 2010/0274090 A1 | 10/2010 | Ozaki et al. | |
| 2010/0305406 A1 | 12/2010 | Braun et al. | |
| 2010/0309333 A1 | 12/2010 | Smith et al. | |
| 2011/0028790 A1* | 2/2011 | Farr | A61B 1/00052 600/187 |
| 2011/0063483 A1 | 3/2011 | Rossi et al. | |
| 2011/0122301 A1 | 5/2011 | Yamura et al. | |
| 2011/0149358 A1 | 6/2011 | Cheng | |
| 2011/0181709 A1 | 7/2011 | Wright et al. | |
| 2011/0181840 A1 | 7/2011 | Cobb | |
| 2011/0184239 A1 | 7/2011 | Wright et al. | |
| 2011/0184243 A1 | 7/2011 | Wright et al. | |
| 2011/0208004 A1 | 8/2011 | Feingold et al. | |
| 2011/0212649 A1 | 9/2011 | Stokoe et al. | |
| 2011/0237882 A1 | 9/2011 | Saito | |
| 2011/0237884 A1 | 9/2011 | Saito | |
| 2011/0245605 A1 | 10/2011 | Jacobsen et al. | |
| 2011/0245616 A1 | 10/2011 | Kobayashi | |
| 2011/0255844 A1 | 10/2011 | Wu et al. | |
| 2011/0274175 A1 | 11/2011 | Sumitomo | |
| 2011/0279679 A1 | 11/2011 | Samuel et al. | |
| 2011/0288374 A1 | 11/2011 | Hadani et al. | |
| 2011/0292258 A1 | 12/2011 | Adler et al. | |
| 2011/0295061 A1 | 12/2011 | Haramaty et al. | |
| 2012/0004508 A1 | 1/2012 | McDowall et al. | |
| 2012/0014563 A1 | 1/2012 | Bendall | |
| 2012/0029279 A1 | 2/2012 | Kucklick | |
| 2012/0033118 A1 | 2/2012 | Lee et al. | |
| 2012/0041267 A1 | 2/2012 | Benning et al. | |
| 2012/0041534 A1 | 2/2012 | Clerc et al. | |
| 2012/0050592 A1 | 3/2012 | Oguma | |
| 2012/0078052 A1 | 3/2012 | Cheng | |
| 2012/0098933 A1 | 4/2012 | Robinson et al. | |
| 2012/0104230 A1 | 5/2012 | Eismann et al. | |
| 2012/0113506 A1 | 5/2012 | Gmitro et al. | |
| 2012/0120282 A1 | 5/2012 | Goris | |
| 2012/0140302 A1 | 6/2012 | Xie et al. | |
| 2012/0155761 A1 | 6/2012 | Matsuoka | |
| 2012/0157774 A1* | 6/2012 | Kaku | A61B 1/0005 600/178 |
| 2012/0194686 A1 | 8/2012 | Lin et al. | |
| 2012/0197080 A1 | 8/2012 | Murayama | |
| 2012/0242975 A1 | 9/2012 | Min et al. | |
| 2012/0262621 A1 | 10/2012 | Sato et al. | |
| 2012/0281111 A1 | 11/2012 | Jo et al. | |
| 2013/0018256 A1 | 1/2013 | Kislev et al. | |
| 2013/0035545 A1* | 2/2013 | Ono | A61B 1/045 600/109 |
| 2013/0053642 A1 | 2/2013 | Mizuyoshi et al. | |
| 2013/0070071 A1* | 3/2013 | Peltie | A61B 1/05 348/68 |
| 2013/0126708 A1 | 5/2013 | Blanquart | |
| 2013/0127934 A1 | 5/2013 | Chiang | |
| 2013/0135589 A1 | 5/2013 | Curtis et al. | |
| 2013/0144120 A1 | 6/2013 | Yamazaki | |
| 2013/0155215 A1 | 6/2013 | Shimada et al. | |
| 2013/0155305 A1 | 6/2013 | Shintani | |
| 2013/0158346 A1 | 6/2013 | Soper et al. | |
| 2013/0184524 A1 | 7/2013 | Shimada et al. | |
| 2013/0211217 A1 | 8/2013 | Yamaguchi et al. | |
| 2013/0242069 A1 | 9/2013 | Kobayashi | |
| 2013/0244453 A1 | 9/2013 | Sakamoto | |
| 2013/0274597 A1 | 10/2013 | Byrne et al. | |
| 2013/0296652 A1 | 11/2013 | Farr | |
| 2013/0308837 A1 | 11/2013 | DiCarlo et al. | |
| 2013/0342690 A1 | 12/2013 | Williams et al. | |
| 2014/0005532 A1 | 1/2014 | Choi et al. | |
| 2014/0022365 A1 | 1/2014 | Yoshino | |
| 2014/0031623 A1 | 1/2014 | Kagaya | |
| 2014/0052004 A1 | 2/2014 | D'Alfonso et al. | |
| 2014/0073852 A1 | 3/2014 | Banik et al. | |
| 2014/0073853 A1 | 3/2014 | Swisher et al. | |
| 2014/0078278 A1 | 3/2014 | Lei | |
| 2014/0088363 A1 | 3/2014 | Sakai et al. | |
| 2014/0104466 A1 | 4/2014 | Fossum | |
| 2014/0160318 A1 | 6/2014 | Blanquart et al. | |
| 2014/0198249 A1* | 7/2014 | Tanaka | H04N 5/2354 348/370 |
| 2014/0203084 A1 | 7/2014 | Wang | |
| 2014/0267655 A1 | 9/2014 | Richardson et al. | |
| 2014/0267851 A1 | 9/2014 | Rhoads | |
| 2014/0268860 A1 | 9/2014 | Talbert et al. | |
| 2014/0275764 A1* | 9/2014 | Shen | A61B 1/0661 600/103 |
| 2014/0288365 A1 | 9/2014 | Henley et al. | |
| 2014/0300698 A1 | 10/2014 | Wany | |
| 2014/0316199 A1 | 10/2014 | Kucklick | |
| 2014/0354788 A1 | 12/2014 | Yano | |

(56) References Cited

U.S. PATENT DOCUMENTS

2014/0364689 A1    12/2014   Adair et al.
2016/0183775 A1    6/2016   Blanquart et al.
2017/0085853 A1    3/2017   Blanquart et al.

FOREIGN PATENT DOCUMENTS

| | | |
|---|---|---|
| CN | 101449575 A | 6/2009 |
| CN | 101755448 A | 6/2010 |
| CN | 102469932 A | 5/2012 |
| EP | 0660616 A2 | 6/1995 |
| EP | 1079255 A2 | 2/2001 |
| EP | 1637062 A1 | 3/2006 |
| EP | 1712177 A1 | 10/2006 |
| EP | 1819151 A1 | 8/2007 |
| EP | 2359739 A1 | 8/2011 |
| EP | 2371268 A1 | 10/2011 |
| JP | 2001308531 | 11/2001 |
| JP | 2002020816 A | 1/2002 |
| JP | 2007029746 A | 2/2007 |
| JP | 2007240931 A | 9/2007 |
| JP | 2009537283 A | 10/2009 |
| JP | 2010068992 A | 4/2010 |
| JP | 2010125284 A | 6/2010 |
| JP | 2011055327 A | 3/2011 |
| JP | 2012000160 A | 1/2016 |
| WO | 9605693 | 2/1996 |
| WO | WO2009120228 A1 | 10/2009 |
| WO | 2012043771 A1 | 4/2012 |

\* cited by examiner

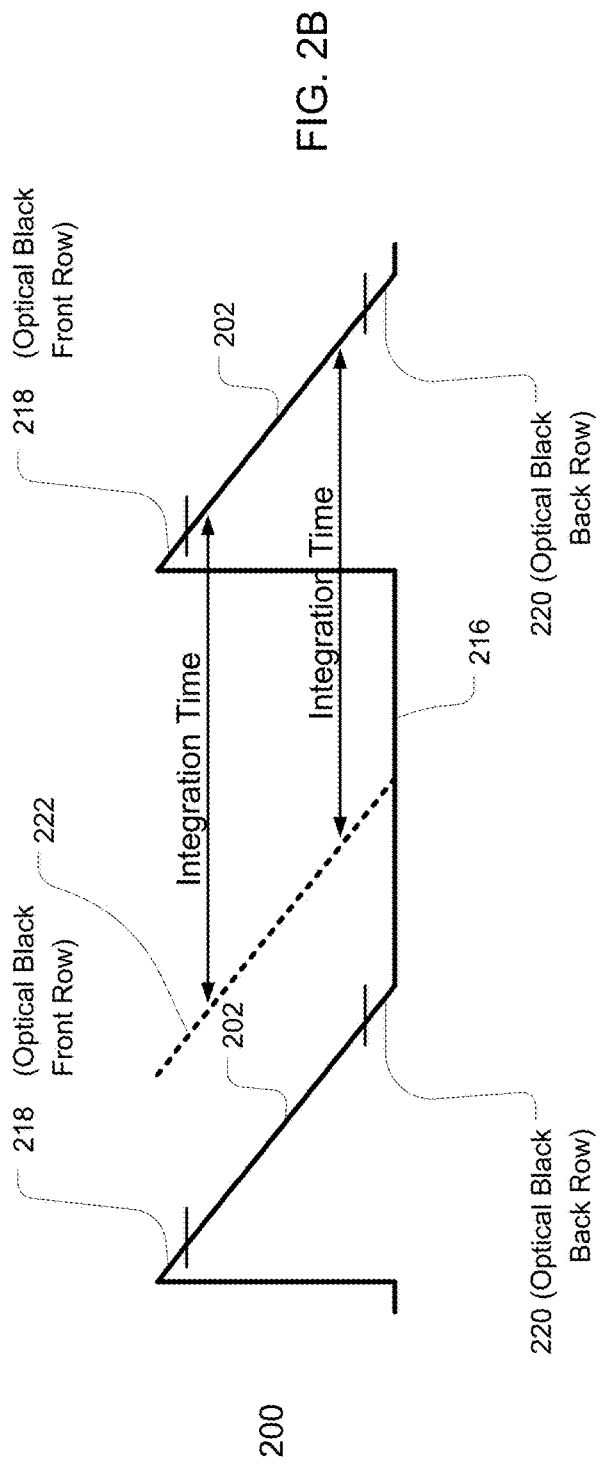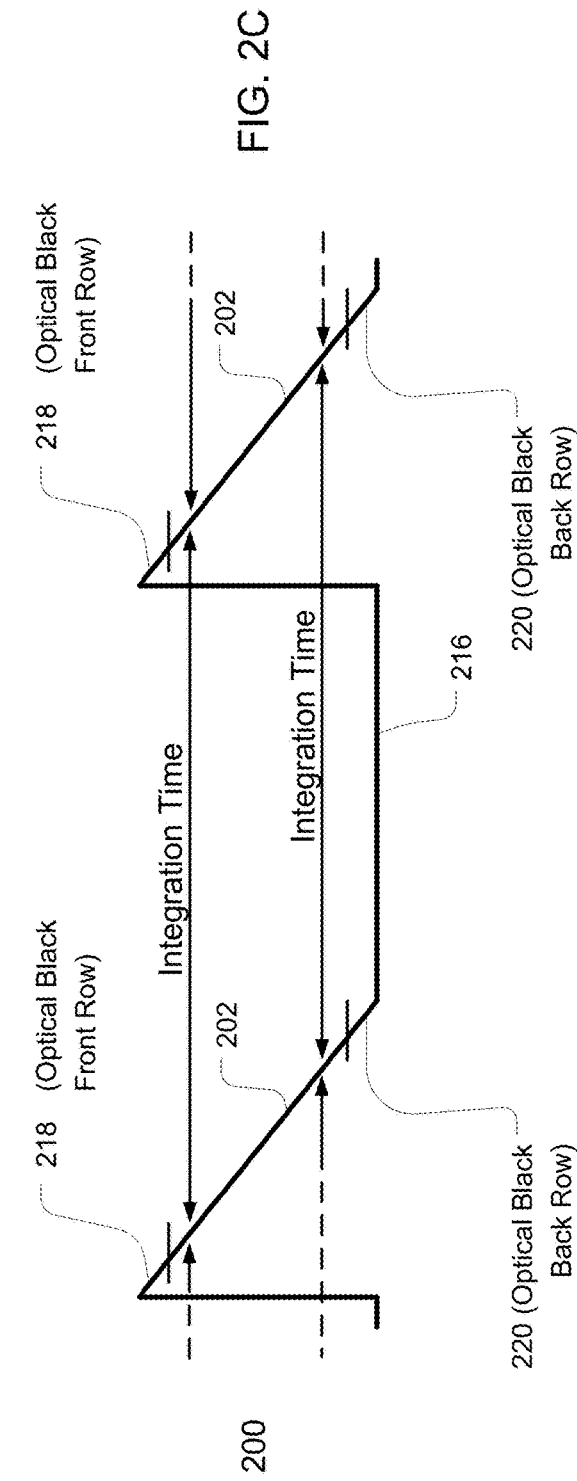

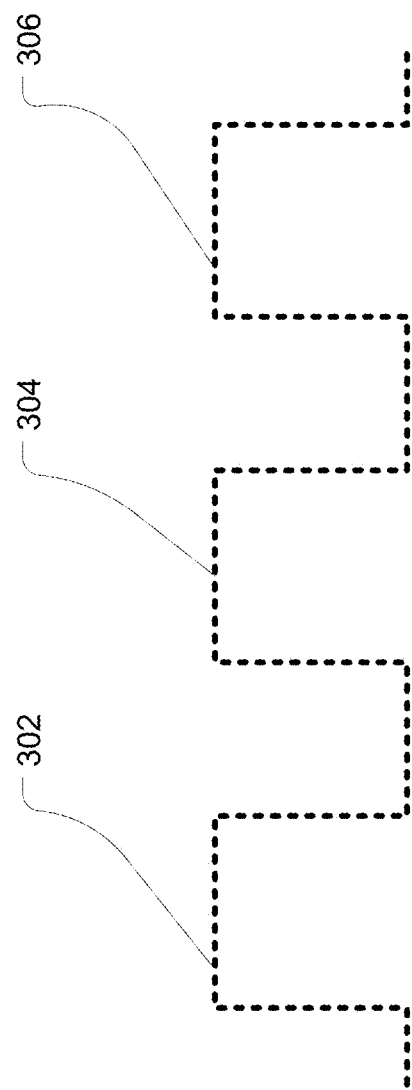

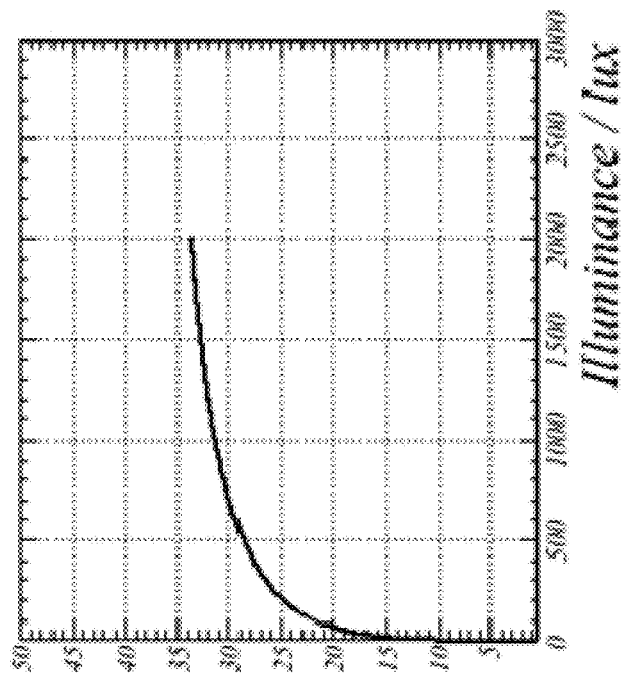
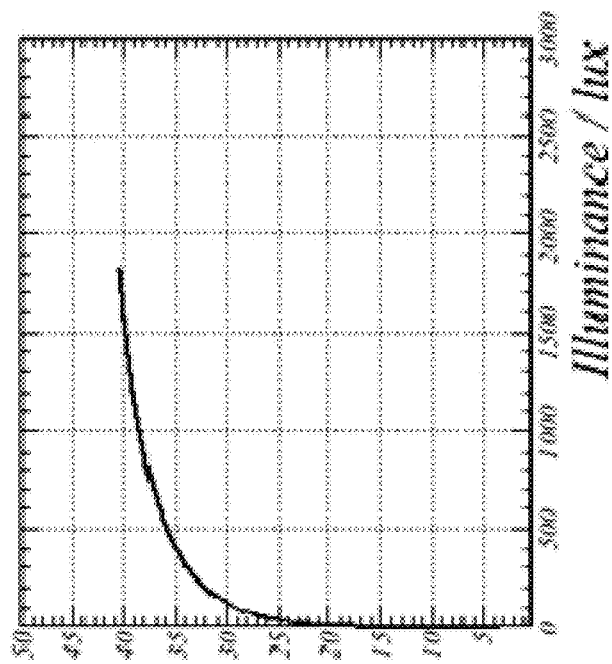
FIG. 24

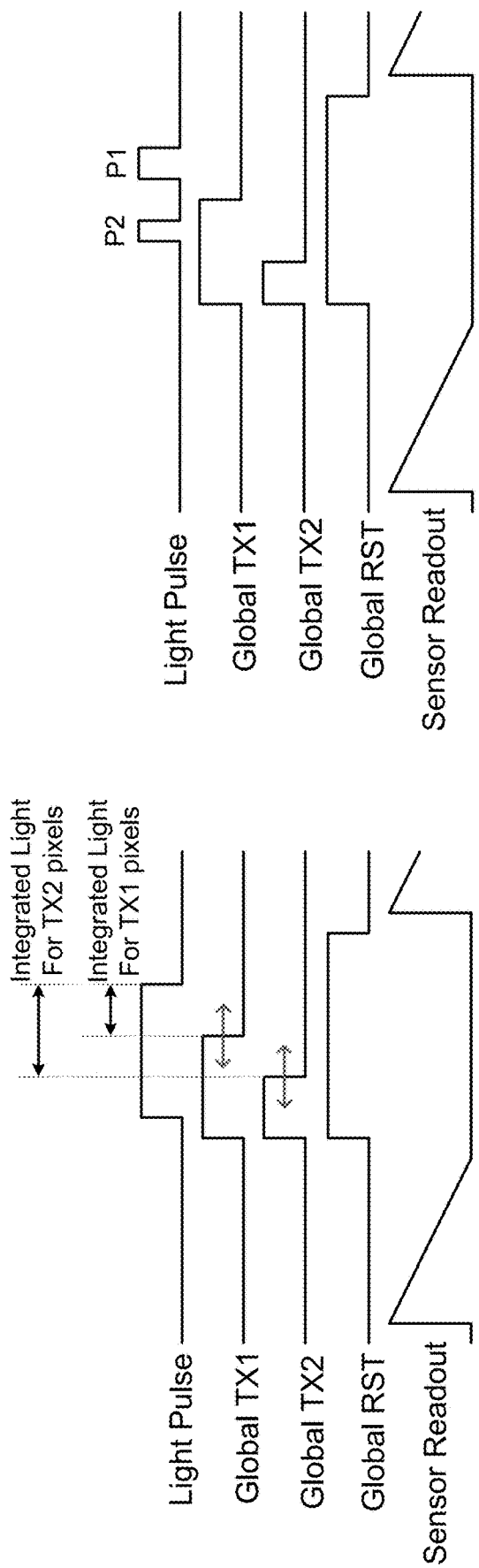

3D with double pixel array

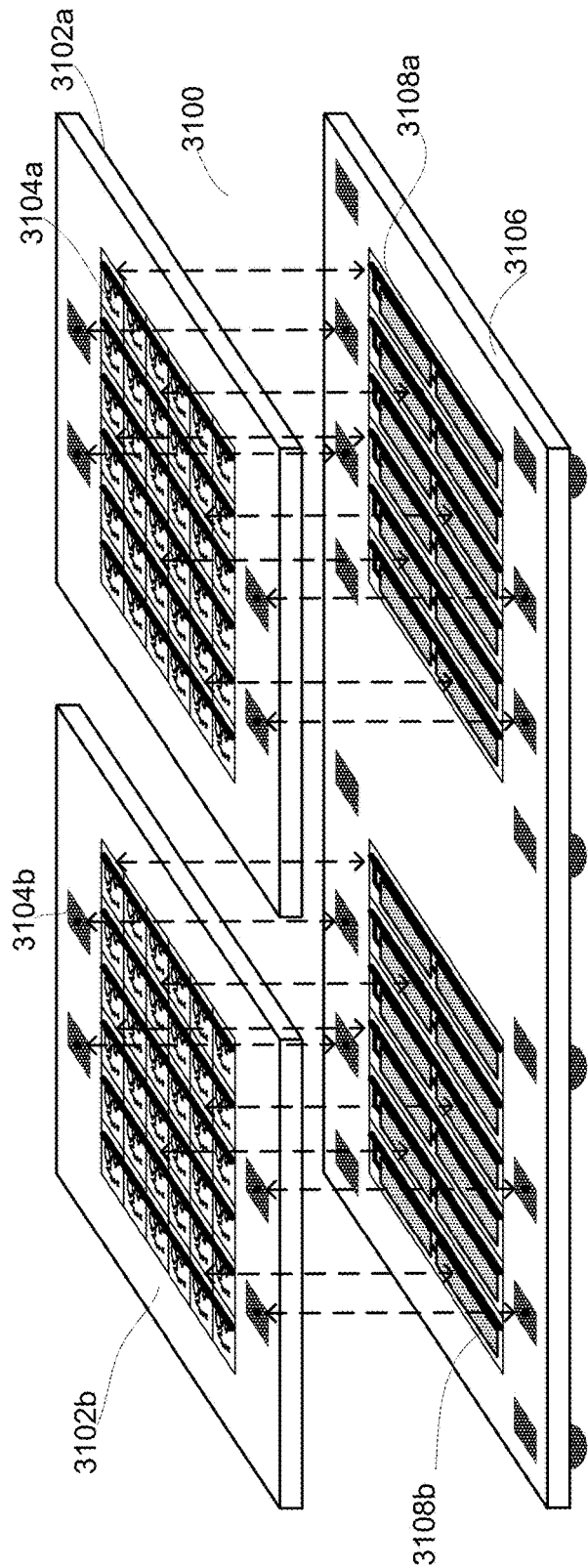
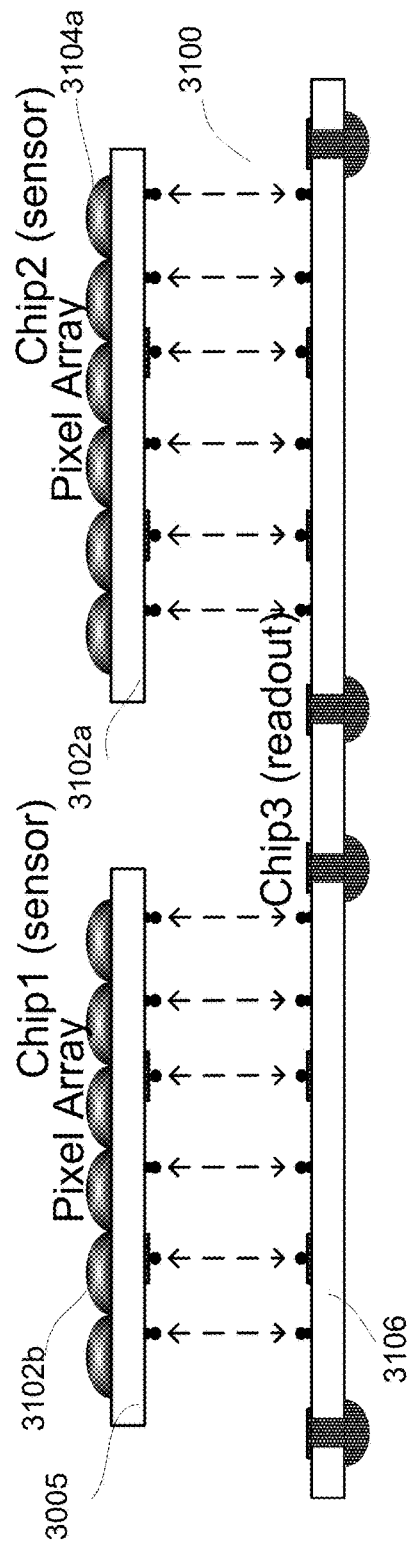
FIG. 31A
FIG. 31B

CONTINUOUS VIDEO IN A LIGHT DEFICIENT ENVIRONMENT

CROSS-REFERENCE TO RELATED APPLICATIONS

This application claims the benefit of U.S. Provisional Patent Application No. 61/676,289, filed on Jul. 26, 2012, and U.S. Provisional Patent Application No. 61/790,487, filed on Mar. 15, 2013, which are hereby incorporated by reference herein in their entireties, including but not limited to those portions that specifically appear hereinafter, the incorporation by reference being made with the following exception: In the event that any portion of the above-referenced applications is inconsistent with this application, this application supersedes said above-referenced applications.

BACKGROUND

Advances in technology have provided advances in imaging capabilities for medical use. One area that has enjoyed some of the most beneficial advances is that of endoscopic surgical procedures because of the advances in the components that make up an endoscope.

The disclosure relates generally to electromagnetic sensing and sensors. The disclosure also relates to low energy electromagnetic input conditions as well as low energy electromagnetic throughput conditions. The disclosure relates more particularly, but not necessarily entirely, to a system for producing an image in light deficient environments and associated structures, methods and features, which may include controlling a light source through duration, intensity or both, pulsing a component controlled light source during the blanking time, maximizing the blanking time to allow optimum light, and maintaining color balance.

The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where:

FIGS. 2A to 2D are illustrations of the operational cycles of a sensor (e.g., a plurality of frames) used to construct one image frame in accordance with the principles and teachings of the disclosure;

FIG. 3 is a graphical representation of the operation of an embodiment of an electromagnetic emitter in accordance with the principles and teachings of the disclosure;

FIG. 24 illustrates the impact on signal to noise ratio of the color correction for a typical Bayer-based sensor compared with no color correction;

FIGS. 26-27B illustrate method and hardware schematics for increasing the dynamic range within a closed or limited light environment in accordance with the principles and teachings of the disclosure;

FIGS. 31A and 31B illustrate a perspective view and a side view, respectively, of an implementation of an imaging sensor having a plurality of pixel arrays for producing a three dimensional image, wherein the plurality of pixel arrays and the image sensor are built on a plurality of substrates.

DETAILED DESCRIPTION

Figure 1:
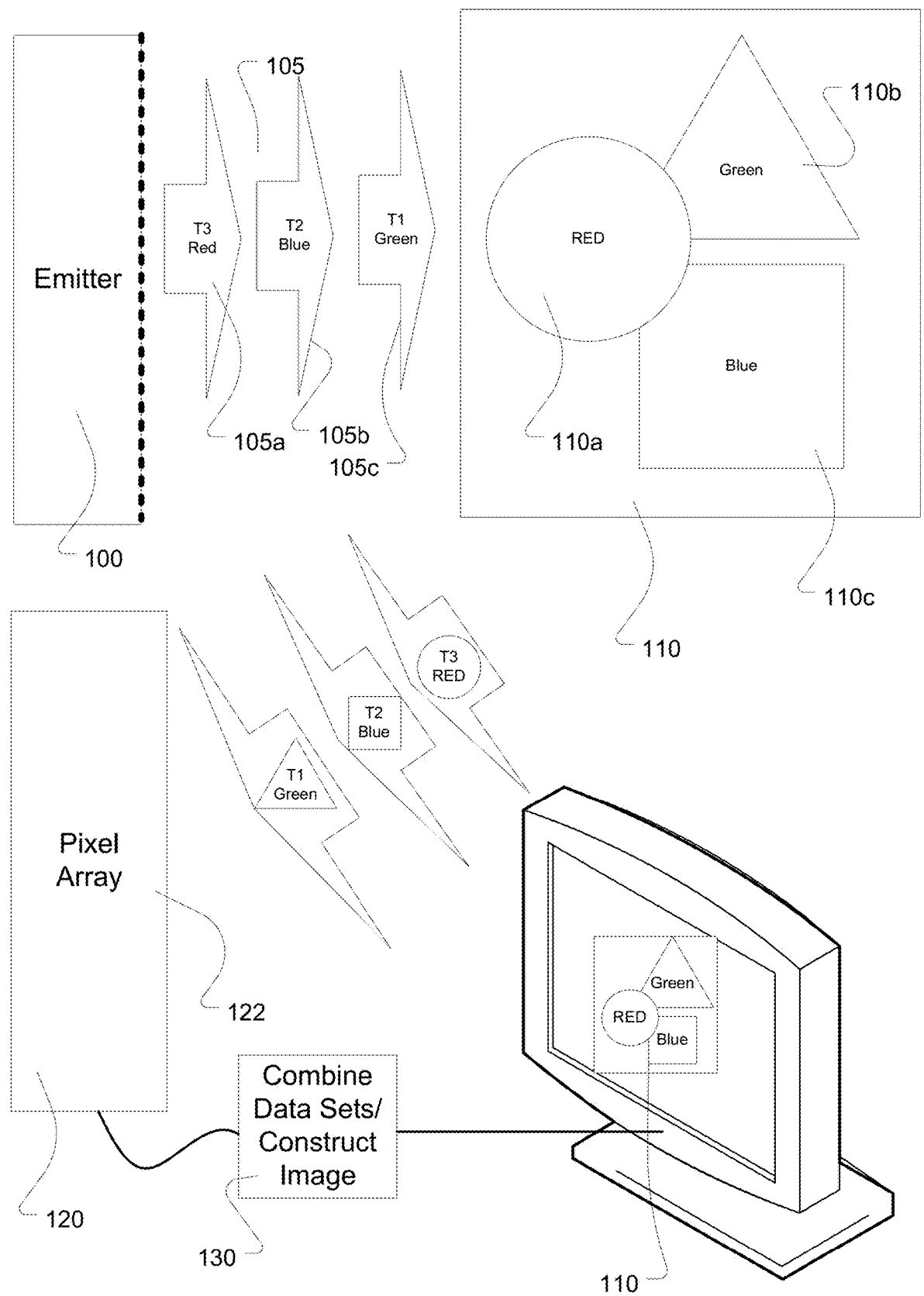
FIG. 1 is a schematic view of an embodiment of a system of a paired sensor and an electromagnetic emitter in operation for use in producing an image in a light deficient environment made in accordance with the principles and teachings of the disclosure.

The disclosure extends to methods, systems, and computer based products for digital imaging that may be primarily suited to medical applications. In the following description of the disclosure, reference is made to the accompanying drawings, which form a part hereof, and in which is shown by way of illustration specific implementations in which the disclosure may be practiced. It is understood that other implementations may be utilized and structural changes may be made without departing from the scope of the disclosure.

Conventional endoscopes, used in, for example, arthroscopy and laparoscopy, are designed such that the image sensors are typically placed within a hand-piece unit. In such a configuration, an endoscope unit must transmit the incident light along its length toward the sensor via a complex set of precisely coupled optical components, with minimal loss and distortion. The cost of the endoscope unit is dominated by the optics, since the components are expensive and the manufacturing process is labor intensive. Moreover, this type of scope is mechanically delicate and relatively minor impacts can easily damage the components or upset the relative alignments thereof, thereby causing extensive light fall off and rendering the scope unusable. This necessitates frequent, expensive repair cycles in order to maintain image quality. One solution to this issue is to place the image sensor within the endoscope itself at the distal end, thereby potentially approaching the optical simplicity, robustness and economy that is universally realized within, for example, mobile phone cameras. An acceptable solution to this approach is by no means trivial, however, as it introduces its own set of engineering challenges, not the least of which is the fact that the sensor must fit within an area that is highly confined, particularly in the X and Y dimensions, while there is more freedom in the Z dimension.

Placing aggressive constraints on sensor area naturally results in fewer and/or smaller pixels within a pixel array. Lowering the pixel count may directly affect the spatial resolution, while reducing the pixel area may reduce the available signal capacity and thereby the sensitivity of the pixel, as well as optimizing the number of pixels such that image quality is maximized, the minimum pixel resolution and native number of pixels using the maximum pixel quality and pitch, such that resolution is not an issue as well as lowering the signal to noise ratio (SNR) of each pixel. Lowering the signal capacity reduces the dynamic range, i.e., the ability of the imaging device or camera to simultaneously capture all of the useful information from scenes with large ranges of luminosity. There are various methods to extend the dynamic range of imaging systems beyond that of the pixel itself. All of them may have some kind of penalty, however, (e.g., in resolution or frame rate) and they can introduce undesirable artifacts, which become problematic in extreme cases. Reducing the sensitivity has the consequence that greater light power is required to bring the darker regions of the scene to acceptable signal levels. Lowering the F-number (enlarging the aperture) can compensate for a loss in sensitivity, but at the cost of spatial distortion and reduced depth of focus.

In the sensor industry, CMOS image sensors have largely displaced conventional CCD image sensors in modern camera applications, such as endoscopy, owing to their greater ease of integration and operation, superior or comparable image quality, greater versatility and lower cost. Typically, they may include the circuitry necessary to convert the image information into digital data and have various levels of digital processing incorporated thereafter. This can range from basic algorithms for the purpose of correcting non-idealities, which may, for example, arise from variations in amplifier behavior, to full image signal processing (ISP) chains, providing video data in the standard sRGB color space for example (cameras-on-chip).

If the control unit or second stage is remotely located with respect to and is an appreciable distance from the sensor, it may be desirable to transmit the data in the digital domain, since it is largely immune to interference noise and signal degradation, when compared to transmitting an analog data stream. It will be appreciated that various electrical digital signaling standards may be used, such as LVDS (low voltage differential signaling), sub-LVDS, SLVS (scalable low voltage signaling) or other electrical digital signaling standards.

There may be a strong desire to minimize the number of electrical conductors in order to reduce the number of pads consuming space on the sensor, and to reduce the complexity and cost of sensor manufacture. Although the addition of analog to digital conversion to the sensor may be advantageous, the additional area occupied by the conversion circuits is offset because of the significant reduction in the analog buffering power needed due to the early conversion to a digital signal.

In terms of area consumption, given the typical feature size available in CMOS image sensor (CIS) technologies, it may be preferable in some implementations to have all of the internal logic signals generated on the same chip as the pixel array via a set of control registers and a simple command interface.

Some implementations of the disclosure may include aspects of a combined sensor and system design that allows for high definition imaging with reduced pixel counts in a highly controlled illumination environment. This may be accomplished by virtue of frame by frame pulsing of a single color wavelength and switching or alternating each frame between a single, different color wavelength using a controlled light source in conjunction with high frame capture rates and a specially designed corresponding monochromatic sensor. As used herein monochramitc sensor refers to an unfiltered imaging sensor. Since the pixels are color agnostic, the effective spatial resolution is appreciably higher than for their color (typically Bayer-pattern filtered) counterparts in conventional single-sensor cameras. They may also have higher quantum efficiency since far fewer incident photons are wasted between the individual pixels. Moreover, Bayer based spatial color modulation requires that the modulation transfer function (MTF) of the accompanying optics be lowered compared with the monochrome modulation, in order to blur out the color artifacts associated with the Bayer pattern. This has a detrimental impact on the actual spatial resolution that can be realized with color sensors.

The disclosure is also concerned with a system solution for endoscopy applications in which the image sensor is resident at the distal end of the endoscope. In striving for a minimal area sensor based system, there are other design aspects that can be developed, beyond reduction in pixel count. The area of the digital portion of the chip may be minimized. In addition, the number of connections to the chip (pads) may also be minimized. The disclosure describes novel methods that accomplish these goals for the realization of such a system. This involves the design of a full-custom CMOS image sensor with several novel features.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the structure, systems and methods for producing an image in a light deficient environment are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "proximal" shall refer broadly to the concept of a portion nearest an origin.

As used herein, the term "distal" shall generally refer to the opposite of proximal, and thus to the concept of a portion farther from an origin, or a furthest portion, depending upon the context.

As used herein, color sensors or multi spectrum sensors are those sensors known to have a color filter array (CFA) thereon so as to filter the incoming electromagnetic radiation into its separate components. In the visual range of the electromagnetic spectrum, such a CFA may be built on a Bayer pattern or modification thereon in order to separate green, red and blue spectrum components of the light. Referring now to FIGS. 1-5, the systems and methods for producing an image in a light deficient environment will now be described. FIG. 1 illustrates a schematic view of a paired sensor and an electromagnetic emitter in operation for use in producing an image in a light deficient environment. Such a configuration allows for increased functionality in light controlled or ambient light deficient environments.

It should be noted that as used herein the term "light" is both a particle and a wavelength, and is intended to denote electromagnetic radiation that is detectable by a pixel array, and may include wavelengths from the visible and non-visible spectrums of electromagnetic radiation. The term "partition" is used herein to mean a predetermined range of wavelengths of the electromagnetic spectrum that is less than the entire spectrum, or in other words, wavelengths that make up some portion of the electromagnetic spectrum. As used herein, an emitter is a light source that may be controllable as to the portion of the electromagnetic spectrum that is emitted or that may operate as to the physics of its components, the intensity of the emissions, or the duration of the emission, or all of the above. An emitter may emit light in any dithered, diffused, or collimated emission and may be controlled digitally or through analog methods or systems. As used herein, an electromagnetic emitter is a source of a burst of electromagnetic energy and includes light sources, such as lasers, LEDs, incandescent light, or any light source that can be digitally controlled.

A pixel array of an image sensor may be paired with an emitter electronically, such that they are synced during operation for both receiving the emissions and for the adjustments made within the system. As can be seen in FIG. 1, an emitter 100 may be tuned to emit electromagnetic radiation in the form of a laser, which may be pulsed in order to illuminate an object 110. The emitter 100 may pulse at an interval that corresponds to the operation and functionality of a pixel array 122. The emitter 100 may pulse light in a plurality of electromagnetic partitions 105, such that the pixel array receives electromagnetic energy and produces a data set that corresponds (in time) with each specific electromagnetic partition 105. For example, FIG. 1 illustrates a system having a monochromatic sensor 120 having a pixel array (black and white) 122 and supporting circuitry, which pixel array 122 is sensitive to electromagnetic radiation of any wavelength. The light emitter 100 illustrated in the figure may be a laser emitter that is capable of emitting a red electromagnetic partition 105a, a blue electromagnetic partition 105b, and a green electromagnetic partition 105c in any desired sequence. It will be appreciated that other light emitters 100 may be used in FIG. 1 without departing from the scope of the disclosure, such as digital or analog based emitters.

During operation, the data created by the monochromatic sensor 120 for any individual pulse may be assigned a specific color partition, wherein the assignment is based on the timing of the pulsed color partition from the emitter 100. Even though the pixels 122 are not color dedicated they can be assigned a color for any given data set based on a priori information about the emitter.

In one embodiment, three data sets representing RED, GREEN and BLUE electromagnetic pulses may be individual frames combined to form a single image frame. It will be appreciated that the disclosure is not limited to any particular color combination or any particular electromagnetic partition, and that any color combination or any electromagnetic partition may be used in place of RED, GREEN and BLUE, such as Cyan, Magenta and Yellow; Ultraviolet; infra-red; any combination of the foregoing, or any other color combination, including all visible and non-visible wavelengths, without departing from the scope of the disclosure. In the figure, the object 110 to be imaged contains a red portion 110 a, green portion 110 b and a blue portion 110 c. As illustrated in the figure, the reflected light from the electromagnetic pulses only contains the data for the portion of the object having the specific color that corresponds to the pulsed color partition. Those separate color (or color interval) data sets can then be used to reconstruct the image by combining the data sets at 130.

Figure 2:
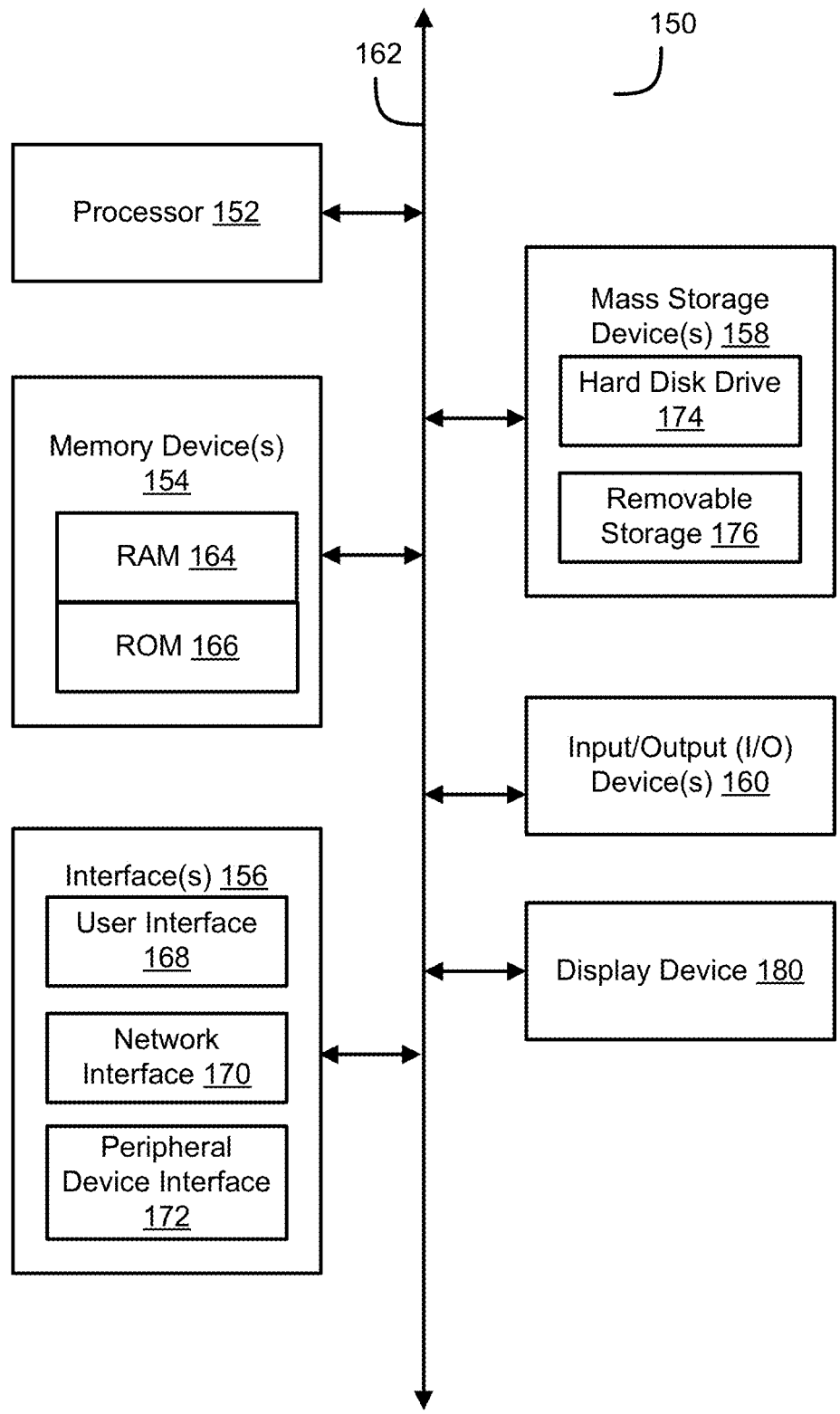
FIG. 2 is a schematic view of complementary system hardware.

As illustrated in FIG. 2, implementations of the present disclosure may comprise or utilize a special purpose or general-purpose computer, including computer hardware, such as, for example, one or more processors and system memory, as discussed in greater detail below. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. In an implementation, a sensor and camera control unit may be networked in order to communicate with each other, and other components, connected over the network to which they are connected. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures that can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered storage, such as FusionIO). Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, control units, camera control units, hand-held devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above mentioned computing devices may be provided by or located within a brick and mortar location. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

FIG. 2 is a block diagram illustrating an example computing device 150. Computing device 150 may be used to perform various procedures, such as those discussed herein. Computing device 150 can function as a server, a client, or any other computing entity. Computing device 150 can perform various monitoring functions as discussed herein, and can execute one or more application programs, such as the application programs described herein. Computing device 150 can be any of a wide variety of computing devices, such as a desktop computer, a notebook computer, a server computer, a handheld computer, camera control unit, tablet computer and the like.

Computing device 150 includes one or more processor(s) 152, one or more memory device(s) 154, one or more interface(s) 156, one or more mass storage device(s) 158, one or more Input/Output (I/O) device(s) 160, and a display device 180 all of which are coupled to a bus 162. Processor(s) 152 include one or more processors or controllers that execute instructions stored in memory device(s) 154 and/or mass storage device(s) 158. Processor(s) 152 may also include various types of computer-readable media, such as cache memory.

Memory device(s) 154 include various computer-readable media, such as volatile memory (e.g., random access memory (RAM) 164) and/or nonvolatile memory (e.g., read-only memory (ROM) 166). Memory device(s) 154 may also include rewritable ROM, such as Flash memory.

Mass storage device(s) 158 include various computer readable media, such as magnetic tapes, magnetic disks, optical disks, solid-state memory (e.g., Flash memory), and so forth. As shown in FIG. 2, a particular mass storage device is a hard disk drive 174. Various drives may also be included in mass storage device(s) 158 to enable reading from and/or writing to the various computer readable media. Mass storage device(s) 158 include removable media 176 and/or non-removable media.

I/O device(s) 160 include various devices that allow data and/or other information to be input to or retrieved from computing device 150. Example I/O device(s) 160 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 180 includes any type of device capable of displaying information to one or more users of computing device 150. Examples of display device 180 include a monitor, display terminal, video projection device, and the like.

Interface(s) 106 include various interfaces that allow computing device 150 to interact with other systems, devices, or computing environments. Example interface(s) 156 may include any number of different network interfaces 170, such as interfaces to local area networks (LANs), wide area networks (WANs), wireless networks, and the Internet. Other interface(s) include user interface 168 and peripheral device interface 172. The interface(s) 156 may also include one or more user interface elements 168. The interface(s) 156 may also include one or more peripheral interfaces such as interfaces for printers, pointing devices (mice, track pad, etc.), keyboards, and the like.

Bus 162 allows processor(s) 152, memory device(s) 154, interface(s) 156, mass storage device(s) 158, and I/O device(s) 160 to communicate with one another, as well as other devices or components coupled to bus 162. Bus 162 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 150, and are executed by processor(s) 152. Alternatively, the systems and procedures described herein can be implemented in hardware, or a combination of hardware, software, and/or firmware. For example, one or more application specific integrated circuits (ASICs) or field programmable gate arrays (FPGAs) can be programmed to carry out one or more of the systems and procedures described herein.

Figure 2A:
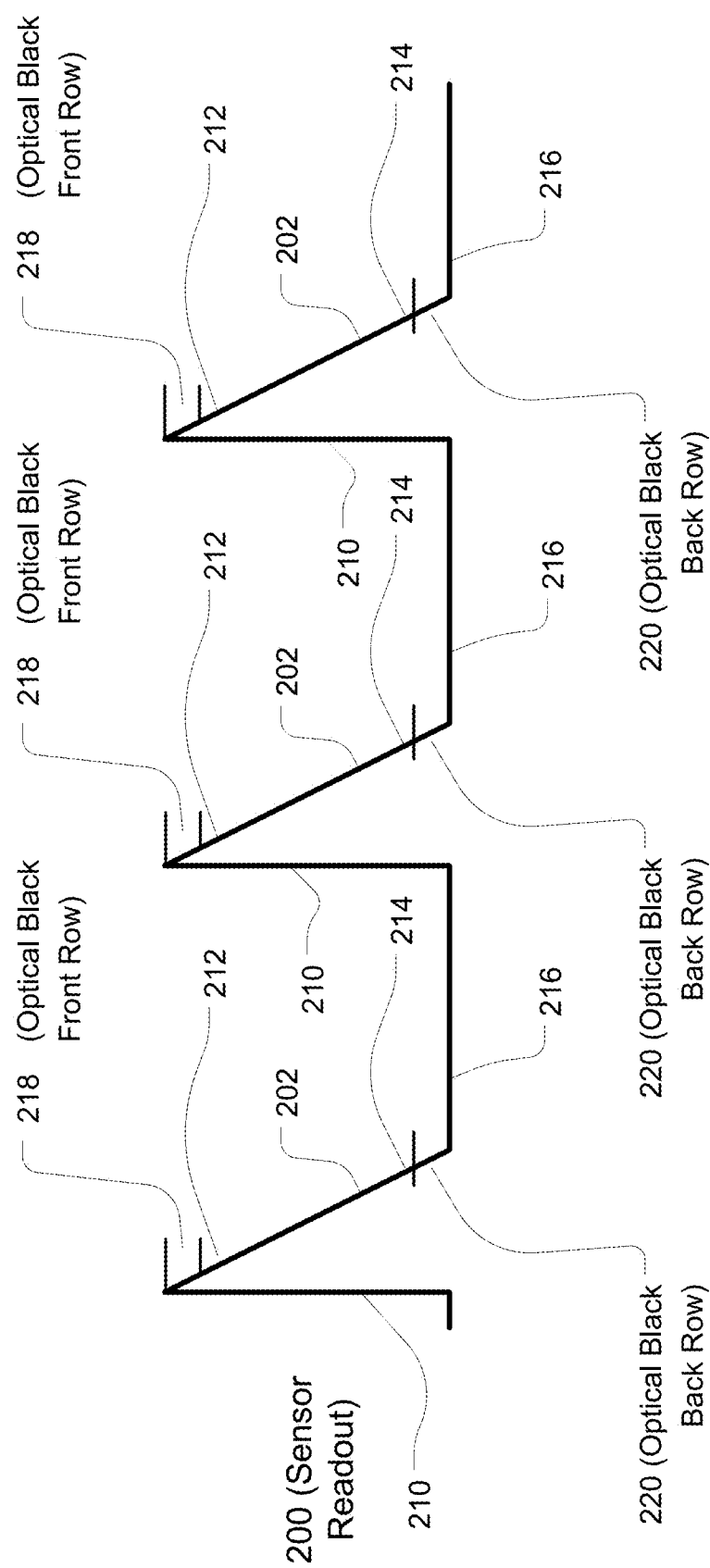
Figure 2D:
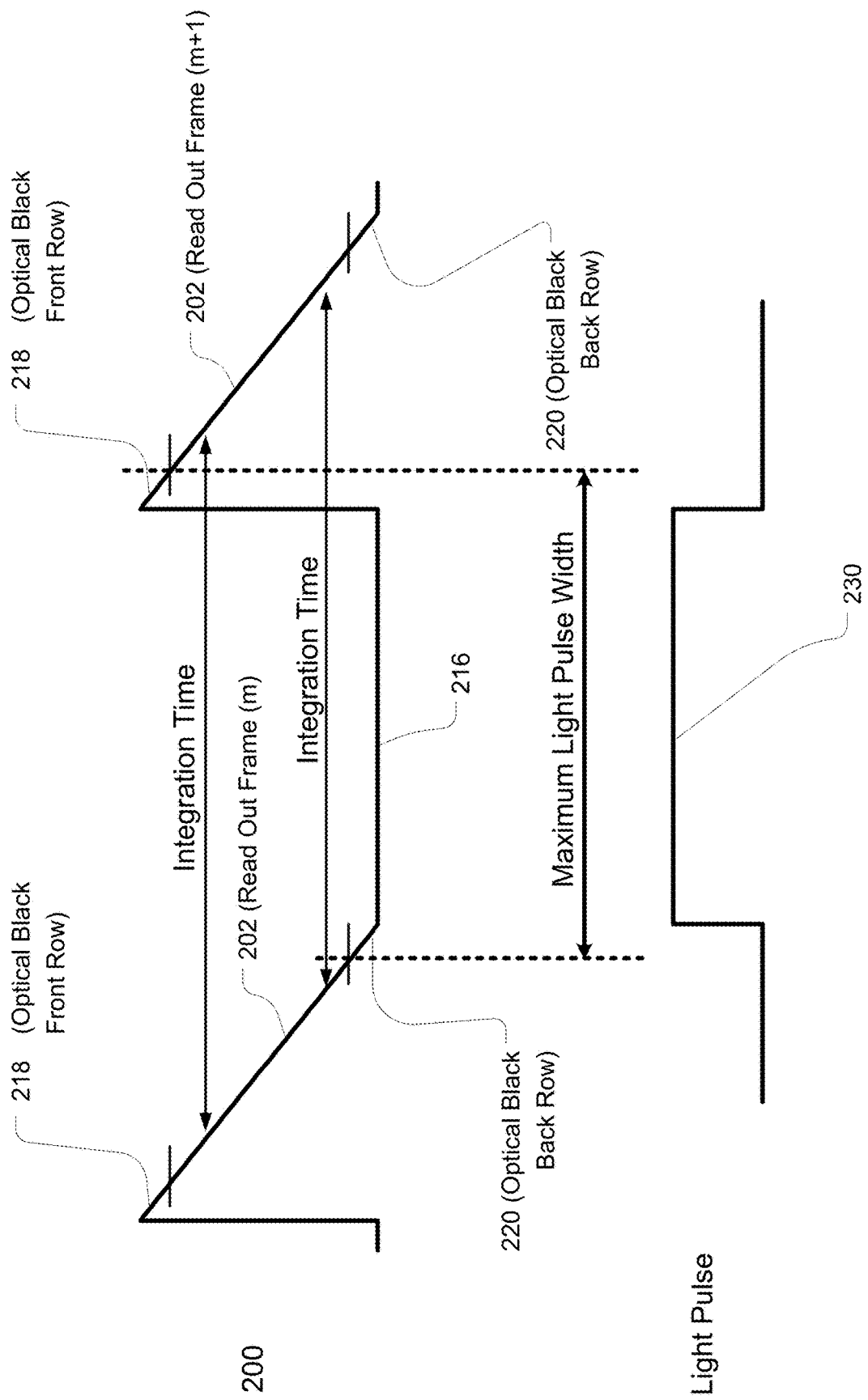

FIG. 2A illustrates the operational cycles of an image sensor used in rolling readout mode or during the sensor readout 200. The frame readout phase may start at and may be represented by vertical line 210. The frame readout phase is represented by the diagonal or slanted line 202. The sensor may be read out on a row by row basis, the top of the downwards slanted edge being the sensor top row 212 and the bottom of the downwards slanted edge being the sensor bottom row 214. The time between the last row readout and the next readout cycle may be called the blanking time 216. It should be noted that some of the sensor pixel rows might be covered with a light shield (e.g., a metal coating or any other substantially black layer of another material type). These covered pixel rows may be referred to as optical black rows 218 and 220. Optical black rows 218 and 220 may be used as input for correction algorithms. As shown in FIG. 2A, these optical black rows 218 and 220 may be located on the top of the pixel array or at the bottom of the pixel array or at the top and the bottom of the pixel array. FIG. 2B illustrates a process of controlling the amount of electromagnetic radiation, e.g., light, that is exposed to a pixel, thereby integrated or accumulated by the pixel. It will be appreciated that photons are elementary particles of electromagnetic radiation. Photons are integrated, absorbed, or accumulated by each pixel and converted into an electrical charge or current. An electronic shutter or rolling shutter (shown by dashed line 222) may be used to start the integration time by resetting the pixel. The light will then integrate until the next frame readout phase. The position of the electronic shutter 222 can be moved between two operational cycles in order to control the pixel saturation for a given amount of light. It should be noted that this technique allows for a constant integration time between two different lines, but introduces a delay when moving from top to bottom rows. FIG. 2C illustrates the case where the electronic shutter 222 has been removed. In this configuration, the integration of the incoming light may start during frame readout phase 202 and may end at the next operational cycle, which also defines the start of the next integration. FIG. 2D shows a configuration without an electronic shutter 222, but with a controlled and pulsed light 230 during the blanking time 216. This ensures that all rows see the same light issued from the same light pulse 230. In other words, each row will start its integration in a dark environment, which may be at the optical black back row 220 of frame (m) for a maximum light pulse width, and will then receive a light strobe and will end its integration in a dark environment, which may be at the optical black front row 218 of the next succeeding frame (m+1) for a maximum light pulse width. In the FIG. 2D example, the image generated from the light pulse will be solely available during the frame readout phase of frame (m+1) without any interference with frames (m) and (m+2). It should be noted that the condition to have a light pulse to be read out only in one frame and not interfere with neighboring frames is to have the given light pulse firing during the blanking time 216. Because the optical black rows 218, 220 are insensitive to light, the time spent reading out optical black back rows 220 of frame (m) and the time spent reading out optical black front rows 218 of frame (m+1) can be added to the blanking time 216 to determine the maximum range of the firing time of the light pulse 230. As illustrated in the FIG. 2A, a sensor may be cycled many times in order to receive data for each pulsed color (e.g., Red, Green, Blue). Each cycle may be timed. In an embodiment, the cycles may be timed to operate within an interval of 16.67 ms. In another embodiment, the cycles may be timed to operate within an interval of 8.3 ms. It will be appreciated that other timing intervals are contemplated by the disclosure and are intended to fall within the scope of this disclosure.

FIG. 3 graphically illustrates the operation of an embodiment of an electromagnetic emitter. An emitter may be timed to correspond with the cycles of a sensor, such that electromagnetic radiation is emitted within the sensor operation cycle and/or during a portion of the sensor operation cycle. FIG. 3 illustrates Pulse 1 at 302, Pulse 2 at 304, and Pulse 3 at 306. In an embodiment, the emitter may pulse during the frame readout phase 202 of the sensor operation cycle. In an embodiment, the emitter may pulse during the blanking time 216 of the sensor operation cycle. In an embodiment, the emitter may pulse for a duration that is during portions of two or more sensor operational cycles. In an embodiment, the emitter may begin a pulse during the blanking time 216, or during the optical black portion 220 of the frame readout phase 202, and end the pulse during the frame readout phase 202, or during the optical black portion 218 of the frame readout phase 202 of the next succeeding cycle. It will be understood that any combination of the above is intended to fall within the scope of this disclosure as long as the pulse of the emitter and the cycle of the sensor correspond.

Figure 4:
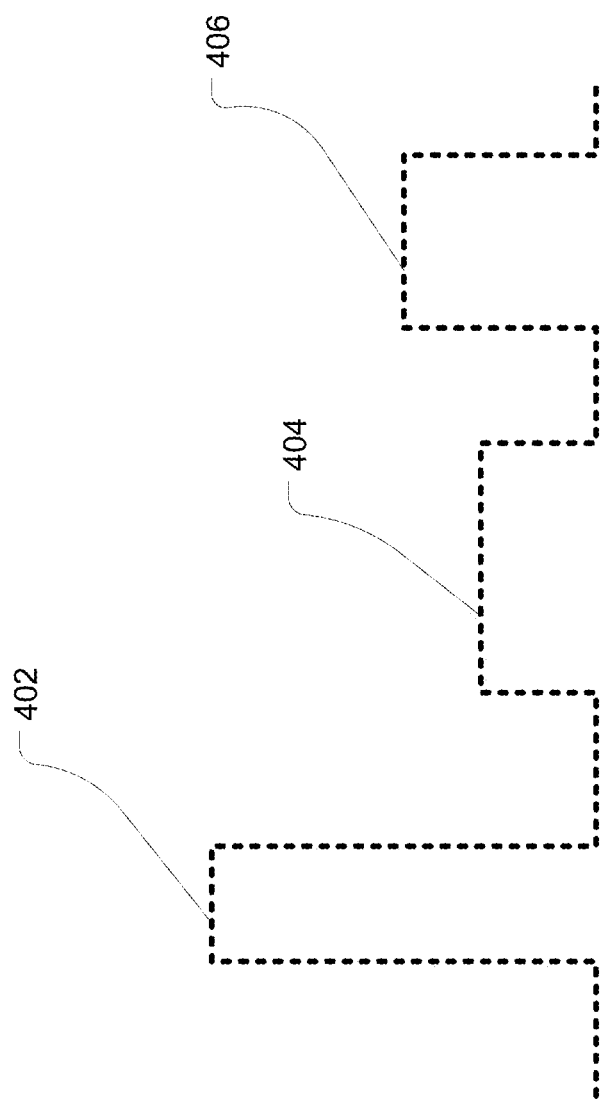
FIG. 4 is a graphical representation of varying the duration and magnitude of the emitted electromagnetic pulse in order to provide exposure control in accordance with the principles and teachings of the disclosure.

FIG. 4 graphically represents varying the duration and magnitude of the emitted electromagnetic pulse (e.g., Pulse 1 at 402, Pulse 2 at 404, and Pulse 3 at 406) to control exposure. An emitter having a fixed output magnitude may be pulsed during any of the cycles noted above in relation to FIGS. 2D and 3 for an interval to provide the needed electromagnetic energy to the pixel array. An emitter having a fixed output magnitude may be pulsed at a longer interval of time, thereby providing more electromagnetic energy to the pixels or the emitter may be pulsed at a shorter interval of time, thereby providing less electromagnetic energy. Whether a longer or shorter interval time is needed depends upon the operational conditions.

In contrast to adjusting the interval of time that the emitter pulses a fixed output magnitude, the magnitude of the emission itself may be increased in order to provide more electromagnetic energy to the pixels. Similarly, decreasing the magnitude of the pulse provides less electromagnetic energy to the pixels. It should be noted that an embodiment of the system may have the ability to adjust both magnitude and duration concurrently, if desired. Additionally, the sensor may be adjusted to increase its sensitivity and duration as desired for optimal image quality. FIG. 4 illustrates varying the magnitude and duration of the pulses. In the illustration, Pulse 1 at 402 has a higher magnitude or intensity than either Pulse 2 at 404 or Pulse 3 at 406. Additionally, Pulse 1 at 402 has a shorter duration than Pulse 2 at 404 or Pulse 3 at 406, such that the electromagnetic energy provided by the pulse is illustrated by the area under the pulse shown in the illustration. In the illustration, Pulse 2 at 404 has a relatively low magnitude or intensity and a longer duration when compared to either Pulse 1 at 402 or Pulse 3 at 406. Finally, in the illustration, Pulse 3 at 406 has an intermediate magnitude or intensity and duration, when compared to Pulse 1 at 402 and Pulse 2 at 404.

Figure 5:
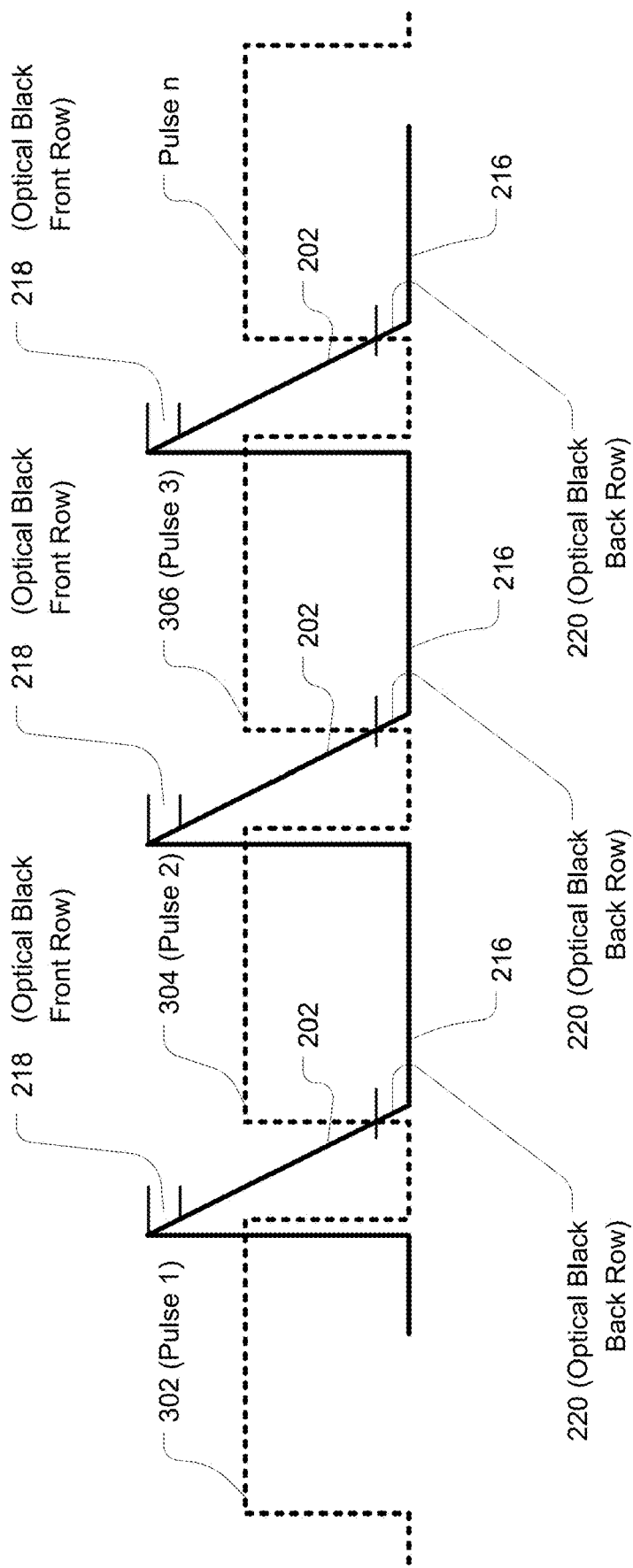
FIG. 5 is a graphical representation of an embodiment of the disclosure combining the operational cycles of a sensor, the electromagnetic emitter and the emitted electromagnetic pulses of FIGS. 2A-4, which demonstrate the imaging system during operation in accordance with the principles and teachings of the disclosure.

FIG. 5 is a graphical representation of an embodiment of the disclosure combining the operational cycles, the electromagnetic emitter and the emitted electromagnetic pulses of FIGS. 2-4 to demonstrate the imaging system during operation in accordance with the principles and teachings of the disclosure. As can be seen in the figure, the electromagnetic emitter pulses the emissions primarily during the blanking time 216 of the sensor, such that the pixels will be charged and ready to read during the frame readout phase 202 of the operational cycle of the sensor. The dashed line portions in the pulse (from FIG. 3) illustrate the potential or ability to emit electromagnetic energy during the optical black portions 220 and 218 of the operational cycle of the sensor 200 if additional time is needed or desired to pulse electromagnetic energy.

Referring now to FIGS. 6-9A, FIG. 6 illustrates a schematic of two distinct processes over a period of time from t(0) to t(1) for recording an image frame of video stream for full spectrum light and partitioned spectrum light. It should be noted that color sensors have a color filter array (CFA) for filtering out certain wavelengths of light per pixel commonly used for full spectrum light reception. An example of a CFA is a Bayer pattern. Because the color sensor may comprise pixels within the array that are made sensitive to a single color from within the full spectrum, a reduced resolution image results because the pixel array has pixel spaces dedicated to only a single color of light within the full spectrum. Usually such an arrangement is formed in a checkerboard type pattern across the entire array.

In contrast, when partitioned spectrums of light are used a sensor can be made to be sensitive or responsive to the magnitude of all light energy because the pixel array will be instructed that it is sensing electromagnetic energy from a predetermined partition of the full spectrum of electromagnetic energy in each cycle. Therefore, to form an image frame the sensor need only be cycled with a plurality frames having a plurality of differing partitions from within the full spectrum of light and then reassembling the frames into an image frame to display a predetermined mixture of color values for every pixel across the array. Accordingly, a higher resolution image frame is also provided because there are reduced distances as compared to a Bayer sensor between pixel centers of the same color sensitivity for each of the color pulses. As a result, the formed colored image frame has a higher modulation transfer function (MTF). Because the image from each frame, has a higher resolution, the resultant image created when a plurality of frames are combined into a full color image frame, also has a higher resolution. In other words, because each and every pixel within the array (instead of, at most, every second pixel in a sensor with color filter) is sensing the magnitudes of energy for a given pulse and a given scene, just fractions of time apart, a higher resolution image frame is created for each scene with less derived (less accurate) data needing to be introduced.

For example, white or full spectrum visible light is a combination of red, green and blue light. In the embodiment shown in FIG. 6, it can be seen that in both the partitioned spectrum process 620 and full spectrum process 610 the time to capture an image is t(0) to t(1). In the full spectrum process 610, white light or full spectrum electromagnetic energy is emitted at 612. At 614, the white or full spectrum electromagnetic energy is sensed. At 616, the image is processed and displayed. Thus, between time t(0) and t(1), the image has been processed and displayed. Conversely, in the partitioned spectrum process 620, a first partition is emitted at 622 and sensed at 624. At 626, a second partition is emitted and then sensed at 628. At 630, a third partition is emitted and sensed at 632. At 634, the image is processed and displayed. It will be appreciated that any system using an image sensor cycle that is at least two times faster than the white light cycle is intended to fall within the scope of the disclosure.

Figure 6:
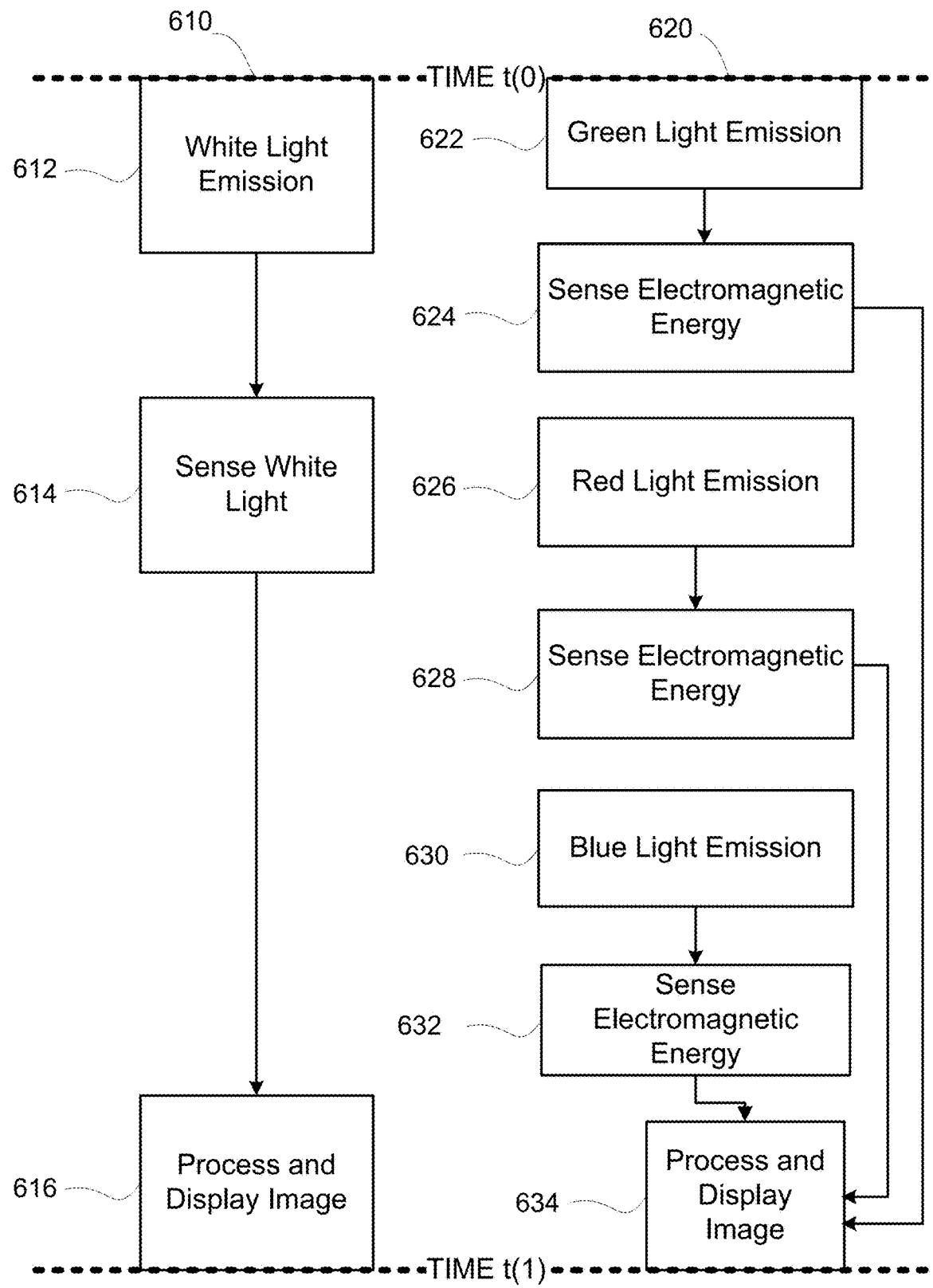
FIG. 6 illustrates a schematic of two distinct processes over a period of time from t(0) to t(1) for recording an image frame of a video stream for full spectrum light and partitioned spectrum light in accordance with the principles and teachings of the disclosure.

As can be seen graphically in the embodiment illustrated in FIG. 6 between times t(0) and t(1), the sensor for the partitioned spectrum system 620 has cycled three times for every one of the full spectrum system. In the partitioned spectrum system 620, the first of the three sensor cycles is for a green spectrum 622 and 624, the second of the three is for a red spectrum 626 and 628, and the third is for a blue spectrum 630 and 632. Thus, in an embodiment, wherein the display device (LCD panel) operates at 50-60 image frames per second, a partitioned light system should operate at 150-180 frames per second to produce the 50-60 image frames per second and maintain the continuity and smoothness of the displayed video stream.

In other embodiments there may be different frame capture rates and image frame display rates. Furthermore, the average frame capture rate could be any multiple of the image frame display rate.

In an embodiment it may be desired that not all partitions be represented equally within the system frame rate. In other words, not all light sources have to be pulsed with the same regularity so as to emphasize and de-emphasize aspects of the recorded scene as desired by the users. It should also be understood that non-visible and visible partitions of the electromagnetic spectrum may be pulsed together within a system with their respective data value being stitched into the video output as desired for display to a user.

An embodiment may comprise a pulse cycle pattern as follows:
Green pulse;
Red pulse;
Blue pulse;
Green pulse;
Red pulse;
Blue pulse;
Infra-red (IR) pulse;
(Repeat)

As can be seen in the example, an IR partition may be pulsed at a rate differing from the rates of the other partition pulses. This may be done to emphasize a certain aspect of the scene, with the IR data simply being overlaid with the other data in the video output to make the desired emphasis. It should be noted that the addition of a fourth electromagnetic partition does not necessarily require the serialized system to operate at four times the rate of a full spectrum non-serial system because every partition does not have to be represented equally in the pulse pattern. As seen in the embodiment, the addition of a partition pulse that is represented less in a pulse pattern (IR in the above example), would result in an increase of less than 20% of the cycling speed of the sensor in order accommodate the irregular partition sampling.

In an embodiment, an electromagnetic partition may be emitted that is sensitive to dyes or materials that are used to highlight aspects of a scene. In the embodiment it may be sufficient to highlight the location of the dyes or materials without need for high resolution. In such an embodiment, the dye sensitive electromagnetic partition may be cycled much less frequently than the other partitions in the system in order to include the emphasized data.

Figure 7A:
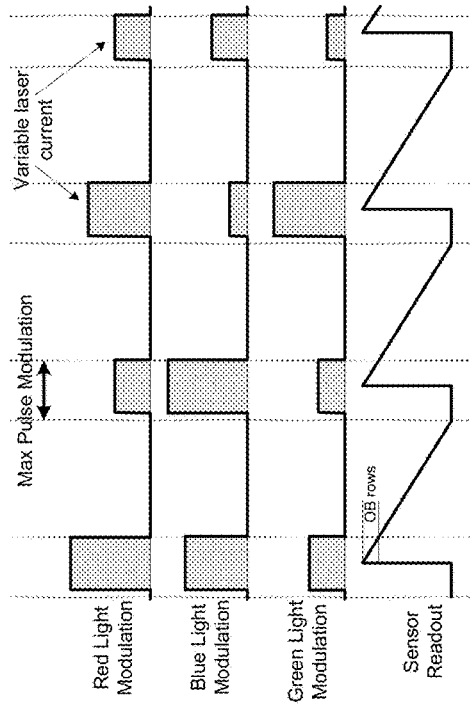
FIGS. 7A-7E illustrate schematic views of the processes over an interval of time for recording an image frame of a video stream for both full spectrum light and partitioned spectrum light in accordance with the principles and teachings of the disclosure.
Figure 7B:
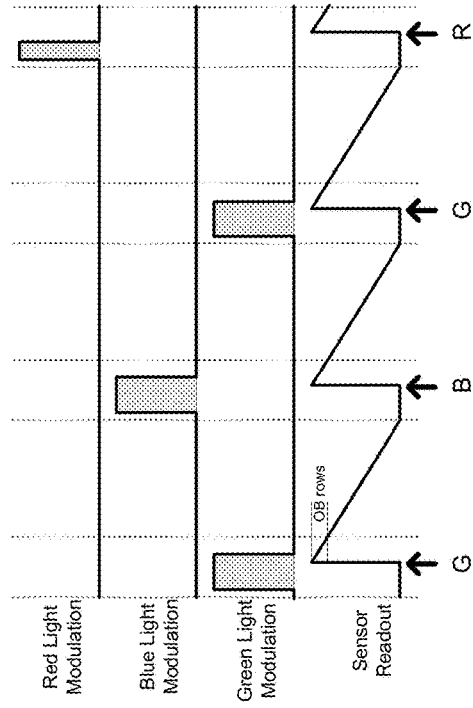
Figure 7C:
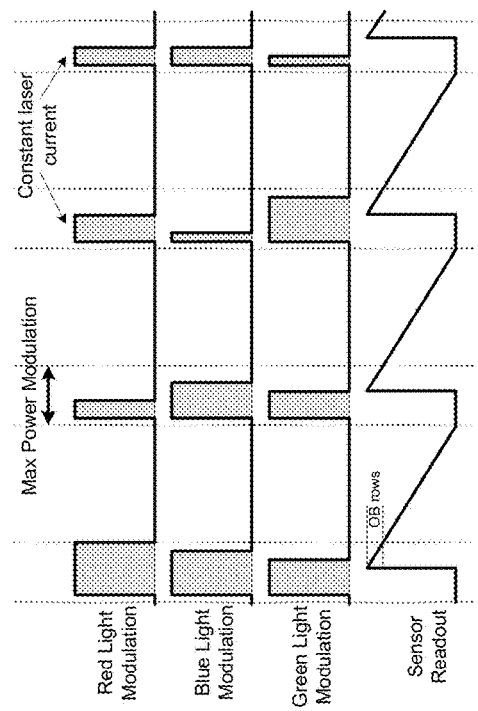

The partition cycles may be divided so as to accommodate or approximate various imaging and video standards. In an embodiment, the partition cycles may comprise pulses of electromagnetic energy in the Red, Green, Blue spectrum as follows as illustrated best in FIGS. 7A-7D. In FIG. 7A, the different light intensities have been achieved by modulating the light pulse width or duration within the working range shown by the vertical grey dashed lines. In FIG. 7B, the different light intensities have been achieved by modulating the light power or the power of the electromagnetic emitter, which may be a laser or LED emitter, but keeping the pulse width or duration constant. FIG. 7C shows the case where both the light power and the light pulse width are being modulated, leading to greater flexibility. The partition cycles may use CMY, IR and ultraviolet using a non-visible pulse source mixed with visible pulse sources and any other color space required to produce an image or approximate a desired video standard that is currently known or yet to be developed. It should also be understood that a system may be able to switch between the color spaces on the fly in order to provide the desired image output quality.

Figure 7D:
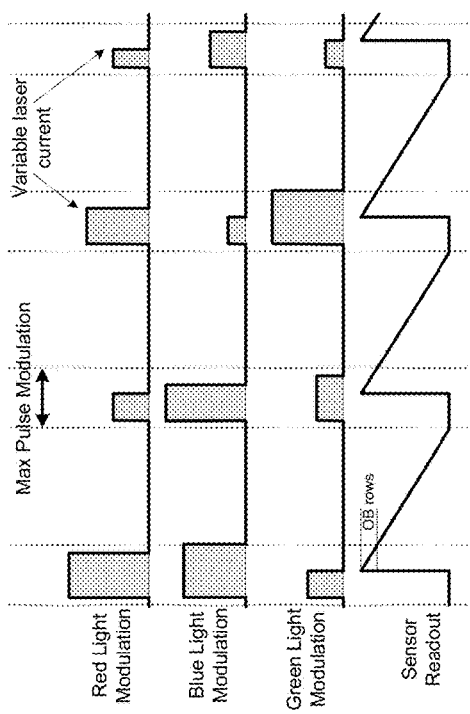

In an embodiment using color spaces Green-Blue-Green-Red (as seen in FIG. 7D) it may be desirous to pulse the luminance components more often than the chrominance components because users are generally more sensitive to light magnitude differences than to light color differences. This principle can be exploited using a mono-chromatic sensor as illustrated in FIG. 7D. In FIG. 7D, green, which contains the most luminance information, may be pulsed more often or with more intensity in a (G-B-G-R-G-B-G-R . . . ) scheme to obtain the luminance data. Such a configuration would create a video stream that has perceptively more detail, without creating and transmitting unperceivable data.

Figure 7E:
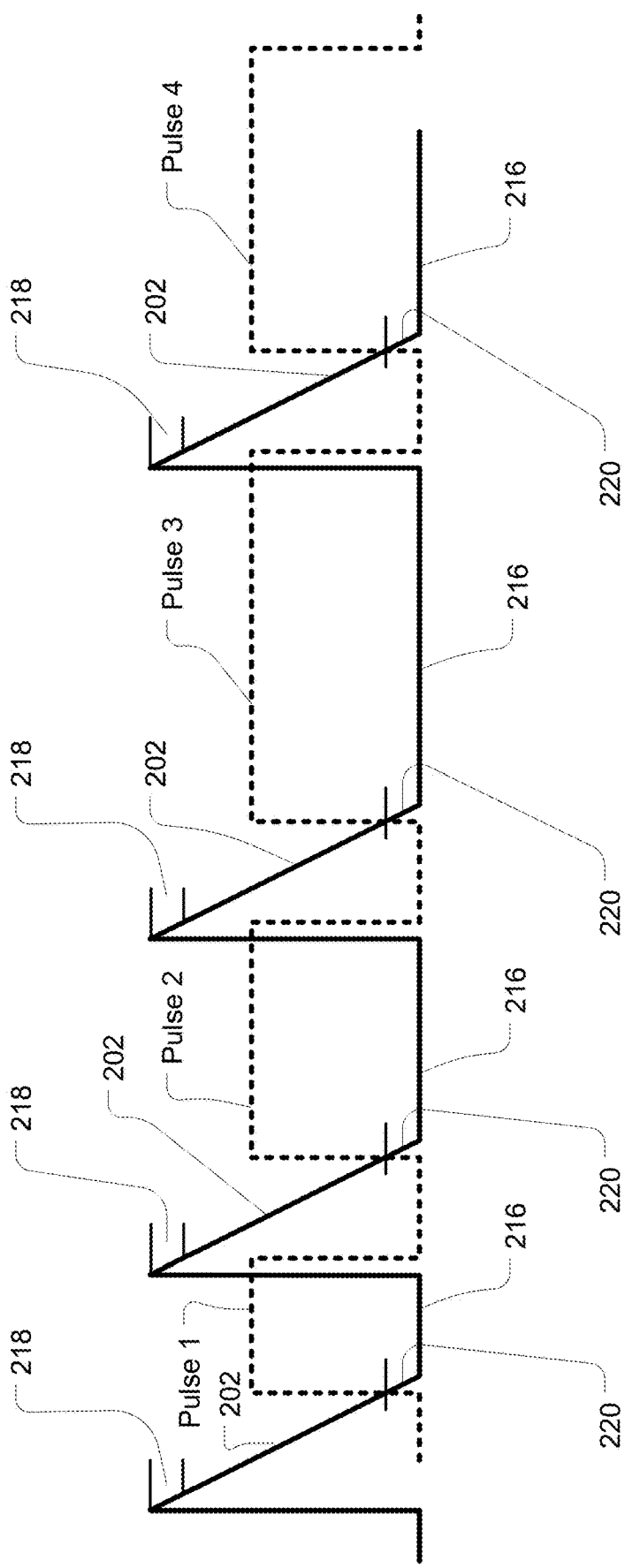

In an embodiment, duplicating the pulse of a weaker partition may be used to produce an output that has been adjusted for the weaker pulse. For example, blue laser light is considered weak relative to the sensitivity of silicon based pixels and is difficult to produce in comparison to the red or green light, and therefore may be pulsed more often during an image frame cycle to compensate for the weakness of the light. These additional pulses may be done serially over time or by using multiple lasers that simultaneously pulse to produce the desired compensation effect. It should be noted that by pulsing during blanking time (time during which the sensor is not reading out the pixel array), the sensor is insensitive to differences/mismatches between lasers of the same kind and simply accumulates the light for the desired output. In another embodiment, the maximum light pulse range may be different from frame to frame. This is shown in FIG. 7E where the light pulses are different from frame to frame. The sensor may be built in order to be able to program different blanking times with a repeating pattern of 2 or 3 or 4 or n frames. In FIG. 7E, 4 different light pulses are illustrated and Pulse 1 may repeat for example after Pulse 4, and may have a pattern of 4 frames with different blanking times. This technique can be used to place the most powerful partition on the smallest blanking time and therefore allow the weakest partition to have wider pulse on one of the next frames without the need of increasing the readout speed. The image frame can still have a regular pattern from frame to frame as it is constituted of many frames.

Figure 8:
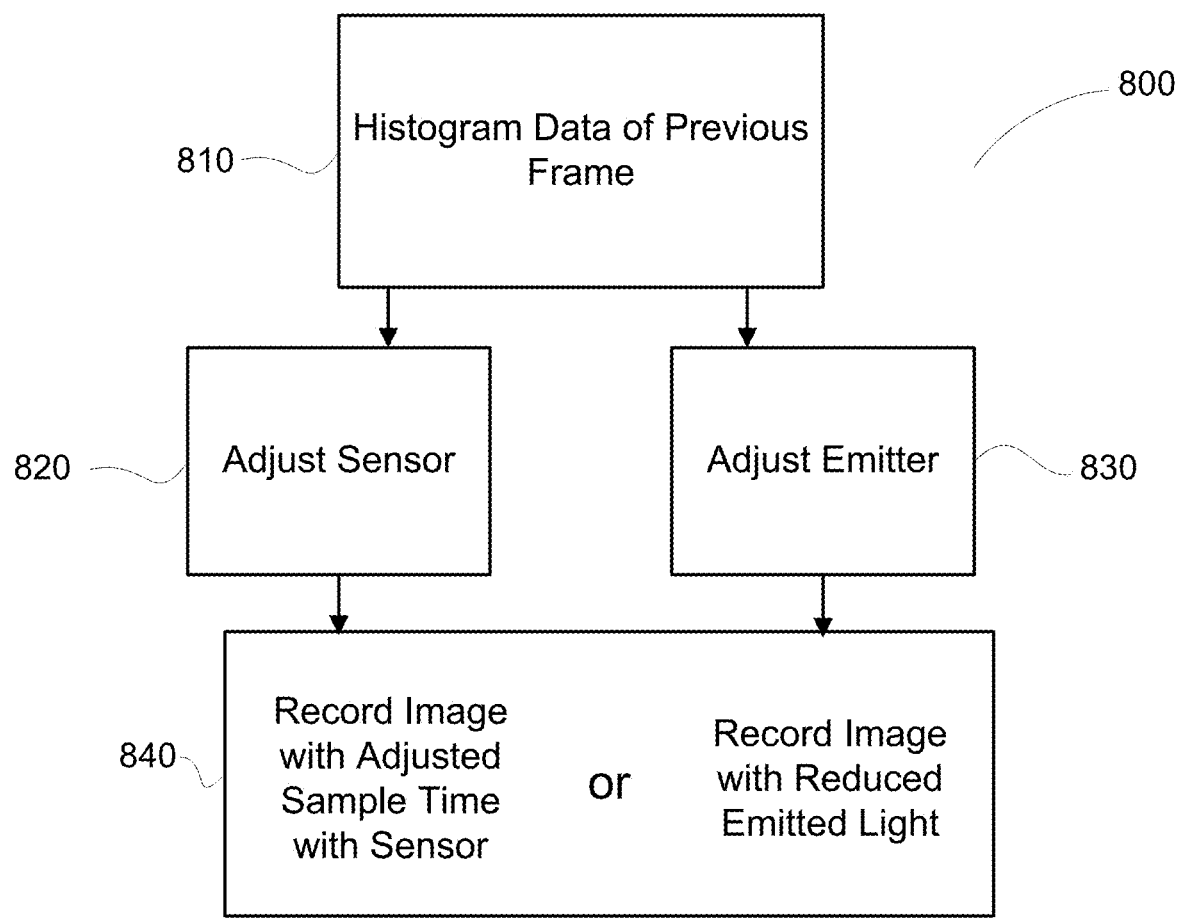
FIGS. 8-12 illustrate the adjustment of both the electromagnetic emitter and the sensor, wherein such adjustment may be made concurrently in some embodiments in accordance with the principles and teachings of the disclosure.
Figure 9:
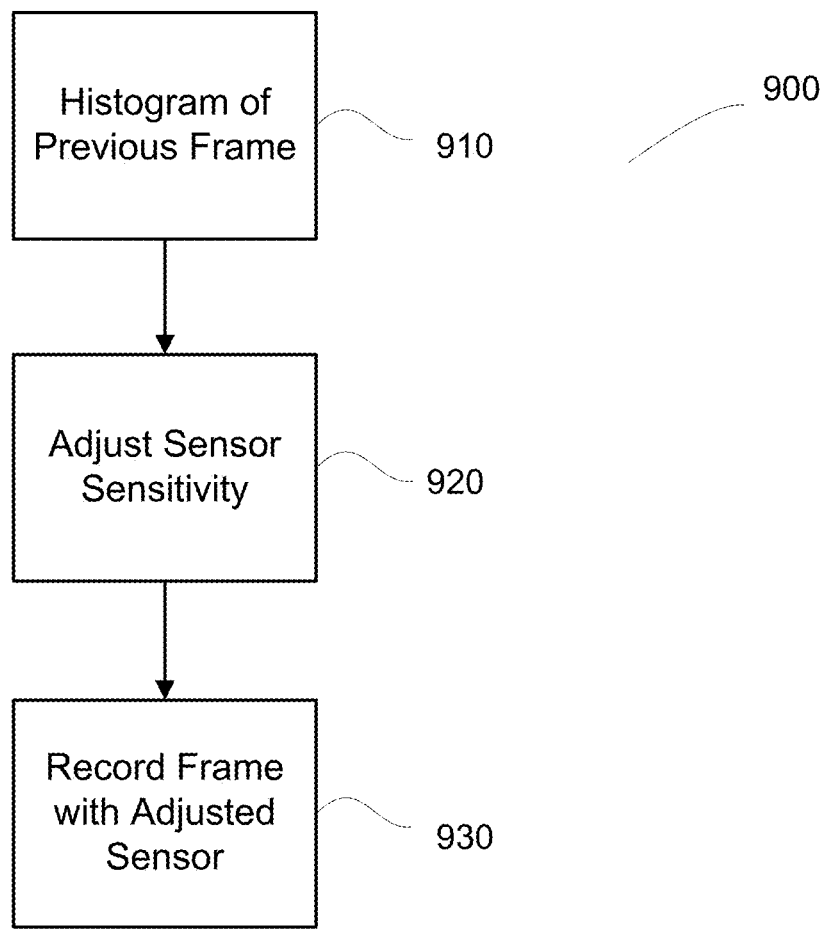

As can be seen in FIG. 8, because each partitioned spectrum of light may have different energy values, the sensor and/or light emitter may be adjusted to compensate for the differences in the energy values. At 810, the data obtained from the histogram from a previous frame may be analyzed. At 820, the sensor may be adjusted as noted below. Additionally, at 830, the emitter may be adjusted. At 840, the image may be obtained from the adjusted sample time from the sensor or the image may be obtained with adjusted (either increased or decreased) emitted light, or a combination of the above. For example, because the red light spectrum is more readily detected by a sensor within the system than the blue light spectrum, the sensor can be adjusted to be less sensitive during the red partition cycle and more sensitive during the blue partition cycle because of the low Quantum Efficiency that the blue partition has with respect to silicon (illustrated best in FIG. 9). Similarly, the emitter may be adjusted to provide an adjusted partition (e.g., higher or lower intensity and duration). Further, adjustments may be made at the sensor and emitter level both. The emitter may also be designed to emit at one specific frequency or may be changed to emit multiple frequencies of a specific partition to broaden the spectrum of light being emitted, if desired for a particular application.

Figure 10:
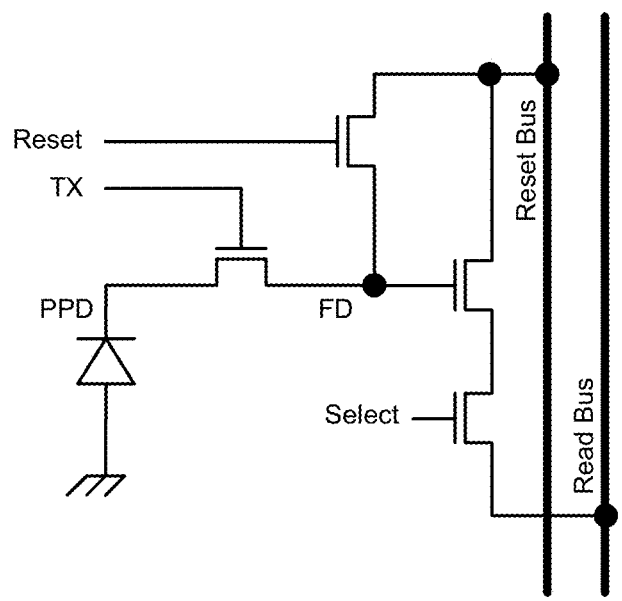

FIG. 10 shows a schematic of an unshared 4T pixel. The TX signal is used to transfer accumulated charges from the photo diode (PPD) to the floating diffusion (FD). The reset signal is used to reset the FD to the reset bus. If reset and TX signals are "On" at the same time, the PPD is constantly reset (each photo charge generated in the PPD is directly collected at the reset bus) and the PPD is always empty. Usual pixel array implementation includes a horizontal reset line that attaches the reset signals of all pixels within one row and a horizontal TX line that attaches the TX signals of all pixels within one row.

Figure 11:
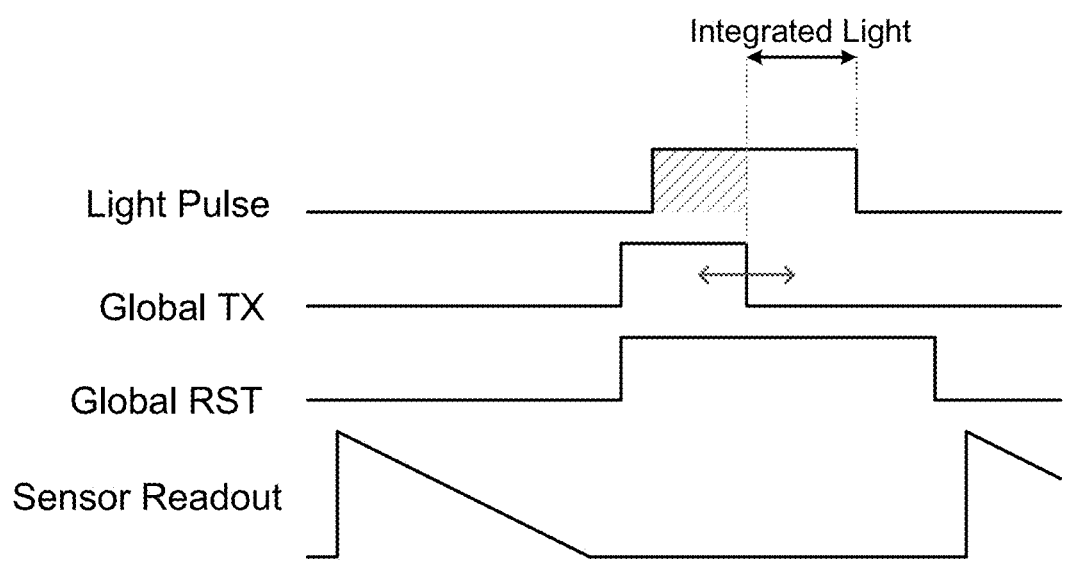

In an embodiment, timing of the sensor sensibility adjustment is illustrated and sensor sensibility adjustment can be achieved using a global reset mechanism (i.e., a means of firing all pixel array reset signals at once) and a global TX mechanism (i.e., a means of firing all pixel array TX signals at once). This is shown in FIG. 11. In this case, the light pulse is constant in duration and amplitude, but the light integrated in all pixels starts with the "on" to "off" transition of the global TX and ends with the light pulse. Therefore, the modulation is achieved by moving the falling edge of the global TX pulse.

Figure 12:
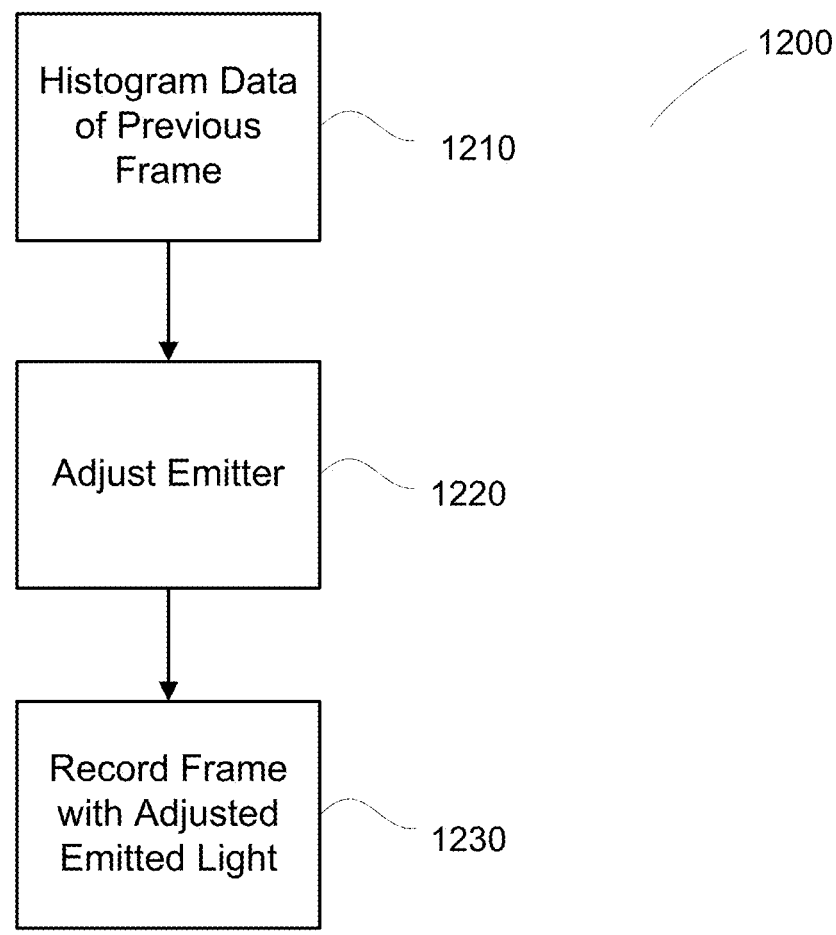

Conversely, the emitter may emit red light at a lesser intensity than blue light in order to produce a correctly exposed image (illustrated best in FIG. 12). At 1210, the data obtained from the histogram from a previous frame may be analyzed. At 1220, the emitter may be adjusted. At 1230, the image may be obtained from the adjusted emitted light. Additionally, in an embodiment both the emitter and the sensor can be adjusted concurrently.

Reconstructing the partitioned spectrum frames into a full spectrum image frame for later output could be as simple as blending the sensed values for each pixel in the array in some embodiments. Additionally, the blending and mixing of values may be simple averages, or may be tuned to a predetermined lookup table (LUT) of values for desired outputs. In an embodiment of a system using partitioned light spectrums, the sensed values may be post-processed or further refined remotely from the sensor by an image or secondary processor, and just before being output to a display.

Figure 13:
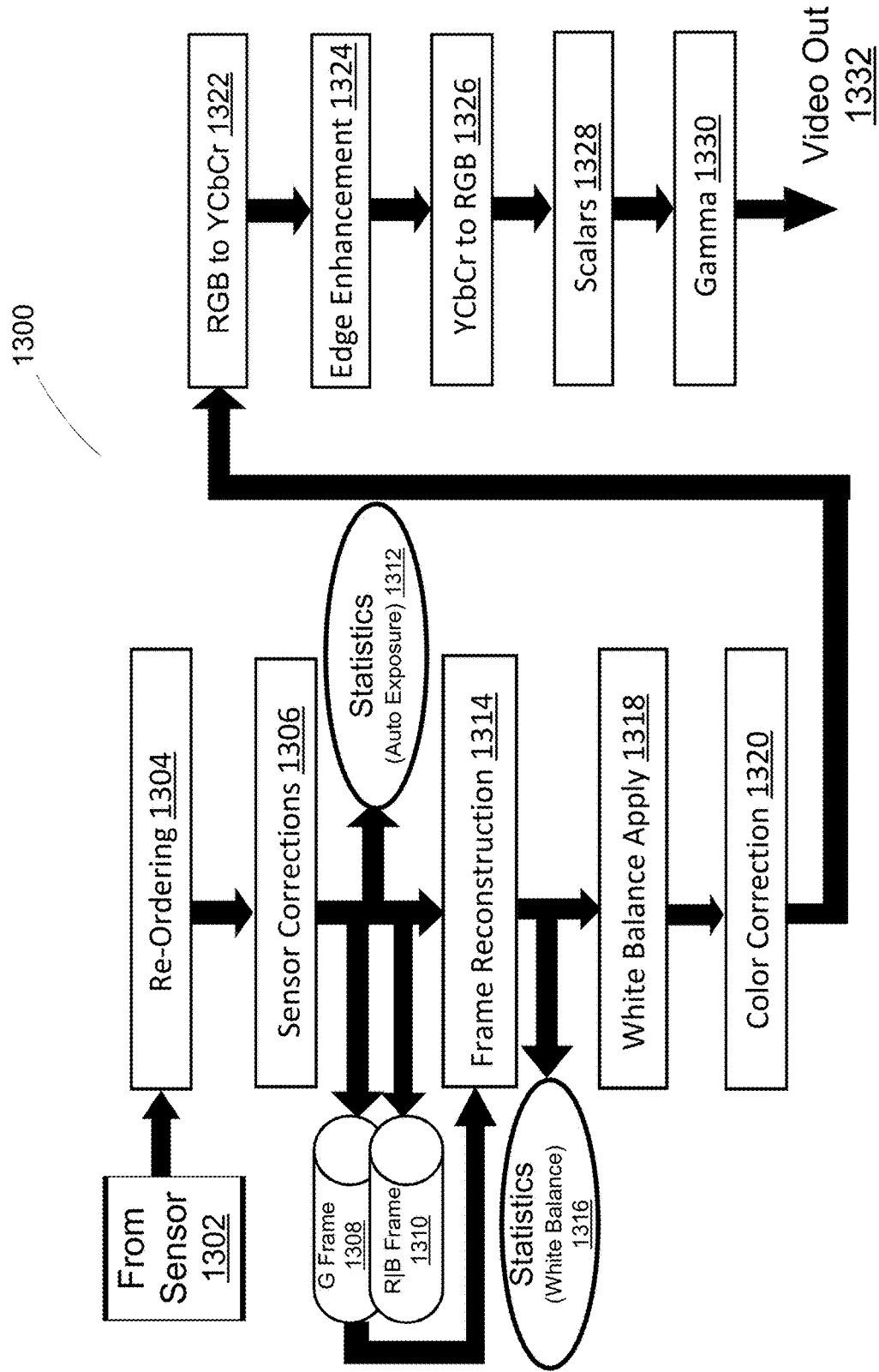
FIGS. 13-21 illustrate sensor correction methods and hardware schematics for use with a partitioned light system in accordance with the principles and teachings of the disclosure.

FIG. 13 illustrates a basic example at 1300 of a monochrome ISP and how an ISP chain may be assembled for the purpose of generating sRGB image sequences from raw sensor data, yielded in the presence of the G-R-G-B light pulsing scheme.

Figure 21:
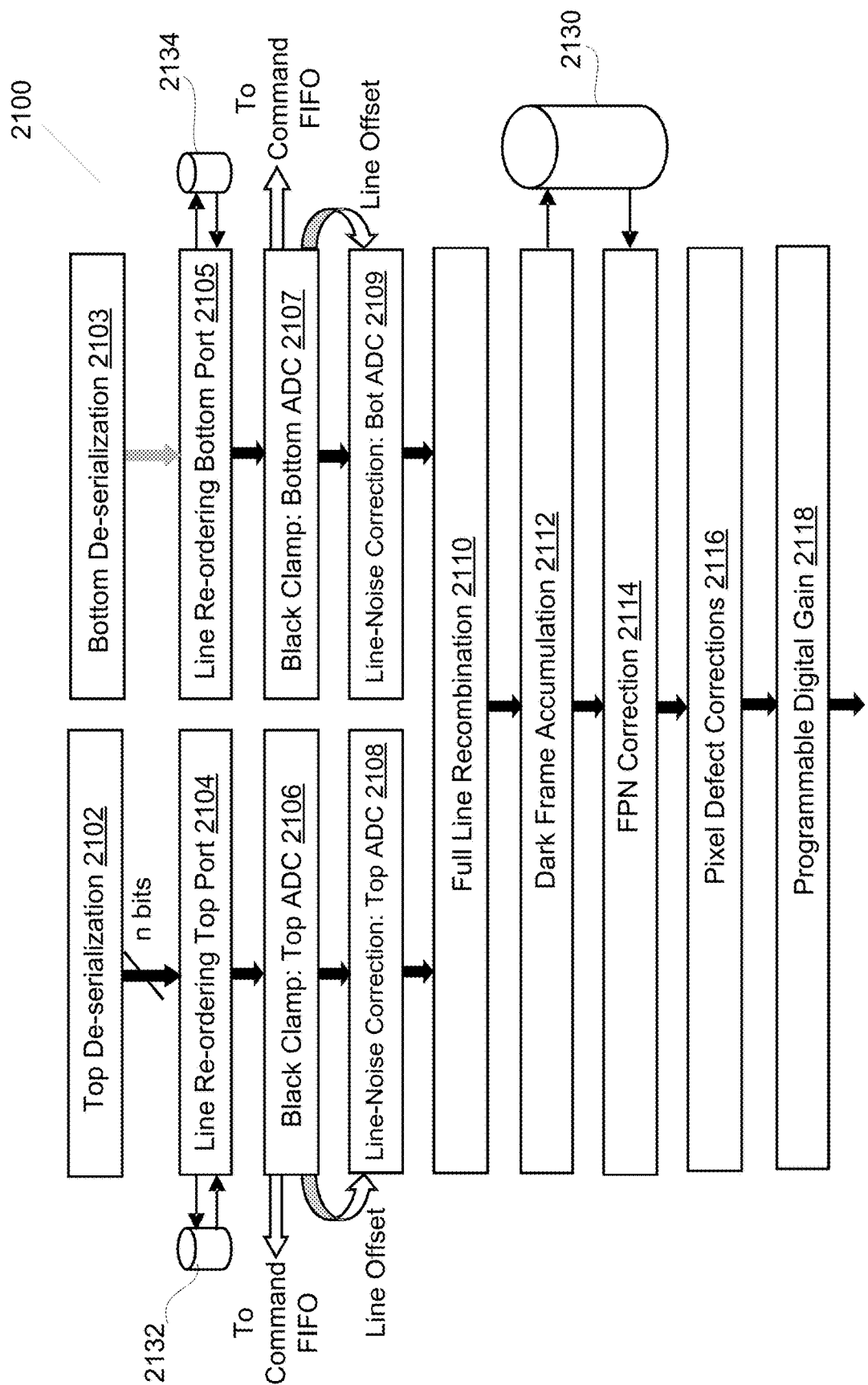

The first stage is concerned with making corrections (see 1302, 1304 and 1306 in FIG. 13) to account for any non-idealities in the sensor technology for which it is most appropriate to work in the raw data domain (see FIG. 21).

At the next stage, two frames (see 1308 and 1310 in FIG. 13) would be buffered since each image frame derives data from three raw frames. The image frame reconstruction at 1314 would proceed by sampling data from the current frame and the two buffered frames (1308 and/or 1310). The image frame reconstruction process results in full color image frames in linear RGB color space.

In this example, the white balance coefficients at 1318 and color correction matrix at 1320 are applied before converting to YCbCr space at 1322 for subsequent edge enhancement at 1324. After edge enhancement at 1324, images are transformed back to linear RGB at 1326 for scaling at 1328, if applicable.

Finally, the gamma transfer function at 1330 would be applied to translate the data into the sRGB domain at 1332.

Figure 14:
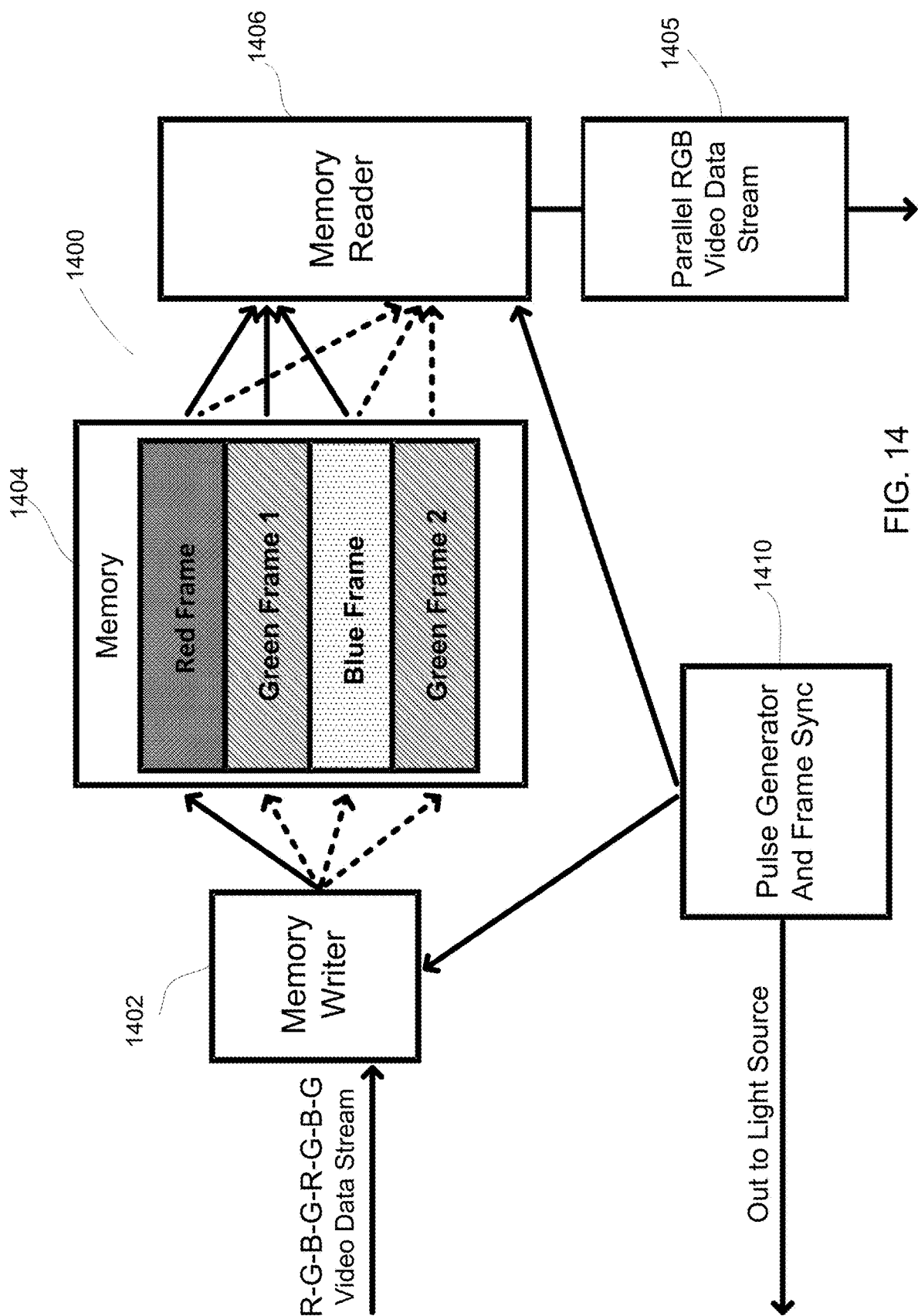

FIG. 14 is an embodiment example of color fusion hardware. The color fusion hardware takes in an RGBGRGBGRGBG video data stream at 1402 and converts it to a parallel RGB video data stream at 1405. The bit width on the input side may be, e.g., 12 bits per color. The output width for that example would be 36 bits per pixel. Other embodiments may have different initial bit widths and 3 times that number for the output width. The memory writer block takes as its input the RGBG video stream at 1402 and writes each frame to its correct frame memory buffer at 1404 (the memory writer triggers off the same pulse generator 1410 that runs the laser light source). As illustrated at 1404, writing to the memory follows the pattern, Red, Green 1, Blue, Green 2, and then starts back with Red again. At 1406, the memory reader reads three frames at once to construct an RGB pixel. Each pixel is three times the bit width of an individual color component. The reader also triggers off the laser pulse generator at 1410. The reader waits until Red, Green 1 and Blue frames have been written, then proceeds to read them out in parallel while the writer continues writing Green 2 and starts back on Red. When Red completes the reader begins reading from Blue, Green 2 and Red. This pattern continues indefinitely.

Figure 15:
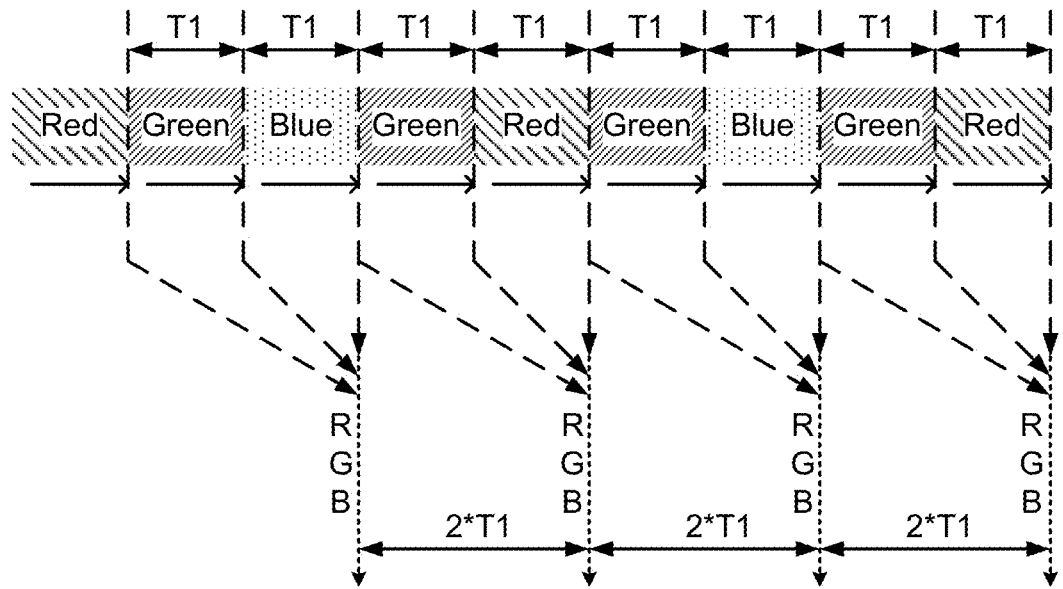
Figure 16:
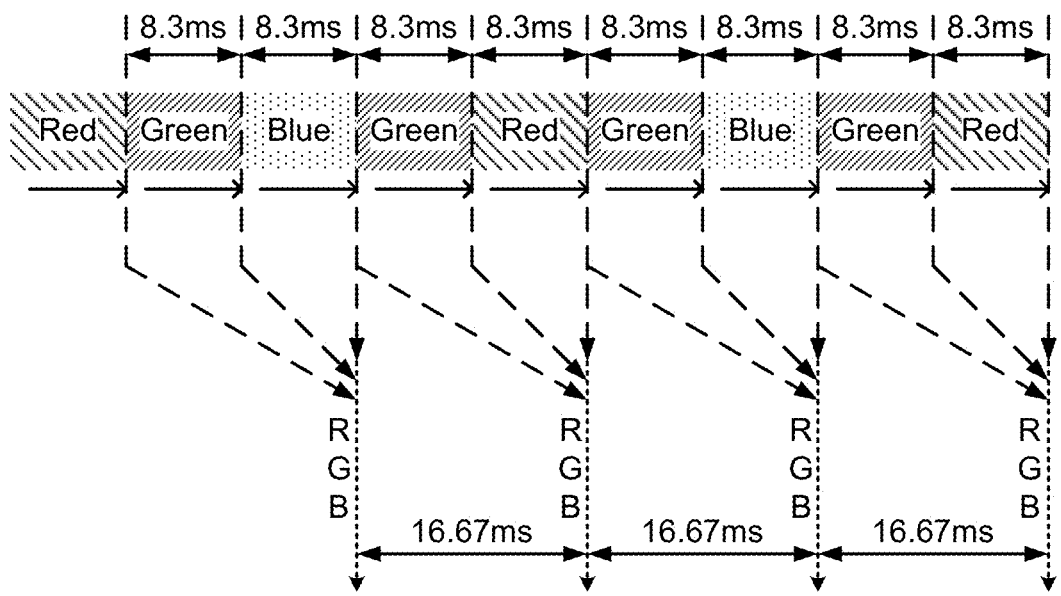

Referring now to FIGS. 15 and 16, the RG1BG2RG1BG2 pattern reconstruction illustrated in FIG. 16 allows 60 fps (image frames per second) output with 120 fps (frames per second) input in an embodiment. Each consecutive frame contains either a red or blue component from the previous frame. In FIG. 16, each color component is available in 8.3 ms and the resulting image frame has a period of 16.67 ms. In general for this pulsing scheme, the image frame has a period twice of that of the incoming colored frame as shown in FIG. 15. In other embodiments, different pulsing schemes may be employed. For example, embodiments may be based on the timing of each color component or frame (T1) and the image frame having a period twice that of the incoming color frame (2×T1). Different frames within the sequence may have different frame periods and the average capture rate could be any multiple of the final image frame rate.

FIGS. 17-20 illustrate color correction methods and hardware schematics for use with a partitioned light system. It is common in digital imaging to manipulate the values within image data in order to correct the output to meet user expectations or to highlight certain aspects of the imaged object. Most commonly this is done in satellite images that are tuned and adjusted to emphasize one data type over another. Most often, in satellite acquired data there is the full spectrum of electromagnetic energy available because the light source is not controlled, i.e., the sun is the light source. In contrast, there are imaging conditions where the light is controlled and even provided by a user. In such situations, calibration of the image data is still desirable, because without calibration improper emphasis may be given to certain data over other data. In a system where the light is controlled by the user, it is advantageous to provide emissions of light that are known to the user, and may be only a portion of the electromagnetic spectrum or a plurality of portions of the full electromagnetic spectrum. Calibration remains important in order to meet the expectations of the users and check for faults within the system. One method of calibration can be a table of expected values for a given imaging condition that can be compared to the data from the sensor. An embodiment may include a color neutral scene having known values that should be output by the imaging device and the device may be adjusted in order to meet those known values when the device samples the color neutral scene.

Figure 17:
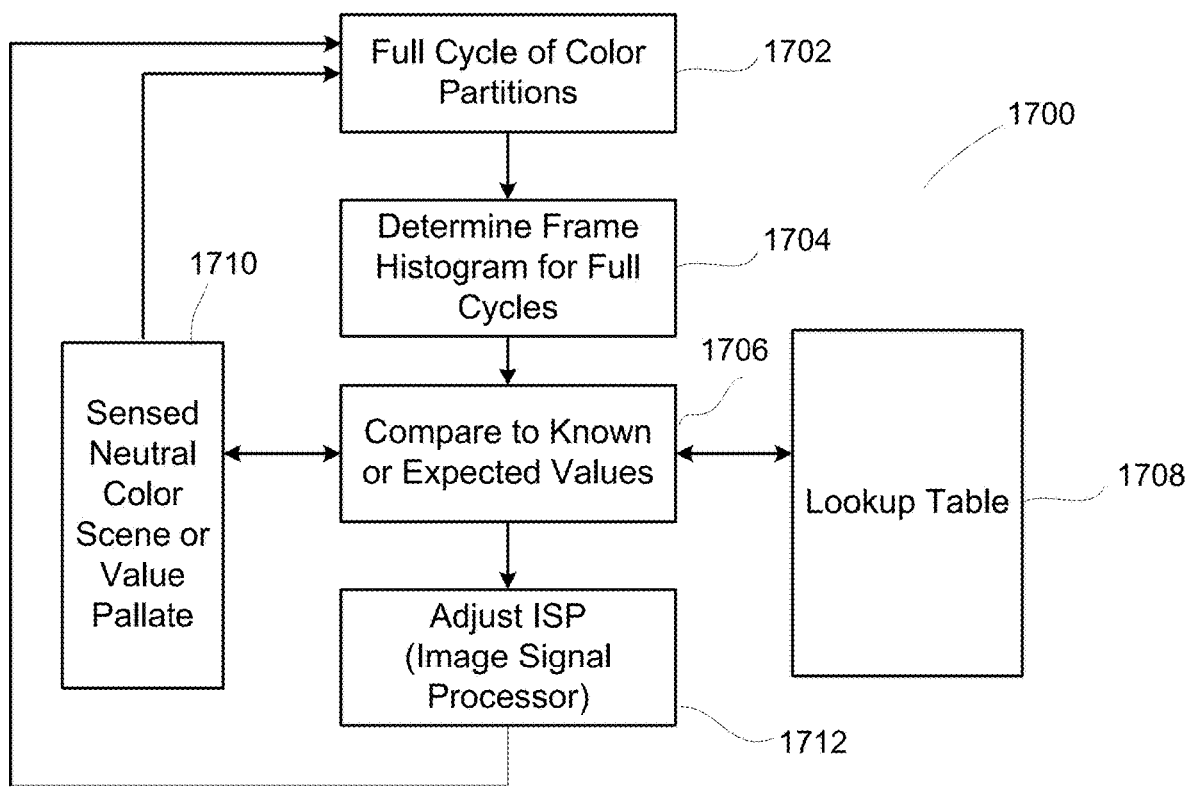

In use, and upon start up, the system may sample a color neutral scene at 1710 (as illustrated in FIG. 17) by running a full cycle of a plurality of electromagnetic spectrum partitions at 1702. A table of values 1708 may be formed to produce a histogram for the frame at 1704. The values of the frame can be compared to the known or expected values from the color neutral scene at 1706. The imaging device may then be adjusted to meet the desired output at 1712. In an embodiment illustrated in FIG. 17, the system may comprise an image signal processor (ISP) that may be adjusted to color correct the imaging device.

It should be noted that because each partitioned spectrum of light may have different energy values, the sensor and/or light emitter may be adjusted to compensate for the differences in the energy values. For example in an embodiment, because the blue light spectrum has a lower quantum efficiency than the red light spectrum with regard to silicon based imagers, the sensor's responsiveness can then be adjusted to be less responsive during the red cycle and more responsive during the blue cycle. Conversely, the emitter may emit blue light at a higher intensity, because of the lower quantum efficiency of the blue light, than red light in order to produce a correctly exposed image.

Figure 18:
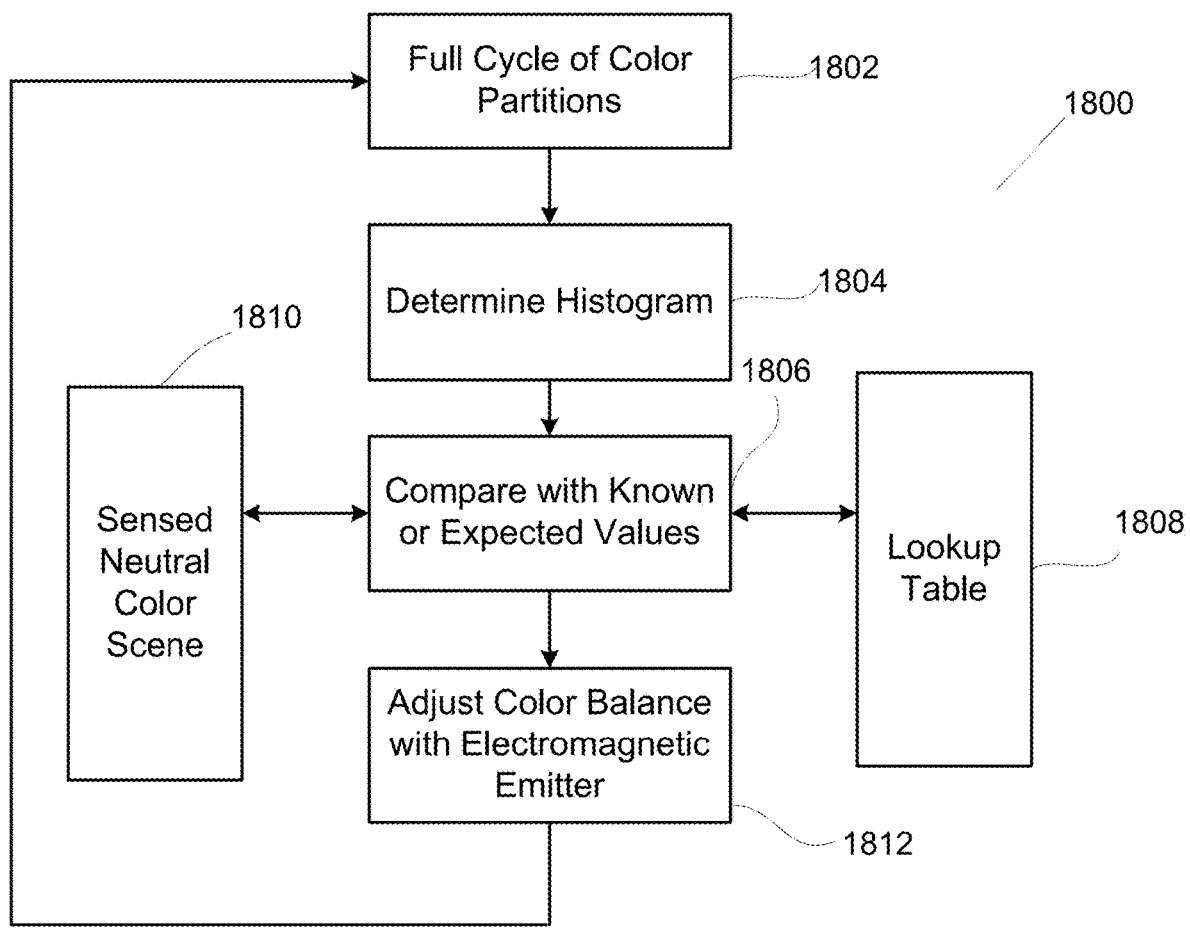
Figure 19:
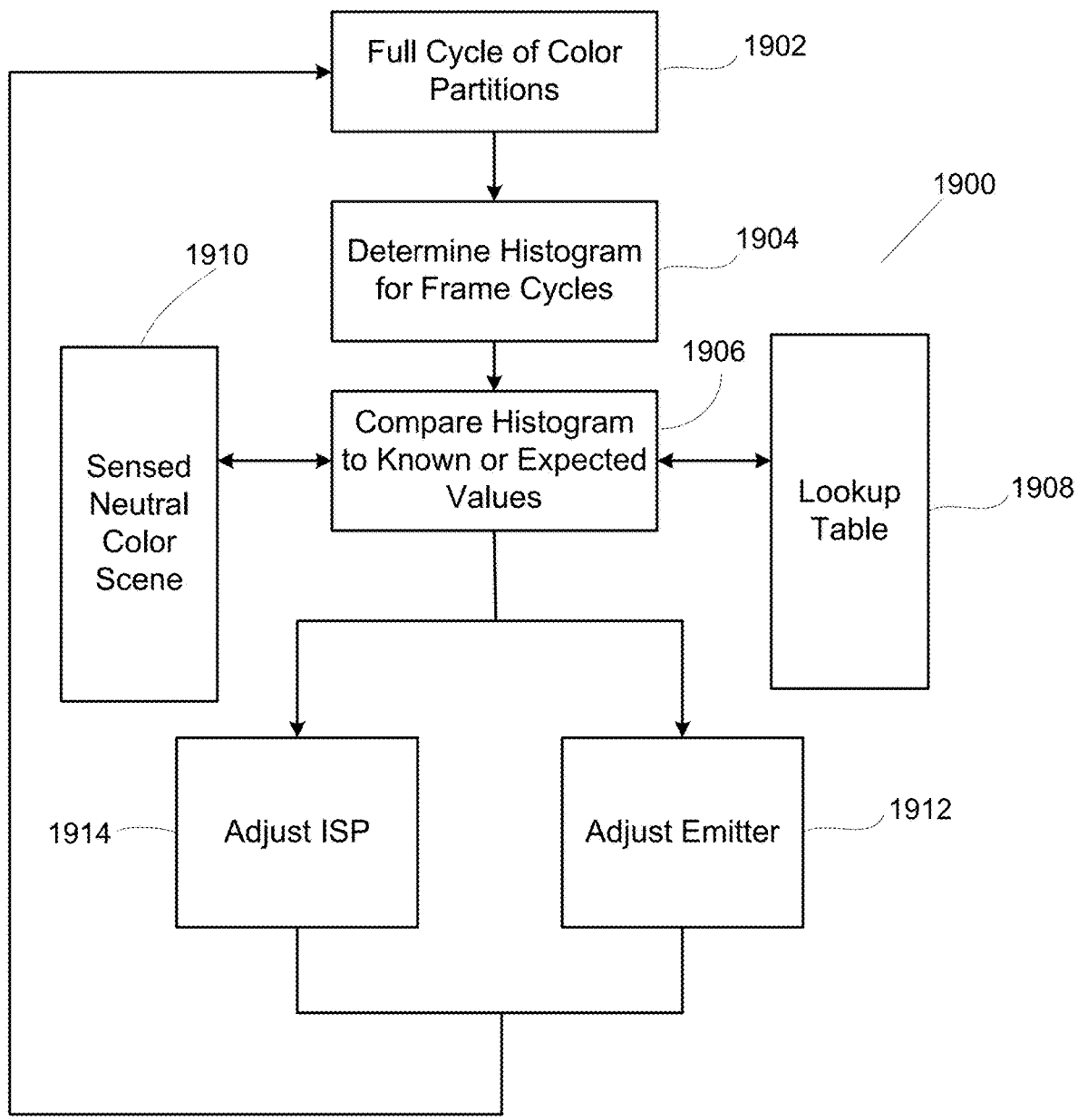

In an embodiment illustrated in FIG. 18, where the light source emissions are provided and controllable by the system, adjustment of those light emissions can be made in order to color correct an image at 1800. Adjustments may be made to any aspect of the emitted light such as magnitude, duration (i.e., time-on), or the range within the spectrum partition. Additionally, both the emitter and the sensor can be adjusted concurrently in some embodiments as shown in FIG. 19.

Figure 20:
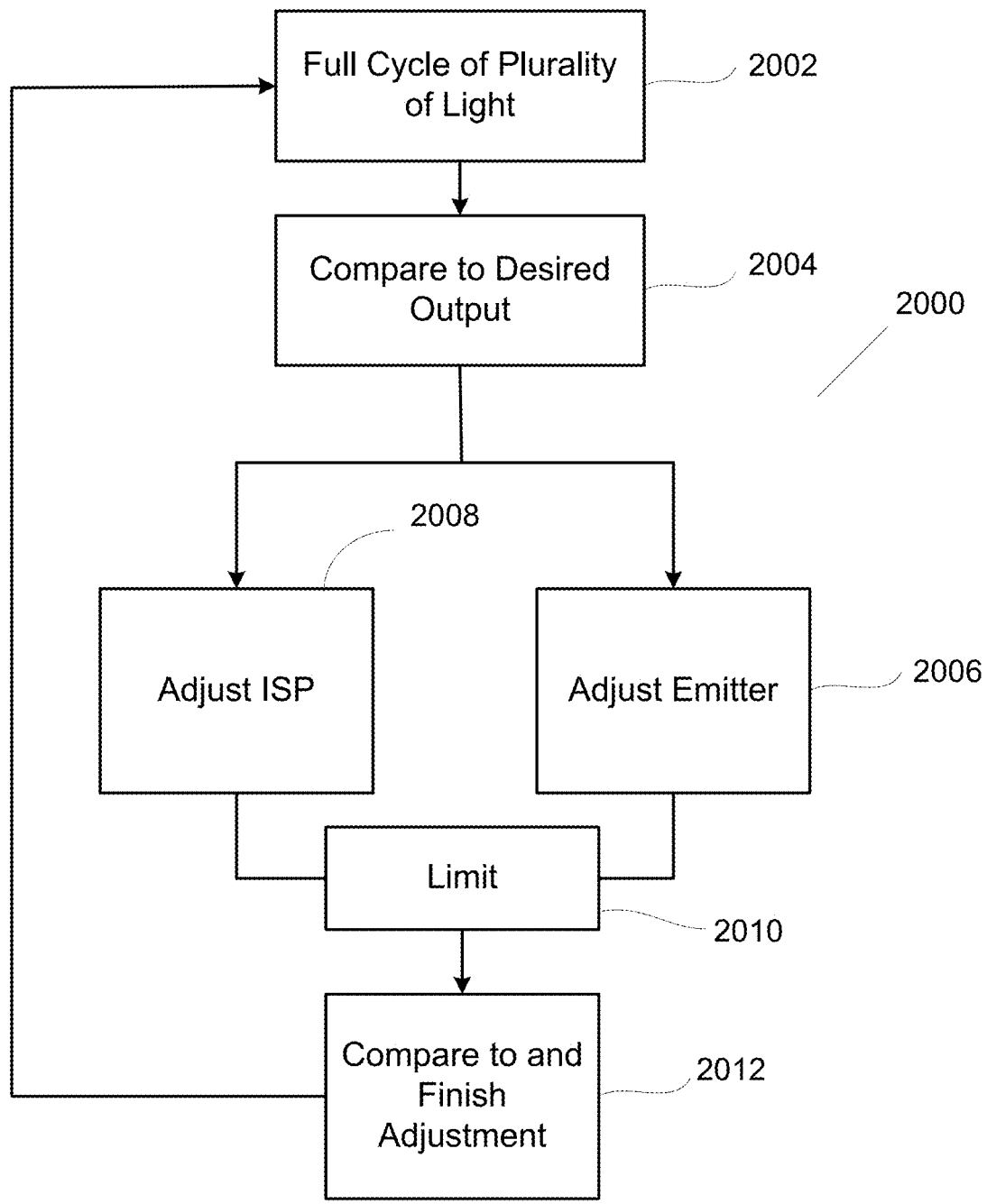

In order to reduce the amount of noise and artifacts within the outputted image stream or video, fractionalized adjustments may be made to the sensor or emitter within the system as can be seen in FIG. 20. Illustrated in FIG. 20 is a system 2000 where both the emitter 2006 and the sensor 2008 can be adjusted, but an imaging device where either the emitter or sensor is adjusted during use or for a portion of use is also contemplated and is within the scope of this disclosure. It may be advantageous to adjust only the emitter during one portion of use and adjust only the sensor during another portion of use, while further yet adjusting both concurrently during a portion of use. In any of the above embodiments, improved image quality may be obtained by limiting the overall adjustments that the system can make between frame cycles. In other words, an embodiment may be limited such that the emitter may only be adjusted a fraction of its operational range at any time between frames. Likewise, the sensor may be limited such that it may only be adjusted a fraction of its operational range at any time between frames. Furthermore, both the emitter and sensor may be limited such that they may only be adjusted together at a fraction of their respective operational ranges at any time between frames in an embodiment.

In an exemplary embodiment, a fractional adjustment of the components within the system may be performed, for example, at about 0.1 dB of the operational range of the components in order to correct the exposure of the previous frame. The 0.1 dB is merely an example and it should be noted that is other embodiments the allowed adjustment of the components may be any portion of their respective operational ranges. The components of the system can change by intensity or duration adjustment that is generally governed by the number of bits (resolution) output by the component. The component resolution may be typically between a range of about 10-24 bits, but should not be limited to this range as it is intended to include resolutions for components that are yet to be developed in addition to those that are currently available. For example, after a first image frame it is determined that the scene is too blue when observed, then the emitter may be adjusted to decrease the magnitude or duration of the pulse of the blue light during the blue cycle of the system by a fractional adjustment as discussed above, such as about 0.1 dB.

In this exemplary embodiment, more than 10 percent may have been needed, but the system has limited itself to 0.1 dB adjustment of the operational range per system cycle. Accordingly, during the next system cycle the blue light can then be adjusted again, if needed. Fractionalized adjustment between cycles may have a damping effect of the outputted imaged and will reduce the noise and artifacts when operating emitters and sensors at their operation extremes. It may be determined that any fractional amount of the components' operational range of adjustment may be used as a limiting factor, or it may be determined that certain embodiments of the system may comprise components that may be adjusted over their entire operational range.

Additionally, the optical black area of any image sensor may be used to aid in image correction and noise reduction. In an embodiment, the values read from the optical black area may be compared to those of the active pixel region of a sensor in order to establish a reference point to be used in image data processing. FIG. 21 shows the kind of sensor correction processes that might be employed in a color pulsed system. CMOS image sensors typically have multiple non-idealities that have a detrimental effect on image quality, particularly in low light. Chief among these are fixed pattern noise and line noise. Fixed pattern noise is a dispersion in the offsets of the sense elements. Typically most of the FPN is a pixel to pixel dispersion which stems, among other sources, from random variations in dark current from photodiode to photodiode. This looks very unnatural to the viewer. Even more egregious is column FPN, resulting from offsets in the readout chain associated with a particular columns of pixels. This results in perceived vertical stripes within the image.

Being in total control of the illumination has the benefit that entire frames of dark data may periodically be acquired and used to correct for the pixel and column offsets. In the illustrated example, a single frame buffer may be used to make a running average of the whole frame without light using, e.g., simple exponential smoothing. This dark average frame would be subtracted from every illuminated frame during regular operation.

Line-Noise is a stochastic temporal variation in the offsets of pixels within each row. Since it is temporal, the correction must be computed anew for each line and each frame. For this purpose there are usually many optically blind (OB) pixels within each row in the array, which must first be sampled to assess the line offset before sampling the light sensitive pixels. The line offset is then simply subtracted during the line noise correction process.

In the example in FIG. 21, there are other corrections concerned with getting the data into the proper order, monitoring and controlling the voltage offset in the analog domain (black clamp) and identifying/correcting individual defective pixels.

Figure 22:
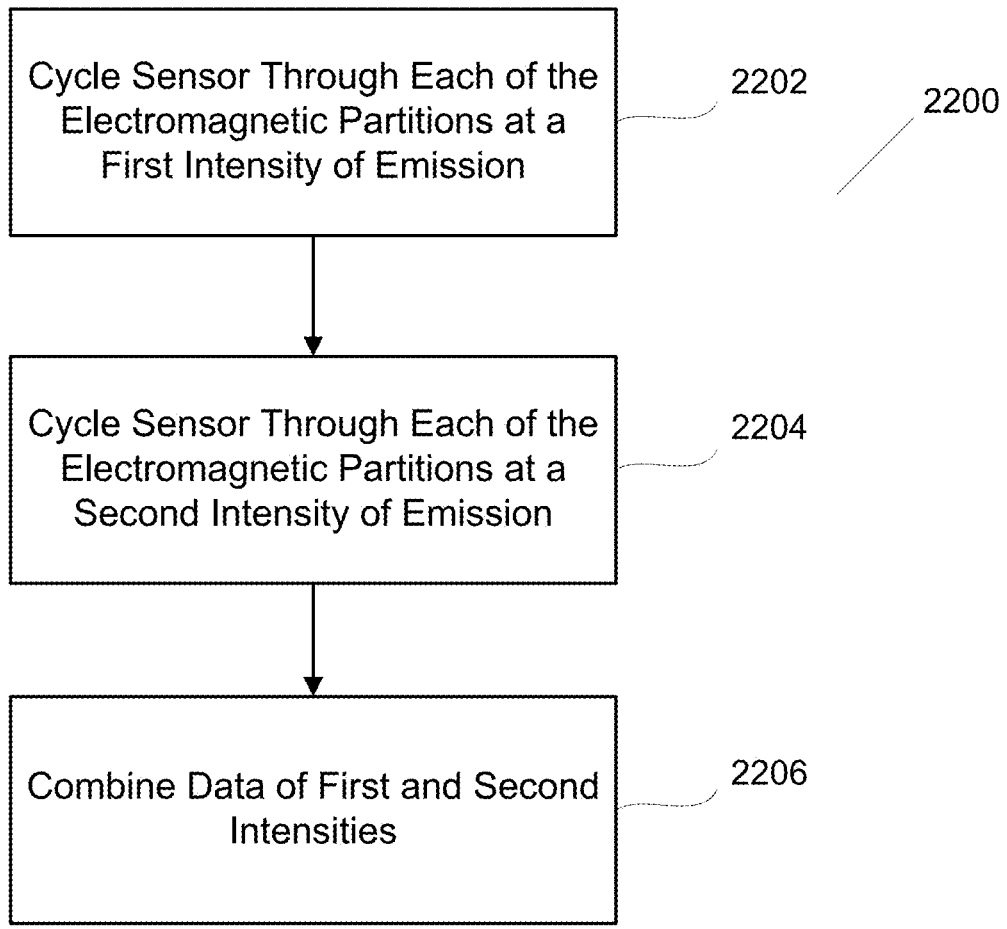
FIGS. 22-23 illustrate method and hardware schematics for increasing the dynamic range within a closed or limited light environment in accordance with the principles and teachings of the disclosure.
Figure 23:
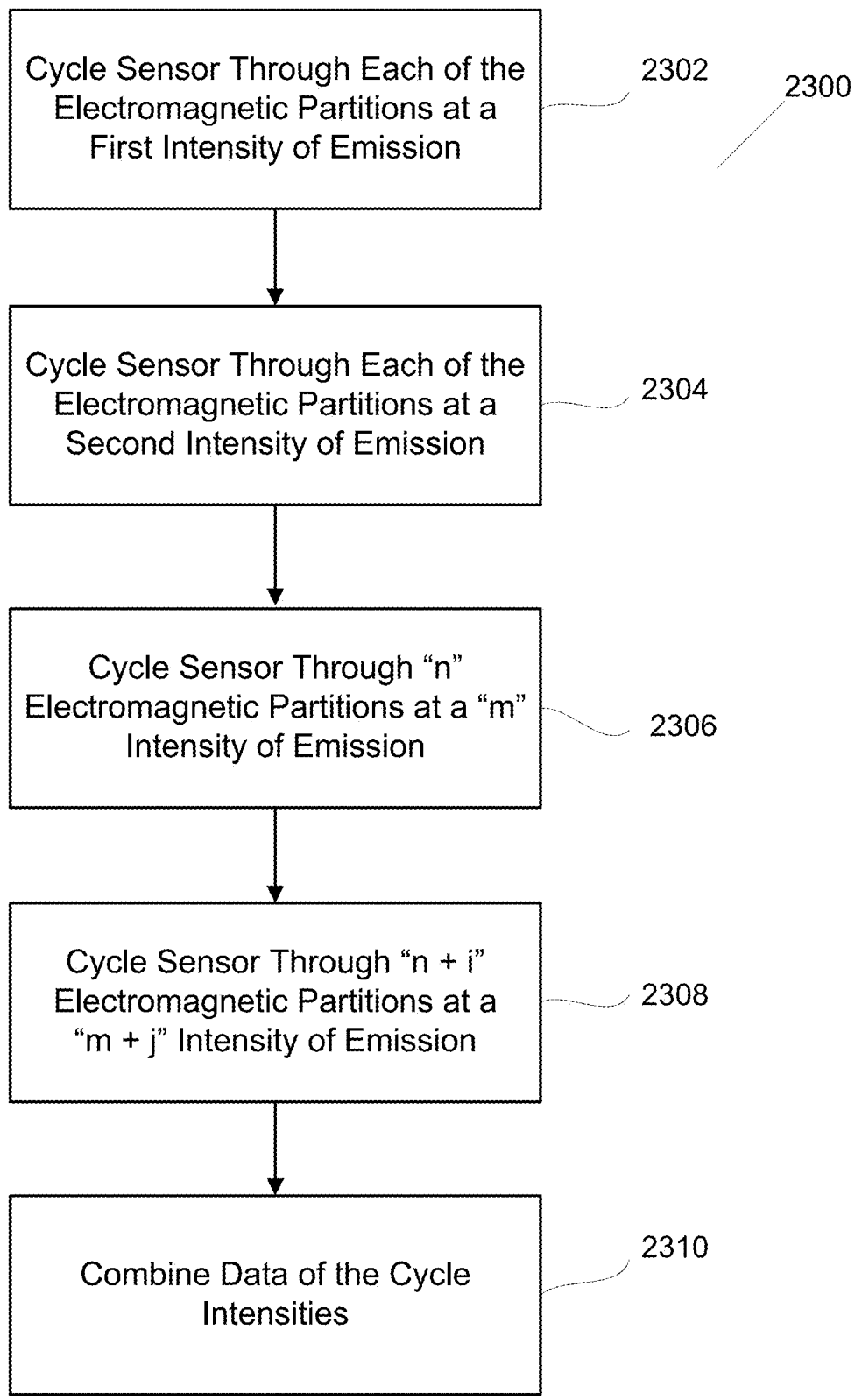

FIGS. 22 and 23 illustrate method and hardware schematics for increasing the dynamic range within a closed or limited light environment. In an embodiment, exposure inputs may be input at different levels over time and combine in order to produce greater dynamic range. As can be seen in FIG. 22, an imaging system may be cycled at a first intensity for a first frame cycle at 2202 and then subsequently cycled at a second intensity for a second frame cycle at 2204, and then by combining those first and second cycles into a single image frame at 2206 so that greater dynamic range can be achieved. Greater dynamic range may be especially desirable because of the limited space environment in which an imaging device is used. In limited space environments that are light deficient or dark, except for the light provided by the light source, and where the light source is close to the light emitter, exposure has an exponential relationship to distance. For example, objects near the light source and optical opening of the imaging device tend to be over exposed, while objects farther away tend to be extremely under exposed because there is very little (in any) ambient light present.

As can be seen in FIG. 23, the cycles of a system having emissions of electromagnetic energy in a plurality of partitions (e.g., frames) may be serially cycled according to the partitions of electromagnetic spectrum at 2300. For example, in an embodiment where the emitter emits lasers in a distinct red partition, a distinct blue partition, and a distinct green partition, the two frame cycle data sets that are going to be combined may be in the form of:

red at intensity one at 2302,
 red at intensity two at 2304,
 blue at intensity one at 2302,
 blue at intensity two at 2304,
 green at intensity one at 2302,
 green at intensity two at 2304.

Alternatively, the system may be cycled in the form of:

red at intensity one at 2302,
 blue at intensity one at 2302,
 green at intensity one at 2302,
 red at intensity two at 2304,
 blue at intensity two at 2304,
 green at intensity two at 2304.

In such an embodiment a first image may be derived from the intensity one values, and a second image may be derived from the intensity two values, and then combined or processed as complete image data sets at 2310 rather than their component parts.

It is contemplated to be within the scope of this disclosure that any number of emission partitions may be used in any order. As seen in FIG. 23, "n" is used as a variable to denote any number of electromagnetic partitions and "m" is used to denote any level of intensity for the "n" partitions. Such a system may be cycled in the form of:

n at intensity m at 2306,
 n+1 at intensity m+1,
 n+2 at intensity m+2,
 n+i at intensity m+j at 2308.

Accordingly, any pattern of serialized cycles can be used to produce the desired image correction wherein "i" and "j" are additional values within the operation range of the imaging system.

Digital color cameras incorporate an image processing stage for the purpose of maximizing the fidelity of color reproduction. This is accomplished by means of a 3×3 matrix known as the Color Correction Matrix (CCM):

$$\begin{bmatrix} R \\ G \\ B \end{bmatrix}_{OUT} = \begin{bmatrix} R \\ G \\ B \end{bmatrix}_{IN} \begin{bmatrix} a & b & c \\ d & e & f \\ g & h & i \end{bmatrix}$$

The terms in the CCM are tuned using a set of reference colors (e.g., from a Macbeth chart) to provide the best overall match to the sRGB standard color space. The diagonal terms, a, e and i, are effectively white balance gains. Typically though, the white balance is applied separately and the sums of horizontal rows are constrained to be unity, in order no net gain is applied by the CCM itself. The off-diagonal terms effectively deal with color crosstalk in the input channels. Therefore Bayer sensors have higher off-diagonals than 3-chip cameras since the color filer arrays have a lot of response overlap between channels.

There is a signal-to-noise ratio penalty for color correction which is dependent on the magnitude of the off-diagonal terms. A hypothetical sensor with channels that perfectly matched the sRGB components would have the identity matrix CCM:

$$\begin{bmatrix} R \\ G \\ B \end{bmatrix}_{OUT} = \begin{bmatrix} R \\ G \\ B \end{bmatrix}_{IN} \begin{bmatrix} 1 & 0 & 0 \\ 0 & 1 & 0 \\ 0 & 0 & 1 \end{bmatrix}$$

The signal to noise ratio evaluated in the green channel, for a perfect white photosignal of 10,000 e-per pixel (neglecting read noise) for this case would be:

$$SNR = \frac{10,000}{\sqrt{10,000}} = 100$$

Any departure from this degrades the SNR. Take e.g. the following CCM which has values that would not be unusual for a Bayer CMOS sensor:

$$\begin{bmatrix} R \\ G \\ B \end{bmatrix}_{OUT} = \begin{bmatrix} R \\ G \\ B \end{bmatrix}_{IN} \begin{bmatrix} 2.6 & -1.4 & -0.2 \\ -0.3 & 1.6 & -0.3 \\ 0 & -0.6 & 1.6 \end{bmatrix}$$

In this case the green SNR:

$$SNR = \frac{(-3000 + 16,000 - 3000)}{\sqrt{(3000 + 16,000 + 3000)}} = 67.1$$

FIG. 24 shows the result of a full SNR simulation using D65 illumination for a typical Bayer sensor CCM for the case of using the identity matrix versus the tuned CCM. The SNR evaluated for the luminance component is about 6 dB worse as a consequence of the color correction.

Figure 25:
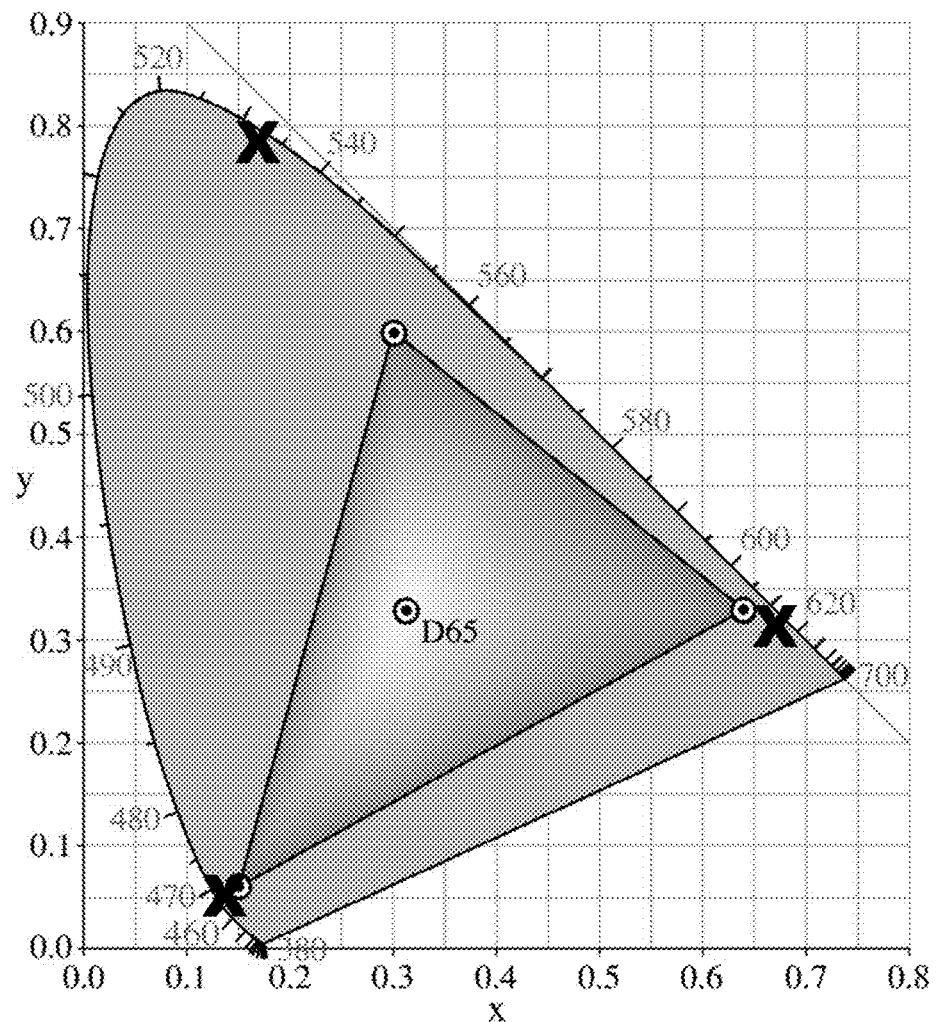
FIG. 25 illustrates the chromaticity of 3 monochromatic lasers compared to the sRGB gamut.

The system described in this disclosure uses monochromatic illumination at three discrete wavelengths, therefore there is no color crosstalk per se. The crosses in FIG. 25 indicate the positions of three wavelengths which are available via laser diode sources (465, 532 & 639 nm), compared the sRGB gamut which is indicated by the triangle.

The off-diagonal terms for the CCM is in this case are drastically reduced, compared with Bayer sensors, which provides a significant SNR advantage.

Figure 26:
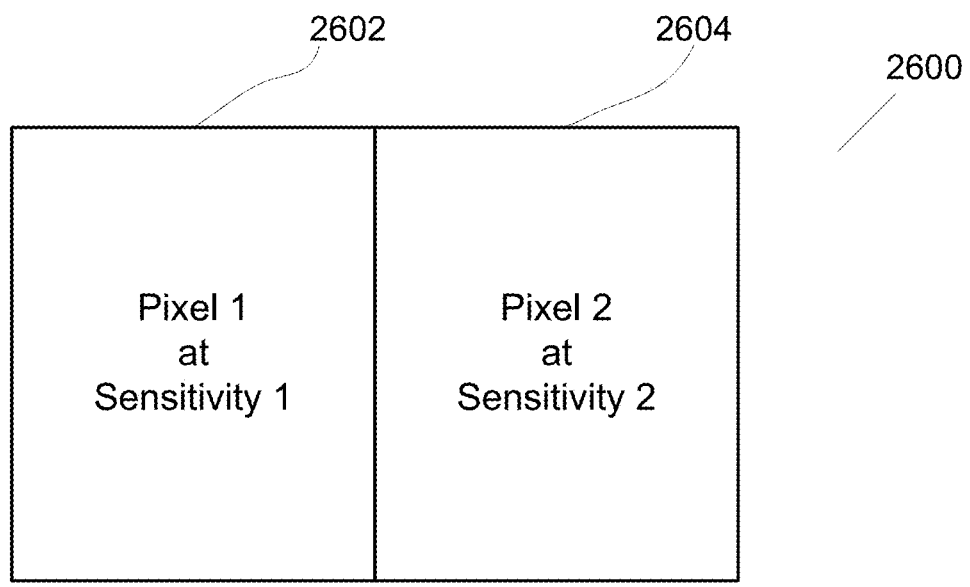

FIG. 26 illustrates an imaging system having increased dynamic range as provided by the pixel configuration of the pixel array of the image sensor. As can be seen in the figure, adjacent pixels 2602 and 2604 may be set at differing sensitivities such that each cycle includes data produced by pixels that are more and less sensitive with respect to each other. Because a plurality of sensitivities can be recorded in a single cycle of the array the dynamic range may be increased if recorded in parallel, as opposed to the time dependent serial nature of other embodiments.

In an embodiment, an array may comprise rows of pixels that may be placed in rows based on their sensitivities. In an embodiment, pixels of differing sensitivities may alternate within a row or column with respect to its nearest neighboring pixels so as to from a checkerboard pattern throughout the array based on those sensitivities. The above may be accomplished through any pixel circuitry share arrangement or in any stand-alone pixel circuit arrangement.

Wide dynamic range can be achieved by having multiple global TX, each TX firing only on a different set of pixels. For example in global mode, a global TX1 signal is firing a set 1 of pixels, a global TX2 signal is firing a set 2 of pixels . . . a global TXn signal is firing a set n of pixels.

Based on FIG. 11, FIG. 27A shows a timing example for 2 different pixel sensitivities (dual pixel sensitivity) in the pixel array. In this case, global TX1 signal fires half of the pixels of the array and global TX2 fires the other half of the pixels. Because global TX1 and global TX2 have different "on" to "off" edge positions, integrated light is different between the TX1 pixels and the TX2 pixels. FIG. 27B shows a different embodiment of the timing for dual pixel sensitivity. In this case, the light pulse is modulated twice (pulse duration and/or amplitude). TX1 pixels integrate P1 pulse and TX2 pixels integrate Pl+P2 pulses. Separating global TX signals can be done many ways. The following are examples:

Differentiating TX lines from each row; and
Sending multiple TX lines per row, each addressing a different set of pixels.

In one implementation, a means of providing wide-dynamic range video is described, which exploits the color pulsing system described in this disclosure. The basis of this is to have multiple flavors of pixels, or pixels that may be tuned differently, within the same monochrome array that are able to integrate the incident light for different durations within the same image frame. An example of the pixel arrangement in the array of such a sensor would be a uniform checkerboard pattern throughout, with two independently variable integration times. For such a case, it is possible to provide both red and blue information within the same image frame. In fact, it is possible to do this at the same time as extending the dynamic range for the green frame, where it is most needed, since the two integration times can be adjusted on a frame by frame basis. The benefit is that the color motion artifacts are less of an issue if all the data is derived from two frames versus three. There is of course a subsequent loss of spatial resolution for the red and blue data, but that is of less consequence to the image quality compared with green, since the luminance component is dominated by green data.

An inherent property of the monochrome wide-dynamic range (WDR) array is that the pixels that have the long integration time must integrate a superset of the light seen by the short integration time pixels. For regular wide-dynamic range operation in the green frames, that is desirable. For the red and blue frames it means that the pulsing must be controlled in conjunction with the exposure periods so as to, e.g., provide blue light from the start of the long exposure and switch to red at the point that the short exposure pixels are turned on (both pixel types have their charges transferred at the same time).

At the color fusion stage, the two flavors of pixels are separated into two buffers. The empty pixels are then filled in using, e.g., linear interpolation. At this point, one buffer contains a full image of blue data and the other red+blue. The blue buffer may be subtracted from the second buffer to give pure red data.

Figure 28A:
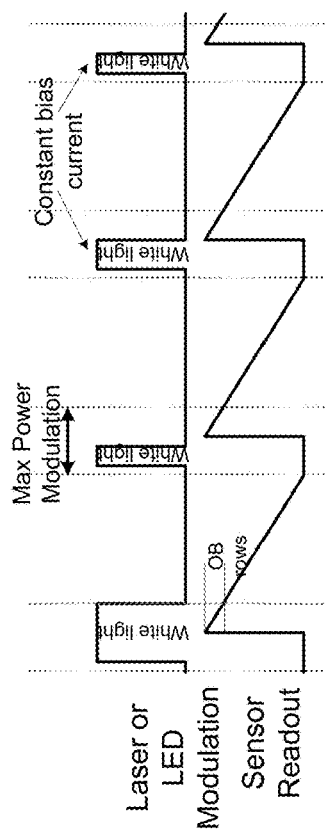
FIGS. 28A-28C illustrate the use of a white light emission that is pulsed and/or synced with a corresponding color sensor.
Figure 28B:
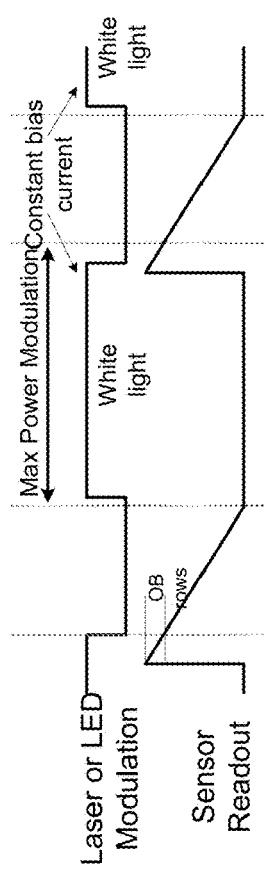
Figure 28C:
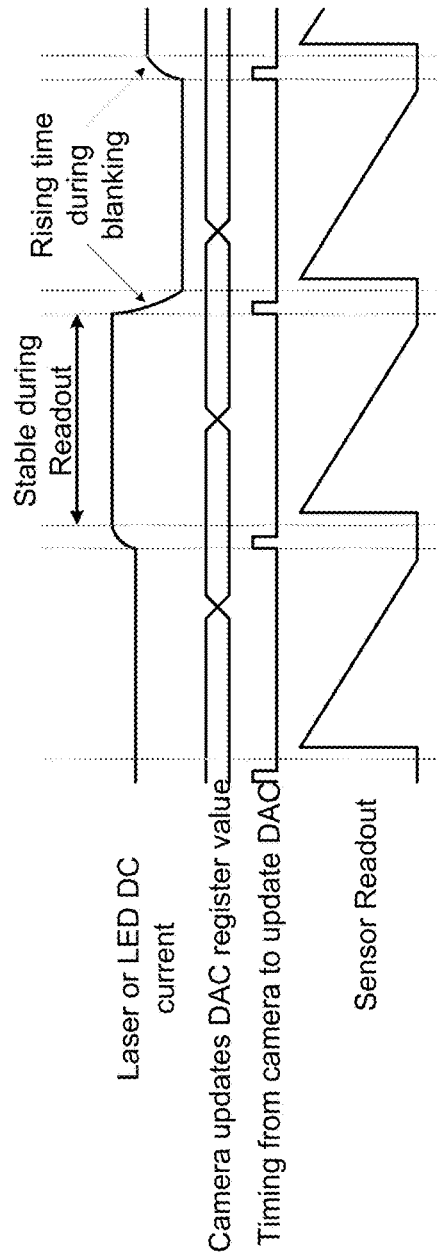

FIGS. 28A-28C illustrate the use of a white light emission that is pulsed and/or synced, or held constant, with a corresponding color sensor. As can be seen in FIG. 28A, a white light emitter may be configured to emit a beam of light during the blanking time of a corresponding sensor so as to provide a controlled light source in a controlled light environment. The light source may emit a beam at a constant magnitude and vary the duration of the pulse as seen in FIG. 28A, or may hold the pulse constant with varying the magnitude in order to achieve correctly exposed data as illustrated in FIG. 28B. Illustrated in FIG. 28C is a graphical representation of a constant light source that can be modulated with varying current that is controlled by and synced with a sensor.

In an embodiment, white light or multi-spectrum light may be emitted as a pulse, if desired, in order to provide data for use within the system (illustrated best in FIGS. 28A-28C). White light emissions in combination with partitions of the electromagnetic spectrum may be useful for emphasizing and de-emphasizing certain aspects within a scene. Such an embodiment might use a pulsing pattern of:

Green pulse;
Red pulse;
Blue pulse;
Green pulse;
Red pulse;
Blue pulse;
White light (multi-spectrum) pulse;
(Repeat)

Any system using an image sensor cycle that is at least two times faster than the white light cycle is intended to fall within the scope of the disclosure. It will be appreciated that any combination of partitions of the electromagnetic spectrum is contemplated herein, whether it be from the visible or non-visible spectrum of the full electromagnetic spectrum.

Figure 29A:
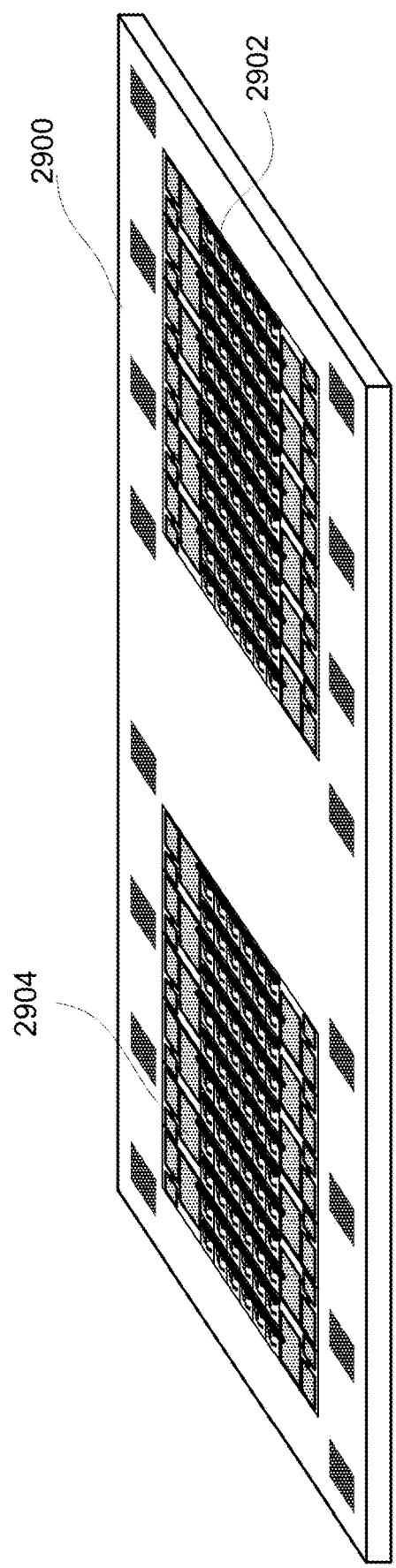
FIGS. 29A and 29B illustrate an implementation having a plurality of pixel arrays for producing a three dimensional image in accordance with the teachings and principles of the disclosure.
Figure 29B:
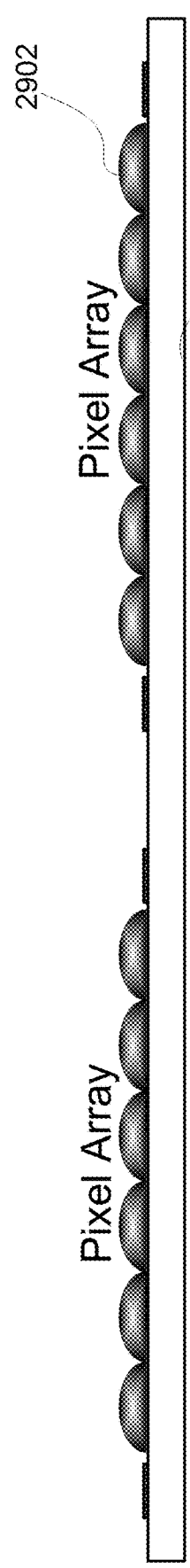

FIGS. 29A and 29B illustrate a perspective view and a side view, respectively, of an implementation of a monolithic sensor 2900 having a plurality of pixel arrays for producing a three dimensional image in accordance with the teachings and principles of the disclosure. Such an implementation may be desirable for three dimensional image capture, wherein the two pixel arrays 2902 and 2904 may be offset during use. In another implementation, a first pixel array 2902 and a second pixel array 2904 may be dedicated to receiving a predetermined range of wave lengths of electromagnetic radiation, wherein the first pixel array is dedicated to a different range of wave length electromagnetic radiation than the second pixel array.

Figure 30A:
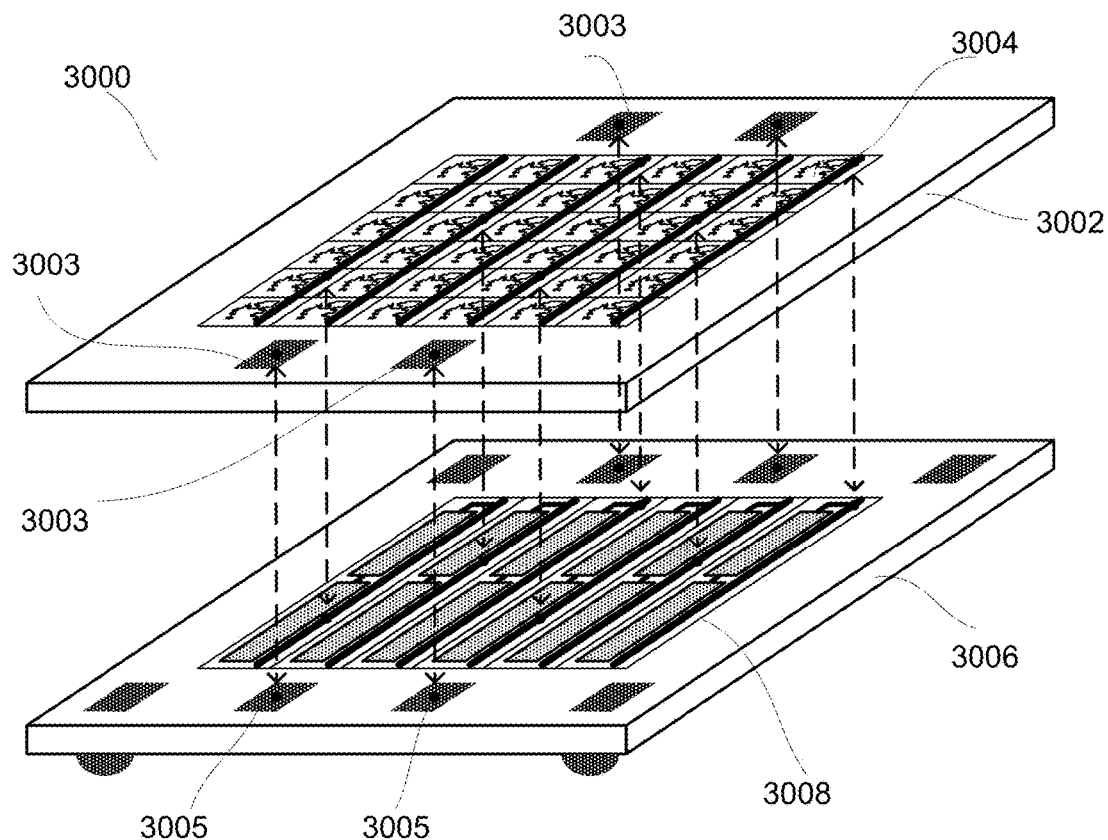
FIGS. 30A and 30B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 30B:
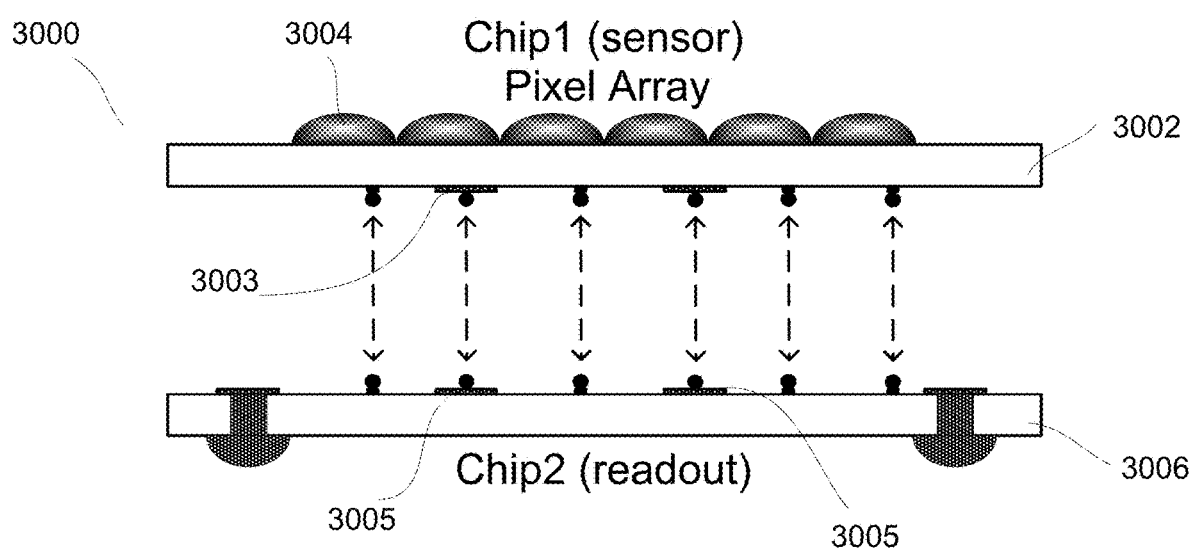

FIGS. 30A and 30B illustrate a perspective view and a side view, respectively, of an implementation of an imaging sensor 3000 built on a plurality of substrates. As illustrated, a plurality of pixel columns 3004 forming the pixel array are located on the first substrate 3002 and a plurality of circuit columns 3008 are located on a second substrate 3006. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 3002 of the two substrates/chips may be processed using an image CMOS process. The first substrate/chip 3002 may be comprised either of a pixel array exclusively or a pixel array surrounded by limited circuitry. The second or subsequent substrate/chip 3006 may be processed using any process, and does not have to be from an image CMOS process. The second substrate/chip 3006 may be, but is not limited to, a highly dense digital process in order to integrate a variety and number of functions in a very limited space or area on the substrate/chip, or a mixed-mode or analog process in order to integrate for example precise analog functions, or a RF process in order to implement wireless capability, or MEMS (Micro-Electro-Mechanical Systems) in order to integrate MEMS devices. The image CMOS substrate/chip 3002 may be stacked with the second or subsequent substrate/chip 3006 using any three-dimensional technique. The second substrate/chip 3006 may support most, or a majority, of the circuitry that would have otherwise been implemented in the first image CMOS chip 3002 (if implemented on a monolithic substrate/chip) as peripheral circuits and therefore have increased the overall system area while keeping the pixel array size constant and optimized to the fullest extent possible. The electrical connection between the two substrates/chips may be done through interconnects 3003 and 3005, which may be wirebonds, bump and/or TSV (Through Silicon Via).

FIGS. 31A and 31B illustrate a perspective view and a side view, respectively, of an implementation of an imaging sensor 3100 having a plurality of pixel arrays for producing a three dimensional image. The three dimensional image sensor may be built on a plurality of substrates and may comprise the plurality of pixel arrays and other associated circuitry, wherein a plurality of pixel columns 3104a forming the first pixel array and a plurality of pixel columns 3104b forming a second pixel array are located on respective substrates 3102a and 3102b, respectively, and a plurality of circuit columns 3108a and 3108b are located on a separate substrate 3106. Also illustrated are the electrical connections and communications between columns of pixels to associated or corresponding column of circuitry.

It will be appreciated that the teachings and principles of the disclosure may be used in a reusable device platform, a limited use device platform, a re-posable use device platform, or a single-use/disposable device platform without departing from the scope of the disclosure. It will be appreciated that in a re-usable device platform an end-user is responsible for cleaning and sterilization of the device. In a limited use device platform the device can be used for some specified amount of times before becoming inoperable. Typical new device is delivered sterile with additional uses requiring the end-user to clean and sterilize before additional uses. In a re-posable use device platform a third-party may reprocess the device (e.g., cleans, packages and sterilizes) a single-use device for additional uses at a lower cost than a new unit. In a single-use/disposable device platform a device is provided sterile to the operating room and used only once before being disposed of.

Figure 32:
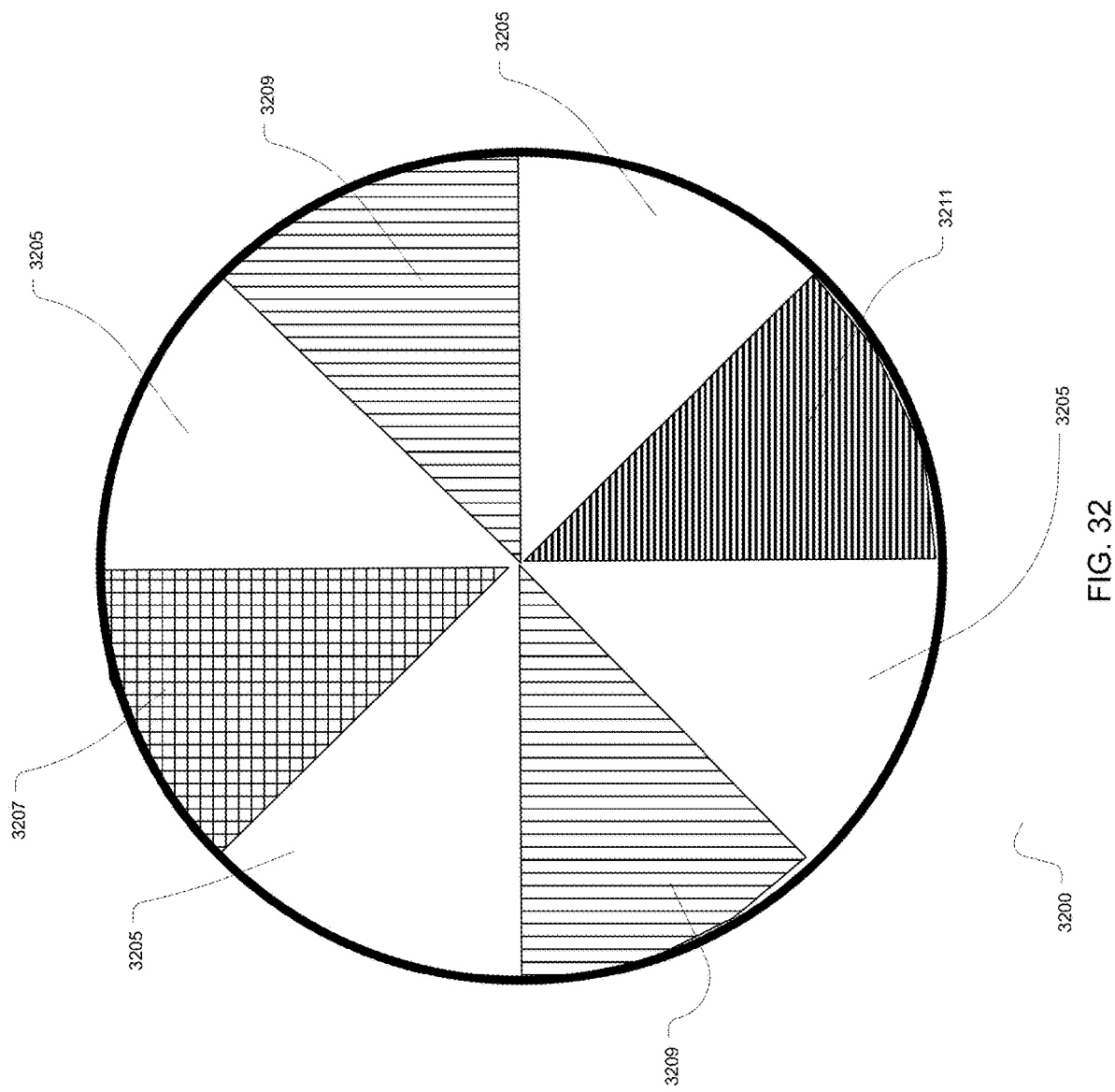
FIGS. 32-36 illustrate embodiments of emitters comprising various mechanical filter and shutter configurations.

An embodiment of an emitter may employ the use of a mechanical shutter and filters to create pulsed color light. As illustrated in FIG. 32, an alternate method to produce pulsed color light, using a white light source and a mechanical color filter and shutter system 3200. The wheel could contain a pattern of translucent color filter windows and opaque sections for shuttering. The opaque sections would not allow light through and would create a period of darkness in which the sensor read-out could occur. The white light source could be based on any technology: laser, LED, xenon, halogen, metal halide, or other. The white light can be projected through a series of color filters 3207, 3209 and 3211 of the desired pattern of colored light pulses. One embodiment pattern could be Red filter 3207, Green filter 3209, Blue filter 3211, Green filter 3209. The filters and shutter system 3200 could be arranged on a wheel that spins at the required frequency to be in sync with the sensor such that knowledge of the arch length and rate of rotation of the mechanical color filters 3207, 3209 and 3211 and shutters 3205 system would provide timing information for the operation of a corresponding monochromatic image sensor.

Figure 33:
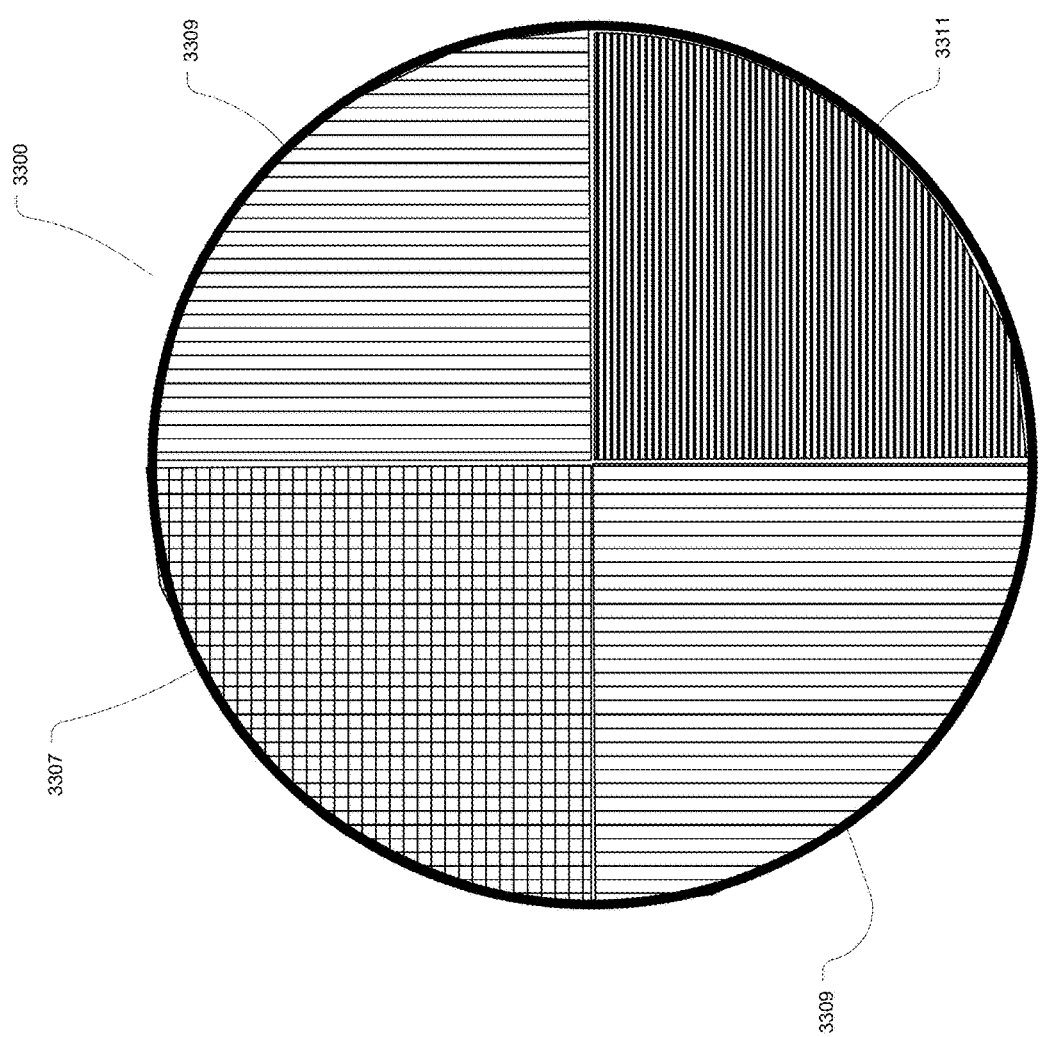

Illustrated in FIG. 33 an embodiment may comprise a pattern of only translucent color filters 3307, 3309 and 3311 on a filter wheel 3300. In the present configuration, a different shutter may be used. The shutter could be mechanical and could dynamically adjust the "pulse" duration by varying is size. Alternately the shutter could be electronic and incorporated into the sensor design. A motor spinning the filter wheel 3300 will need to communicate with, or be controlled in conjunction with the sensor such that knowledge of the arch length and rate of rotation of the mechanical color filters 3307, 3309 and 3311 system would provide timing information for the operation of the corresponding monochromatic image sensor. The control system will need to know the proper color filter for each frame captured by the sensor so that the full-color image frame can be reconstructed properly in the ISP. A color pattern of RGBG is shown, but other colors and/or patterns could be used if advantageous. The relative size of the color sections is shown as equal, but could be adjusted if advantageous. The mechanical structure of the filter is shown as a circle moving rotationally, but could be rectangular with a linear movement, or a different shape with a different movement pattern.

Figure 34:
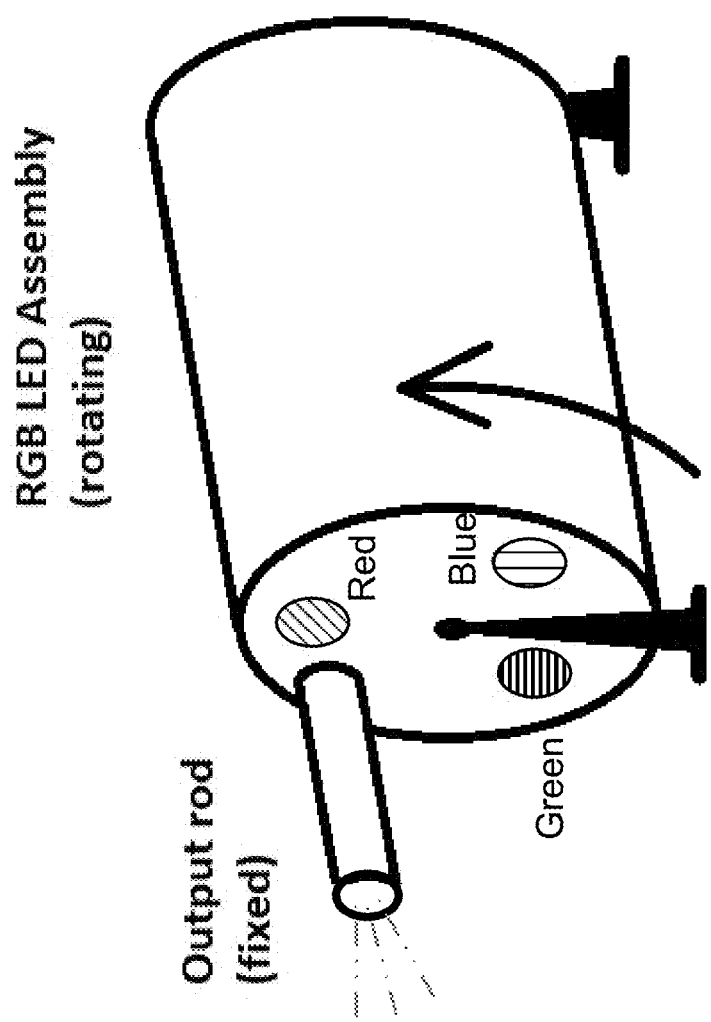

As illustrated FIG. 34, an embodiment for pulsing color light may consist of a mechanical wheel or barrel that holds the electronics and heat sinks for Red, Green, Blue or White LEDS. The LEDs would be spaced at the distance that would be related to the rate of spin or twist of the barrel or wheel to allow for timing of light pulsing consistent with other embodiments in the patent. The wheel or barrel would be spun using an electrical motor and a mechanical bracket attaching the wheel or barrel to the electrical motor. The motor would be controlled using a microcontroller, FPGA, DSP, or other programmable device that would contain a control algorithm for proper timing as described in the patent. There would be a mechanical opening on one side that would be optically coupled to a fiber optic to transport the fiber to the end of the scopes with the methods described in the patent. This coupling could also have a mechanical aperture that could open and close to control the amount of light allowed down the fiber optic cable. This would be a mechanical shutter device alternatively one could use the electronic shutter that is designed into a CMOS or CCD type sensor. This device would be difficult to control and calibrate in production but is another way one could get pulsed light into our system.

Figure 35:
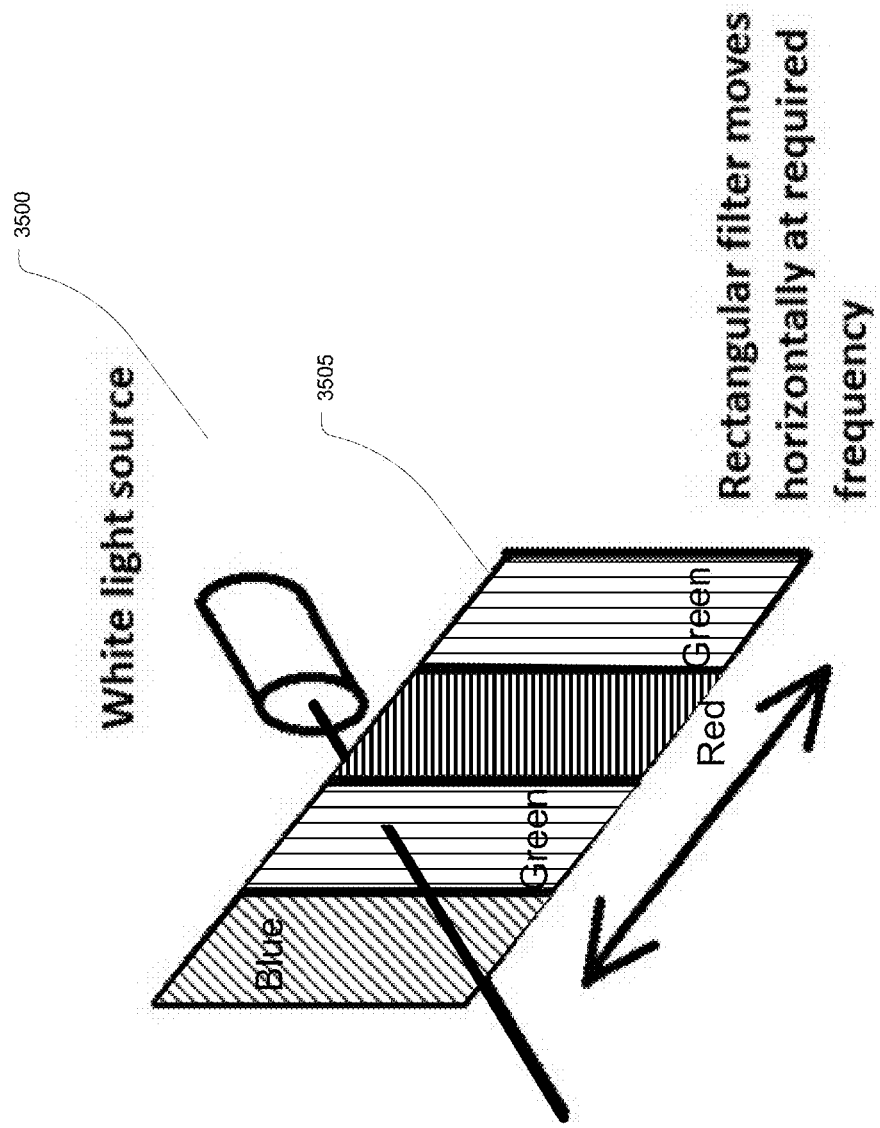

Illustrated in FIG. 35, is an embodiment of an emitter comprising a linear filter and shutter mechanism to provide pulsed electromagnetic radiation.

Figure 36:
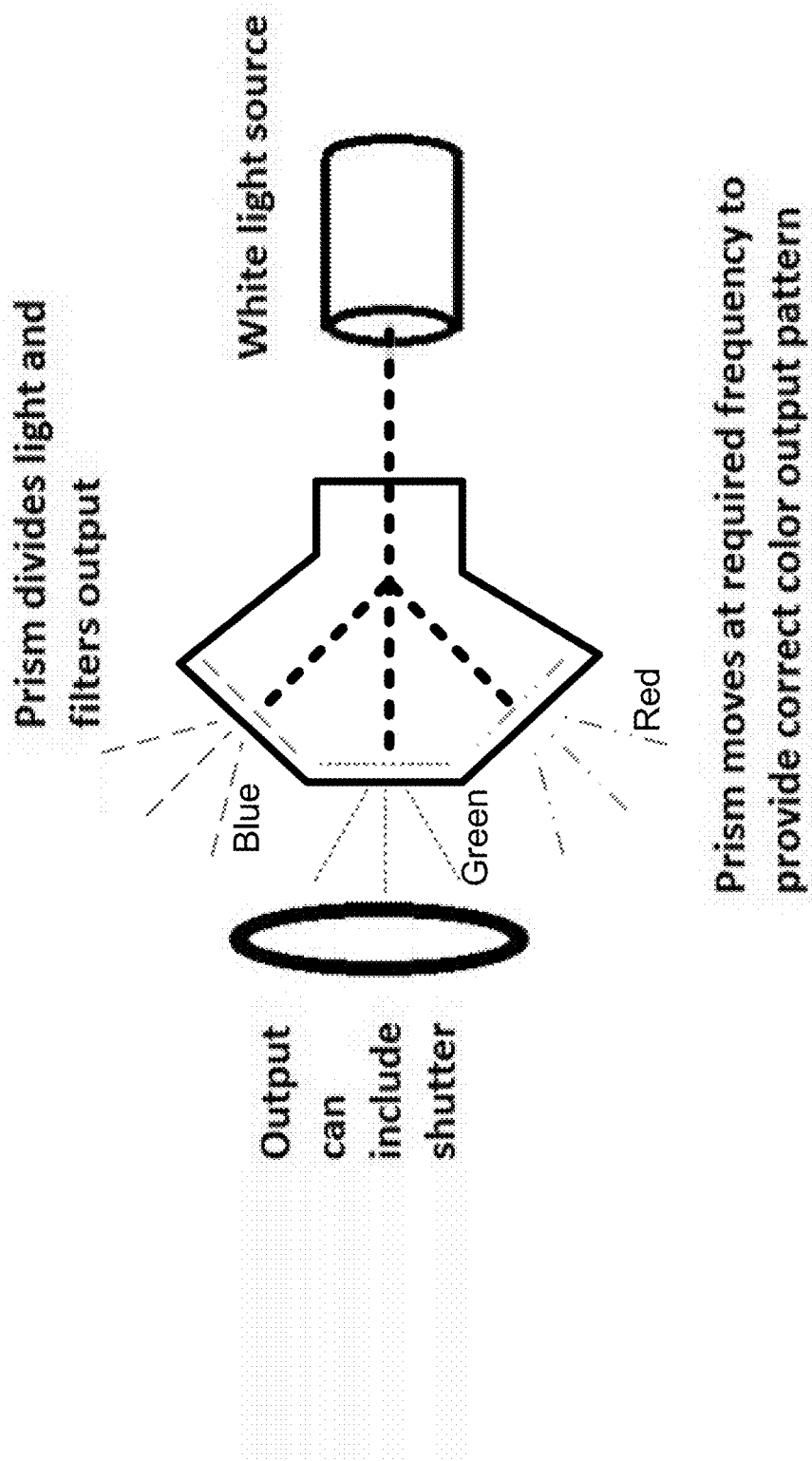

Illustrating in FIG. 36, is an embodiment of an emitter comprising a prism filter and shutter mechanism to provide pulsed electromagnetic radiation.

Additionally, the teachings and principles of the disclosure may include any and all wavelengths of electromagnetic energy, including the visible and non-visible spectrums, such as infrared (IR), ultraviolet (UV), and X-ray.

It will be appreciated that various features disclosed herein provide significant advantages and advancements in the art. The following claims are exemplary of some of those features.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim. Rather, inventive aspects lie in less than all features of a single foregoing disclosed embodiment.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and claims to refer to particular system components. As one skilled in the art will appreciate, components may be referred to by different names. This document does not intend to distinguish between components that differ in name, but not function.

The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A system for digital imaging in an ambient light deficient environment comprising:
   an imaging sensor comprising an array of pixels for sensing electromagnetic radiation;
   an emitter configured to emit pulses of electromagnetic radiation; and
   a controller comprising a processor in electrical communication with the imaging sensor and the emitter, the controller configured to coordinate and synchronize the timing of the pulse of electromagnetic radiation from the emitter during a blanking time of the imaging sensor, the blanking time of the imaging sensor corresponding to the time between a readout of pixels in a last row of the imaging sensor and a beginning of a next frame readout phase of an operational cycle of the imaging sensor,
   wherein the controller captures a plurality of frames during a plurality of operational cycles of the imaging sensor, each one of the plurality of frames being captured during each one of the operational cycles, wherein each of the frames in the plurality of frames correspond to a single pulse of electromagnetic radiation emitted by the emitter and produce imaging sensor data that corresponds in time with each pulse of electromagnetic radiation to produce a plurality of data sets that correspond to the plurality of frames;
   wherein the controller causes the imaging sensor to read each data set corresponding to each of the plurality of frames from the array of pixels during a frame readout phase of the operational cycle of the imaging sensor, the frame readout phase corresponding to the amount of time required to read each pixel in the array of pixels and wherein at least a first frame in the plurality of frames is captured at a point during the operational cycle of the imaging sensor that overlaps the frame readout phase of the operational cycle of the imaging sensor;
   wherein the plurality of frames and the plurality of data sets are combined to form a single image frame; and
   wherein the single image frame is combined with a plurality of image frames to produce a video stream.

2. The system of claim 1, wherein a frame readout phase for the first frame is equal in duration to the frame readout phase for a second frame.

3. The system of claim 1, wherein the blanking time is variable based on the emitted pulses of electromagnetic radiation.

4. The system of claim 1, wherein the system further comprises a connection cable electrically connecting a hand piece and the controller.

5. The system of claim 1, wherein the imaging sensor is a monochrome sensor.

6. The system of claim 1, wherein the emitter is configured to emit the electromagnetic radiation pulses at a plurality of electromagnetic wavelengths.

7. The system of claim 6, wherein the emitter is configured to emit the electromagnetic radiation pulses at three or more electromagnetic wavelengths.

8. The system of claim 7, wherein the three or more electromagnetic wavelengths of electromagnetic radiation emitted by the emitter comprise:
   a green wavelength of electromagnetic radiation;
   a red wavelength of electromagnetic radiation; and
   a blue wavelength of electromagnetic radiation.

9. The system of claim 8, wherein the blue, red and green wavelengths of electromagnetic radiation are emitted in a repeating pattern of pulses.

10. The system of claim 9, wherein the green wavelength is represented in the repeating pattern of pulses twice as often as the red and blue wavelengths.

11. The system of claim 1, wherein the pulses of electromagnetic radiation emitted by the emitter comprise a first wavelength for the first frame and a second wavelength for a second frame.

12. The system of claim 1, wherein the pulses of electromagnetic radiation emitted by the emitter comprise one or more wavelengths that are visible to human eyes.

13. The system of claim 1, wherein the pulses of electromagnetic radiation emitted by the emitter comprise one or more wavelengths that are not visible to human eyes.

14. The system of claim 1, wherein the pulses of electromagnetic radiation emitted by the emitter comprise one or more wavelengths that are visible to human eyes and one or more wavelengths that are not visible to human eyes.

15. The system of claim 1, wherein the pulses of electromagnetic radiation emitted by the emitter comprise differing magnitudes for differing wavelengths.

16. The system of claim 15, wherein one or more pixels in the array of pixels in the imaging sensor include a light sensitivity to the differing wavelengths.

17. The system of claim 1, wherein the imaging sensor is disposed at a distal portion of an endoscope.

18. The system of claim 1, wherein the imaging sensor is disposed within a hand piece.

* * * * *